(12) United States Patent
Bading et al.

(10) Patent No.: US 9,415,090 B2
(45) Date of Patent: Aug. 16, 2016

(54) VEGF-D/VEGFR2/3-MEDIATED REGULATION OF DENDRITES

(75) Inventors: Hilmar Bading, Heidelberg (DE);
Daniela Mauceri, Heidelberg (DE);
Christian Klein, Heidelberg (DE)

(73) Assignee: Universität Heidelberg, Heidelberg (DE)

( * ) Notice: Subject to any disclaimer, the term of this patent is extended or adjusted under 35 U.S.C. 154(b) by 2 days.

(21) Appl. No.: 14/122,116

(22) PCT Filed: Jun. 1, 2012

(86) PCT No.: PCT/EP2012/002333
§ 371 (c)(1),
(2), (4) Date: Nov. 25, 2013

(87) PCT Pub. No.: WO2012/163542
PCT Pub. Date: Dec. 6, 2012

(65) Prior Publication Data
US 2014/0093520 A1   Apr. 3, 2014

Related U.S. Application Data

(63) Continuation-in-part of application No. 13/150,846, filed on Jun. 1, 2011, now abandoned.

(30) Foreign Application Priority Data

Jun. 1, 2011   (EP) ..................................... 11004490

(51) Int. Cl.
| | | |
|---|---|---|
| *A61K 38/04* | (2006.01) | |
| *A61K 38/18* | (2006.01) | |
| *C07K 14/52* | (2006.01) | |
| *C12N 15/113* | (2010.01) | |
| *A61K 48/00* | (2006.01) | |

(52) U.S. Cl.
CPC ............. *A61K 38/1866* (2013.01); *C07K 14/52* (2013.01); *C12N 15/1136* (2013.01); *A61K 48/005* (2013.01); *C12N 2310/14* (2013.01); *C12N 2310/531* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 2005/0032697 A1* | 2/2005 | Alitalo et al. .................. 514/12 |
| 2007/0082848 A1 | 4/2007 | Alitalo et al. | |
| 2008/0070831 A1* | 3/2008 | Achen .................... C07K 14/52 514/8.1 |
| 2009/0324611 A1 | 12/2009 | Eriksson | |

FOREIGN PATENT DOCUMENTS

| | | |
|---|---|---|
| WO | 03/024478 A1 | 3/2003 |
| WO | 2009/036149 A9 | 3/2009 |

OTHER PUBLICATIONS

Licht, Tamar, et al., "VEGF Is Required for Dendritogenesis of Newly Born Olafactory Bulb Interneurons," Development, 2010, vol. 137, No. 2, pp. 261-271.
Mauceri, Daniela, et al., "Nuclear Calcium-VEGFD Signaling Controls Maintenance of Dendrite Arborization Necessary for Memory Formation," Neuron, 2011, vol. 71, No. 1, pp. 117-130.
Rosenstein, Jeffrey M., et al., "Neurotrophic Effects of Vascular Endothelial Growth Factor on Organotypic Cortical Explants and Primary Cortical Neurons," The Journal of Neuroscience, 2003, vol. 23, No. 35, pp. 11036-11044.
Zachary, Ian, "Neuroprotective Role of Vascular Endothelial Growth Factor: Signalling Mechanisms, Biological Function, and Therapeutic Potential," Neurosignals, 2005, vol. 14, No. 5, pp. 207-221.

\* cited by examiner

*Primary Examiner* — Daniel E Kolker
*Assistant Examiner* — Aditi Dutt
(74) *Attorney, Agent, or Firm* — McDonnell Boehnen Hulbert & Berghoff LLP

(57) ABSTRACT

The present invention relates to methods for modulating, i.e. increasing or decreasing, the length and/or the complexity of the dendrites of a neuronal cell by influencing the amount of vascular endothelial growth factor D (VEGFD)-related signaling. The present invention further relates to methods for treating age- and/or disease-related cognitive dysfunctions, or for impairing the memory of a subject. Finally, the present invention relates to recombinant VEGFD (rVEGFD) for use in the treatment of age- and/or disease-related cognitive dysfunctions.

3 Claims, 36 Drawing Sheets

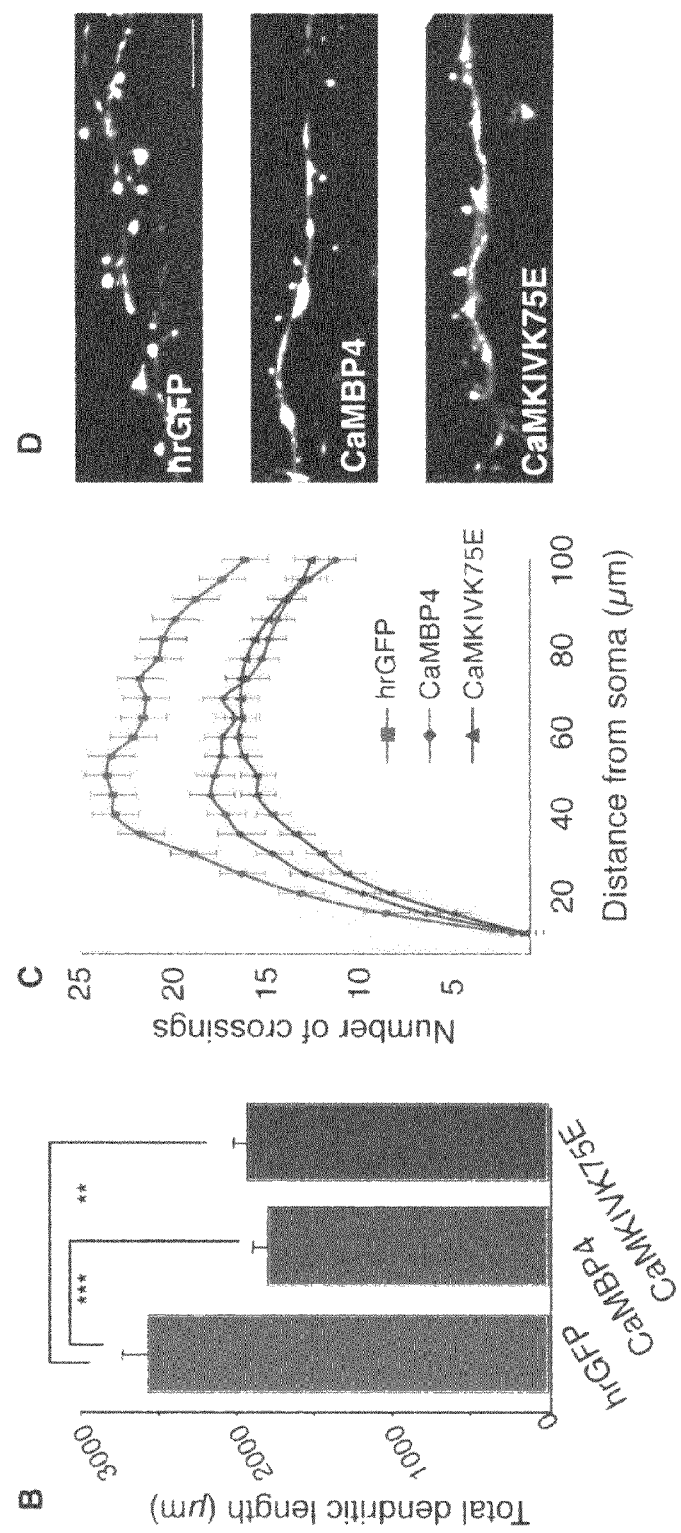
Figure 1 B to D

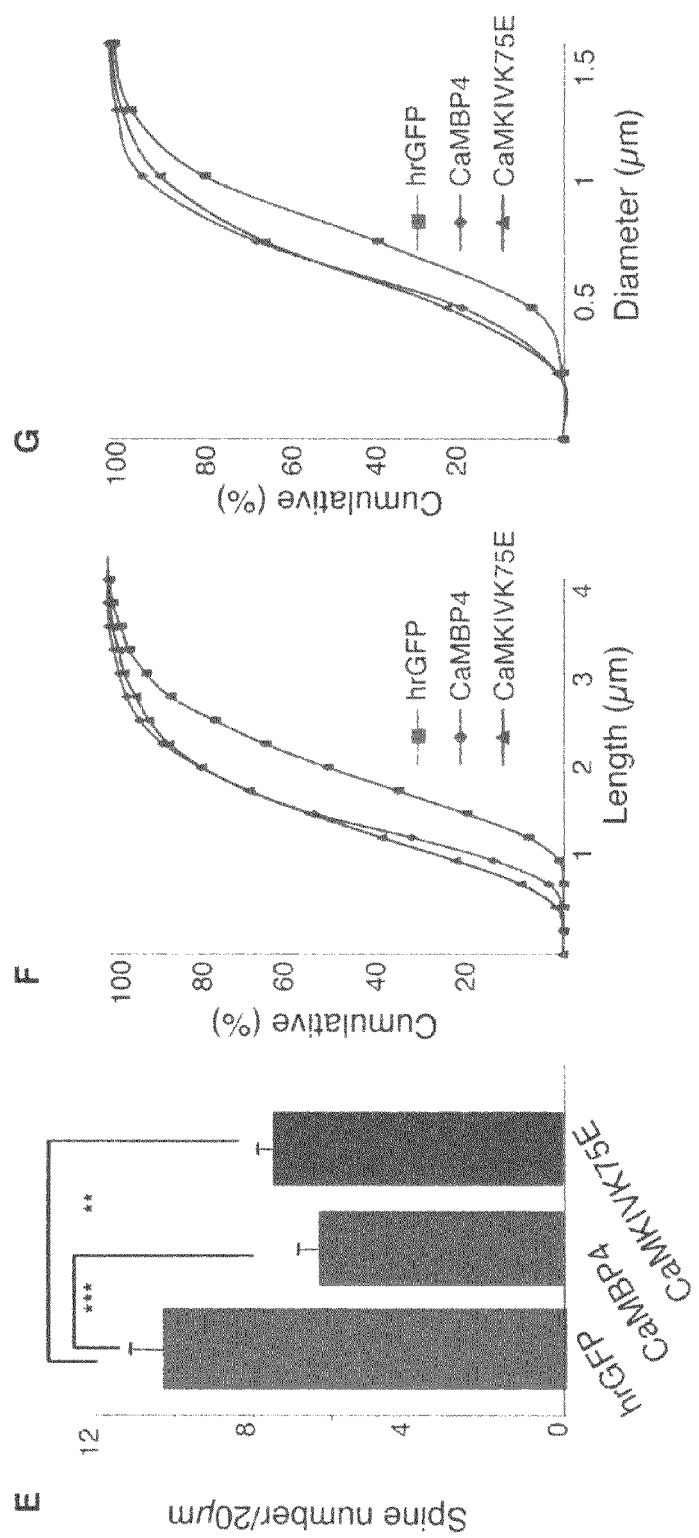
Figure 1 E to G

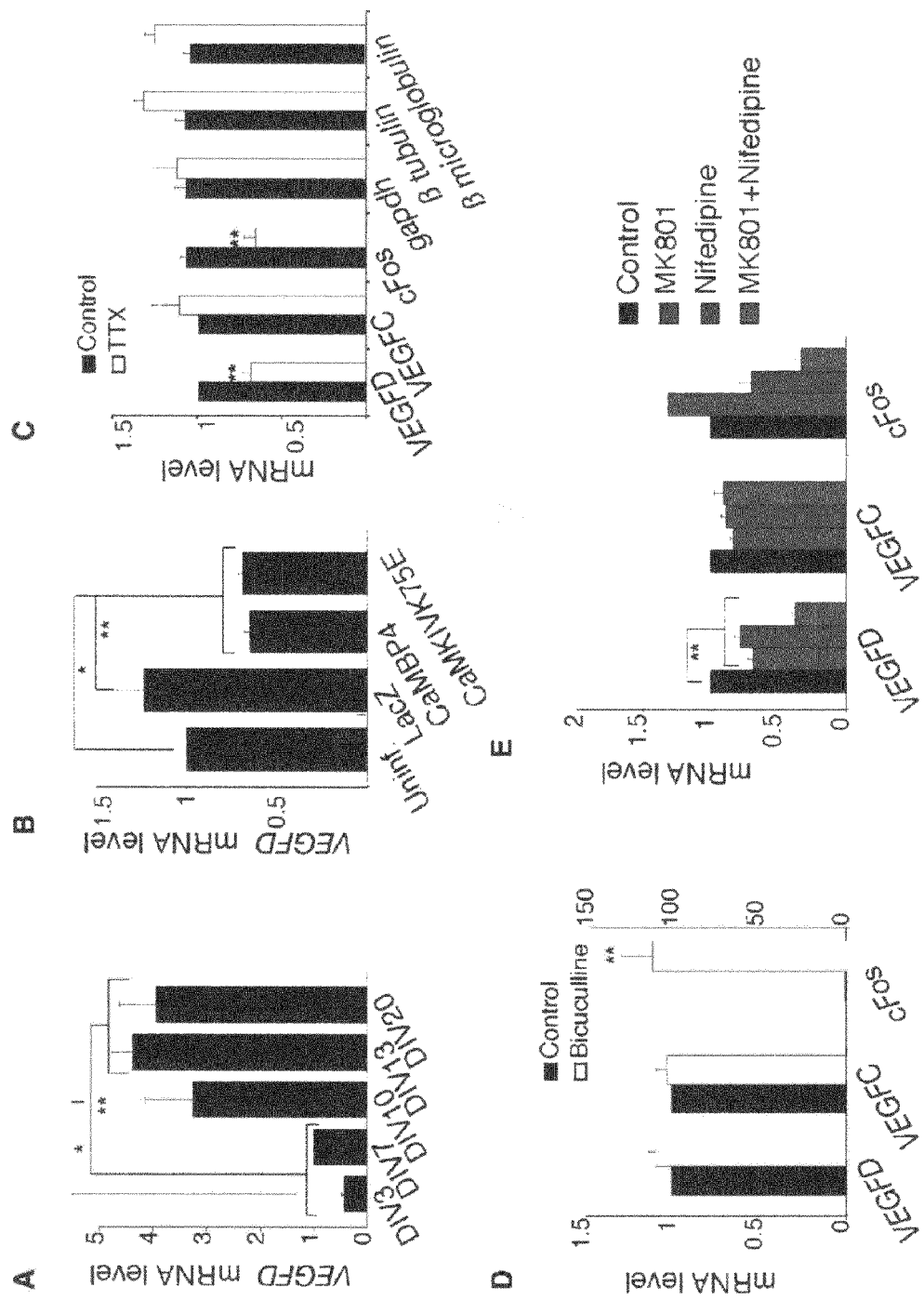
Figure 2 A to E

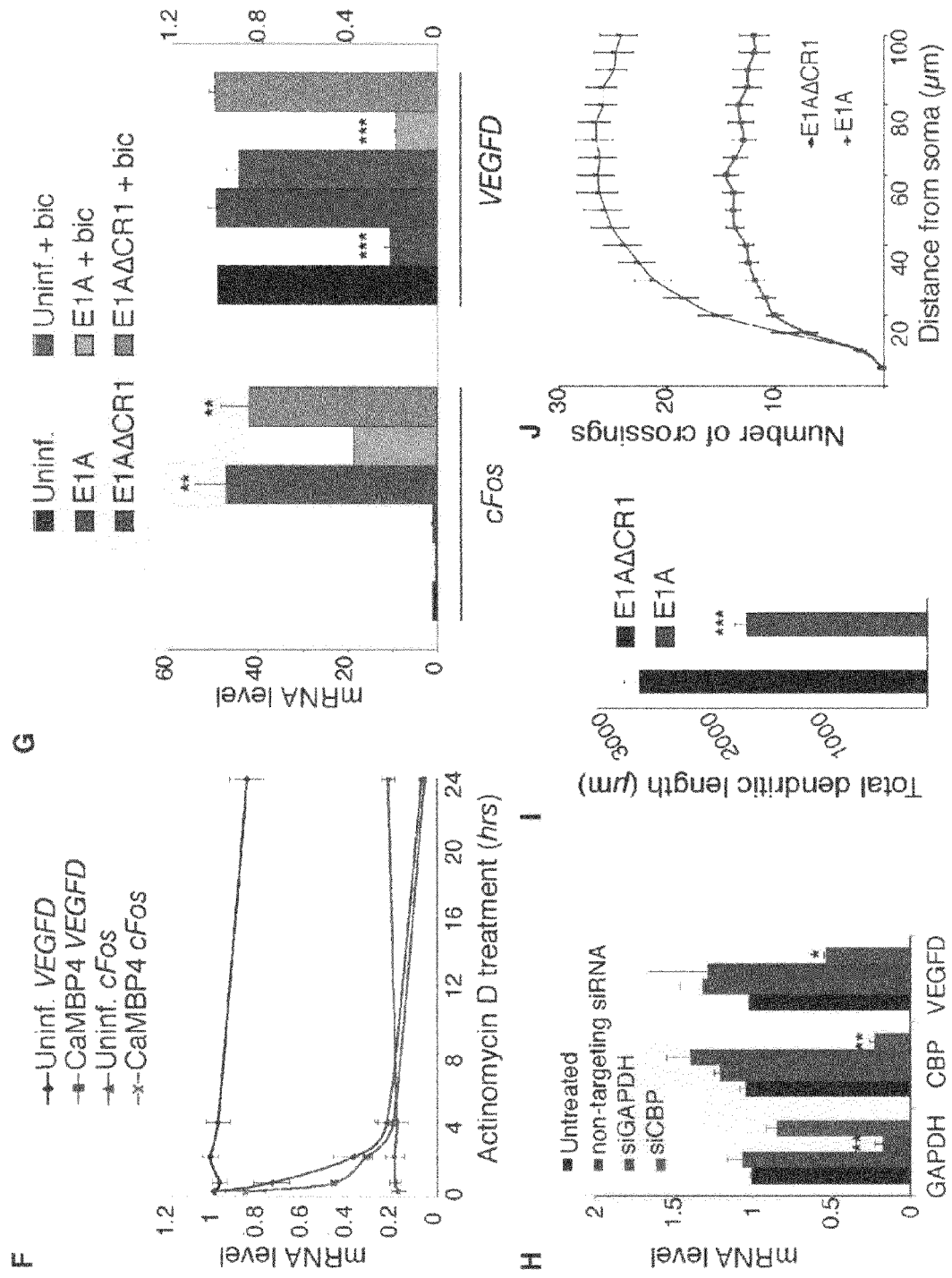
Figure 2 F to J

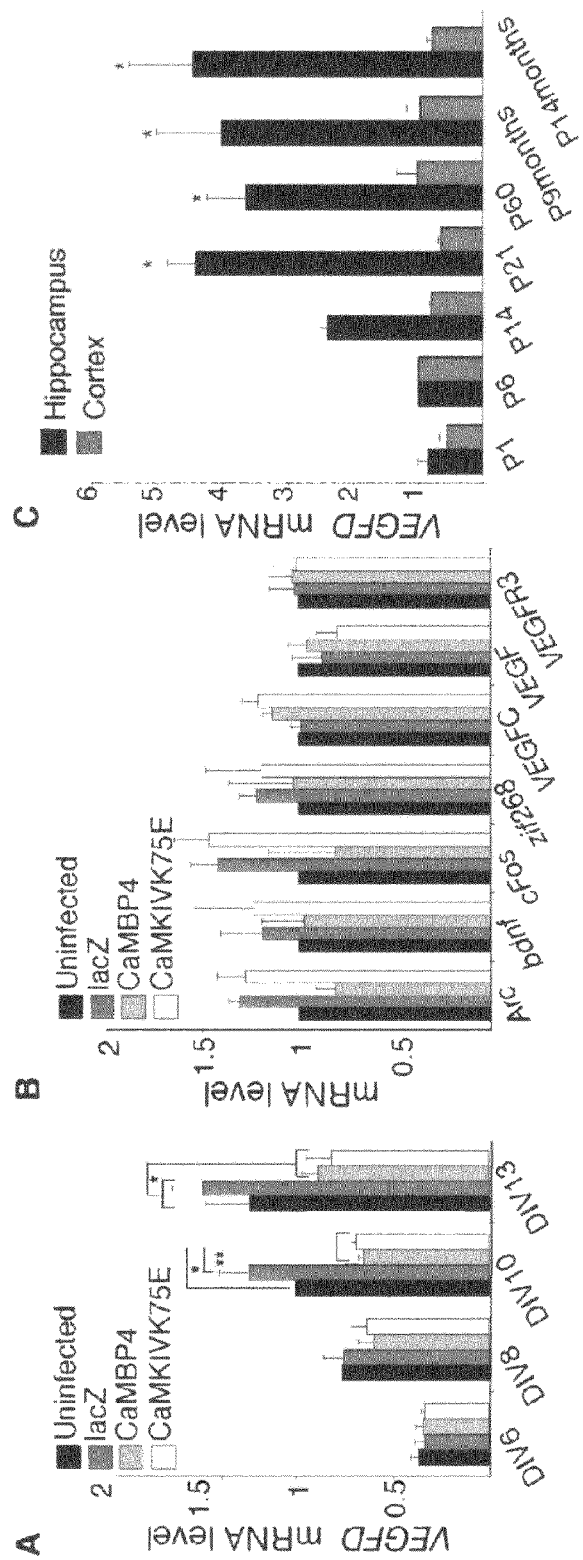
Figure 3 A to C

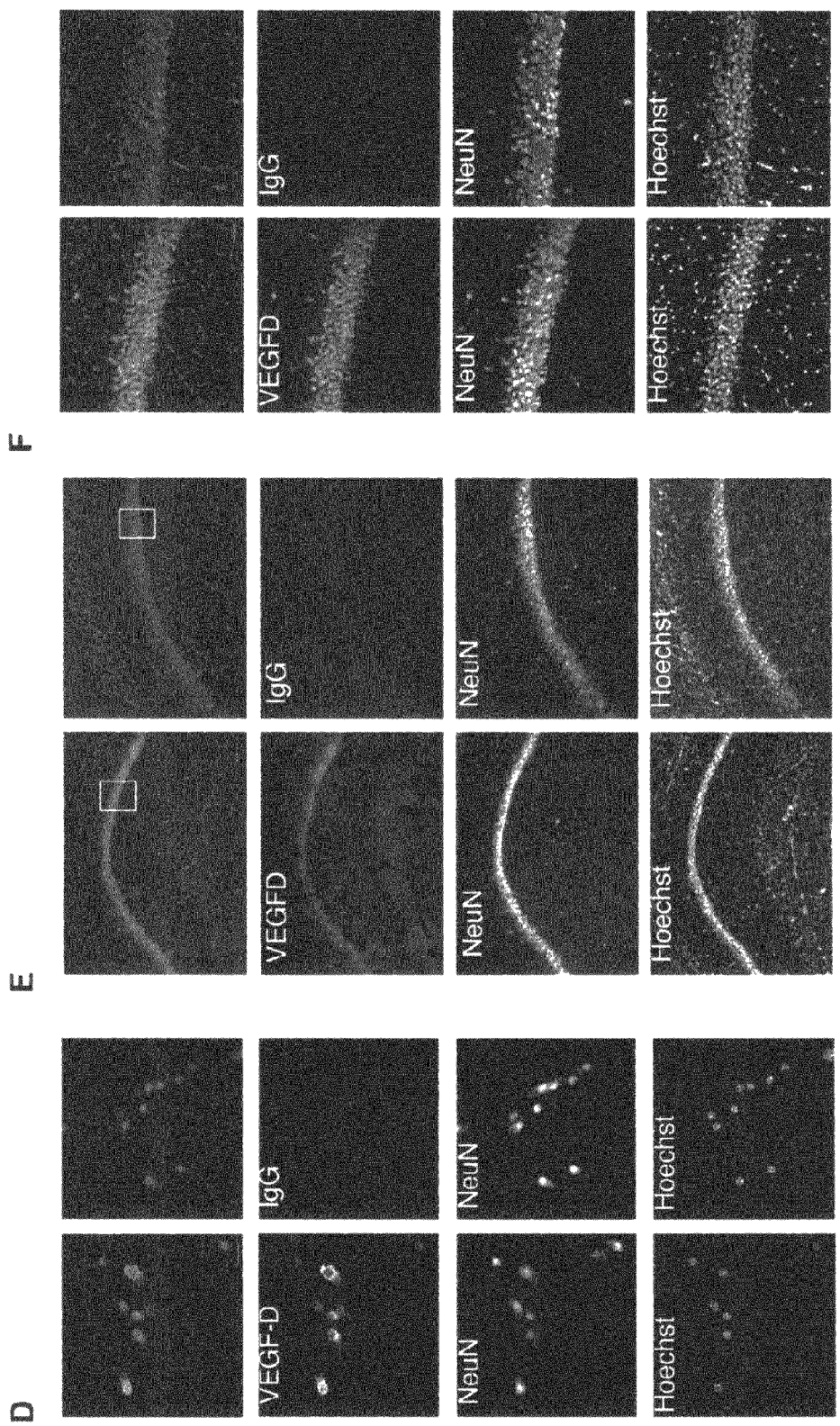
Figure 3 D to F

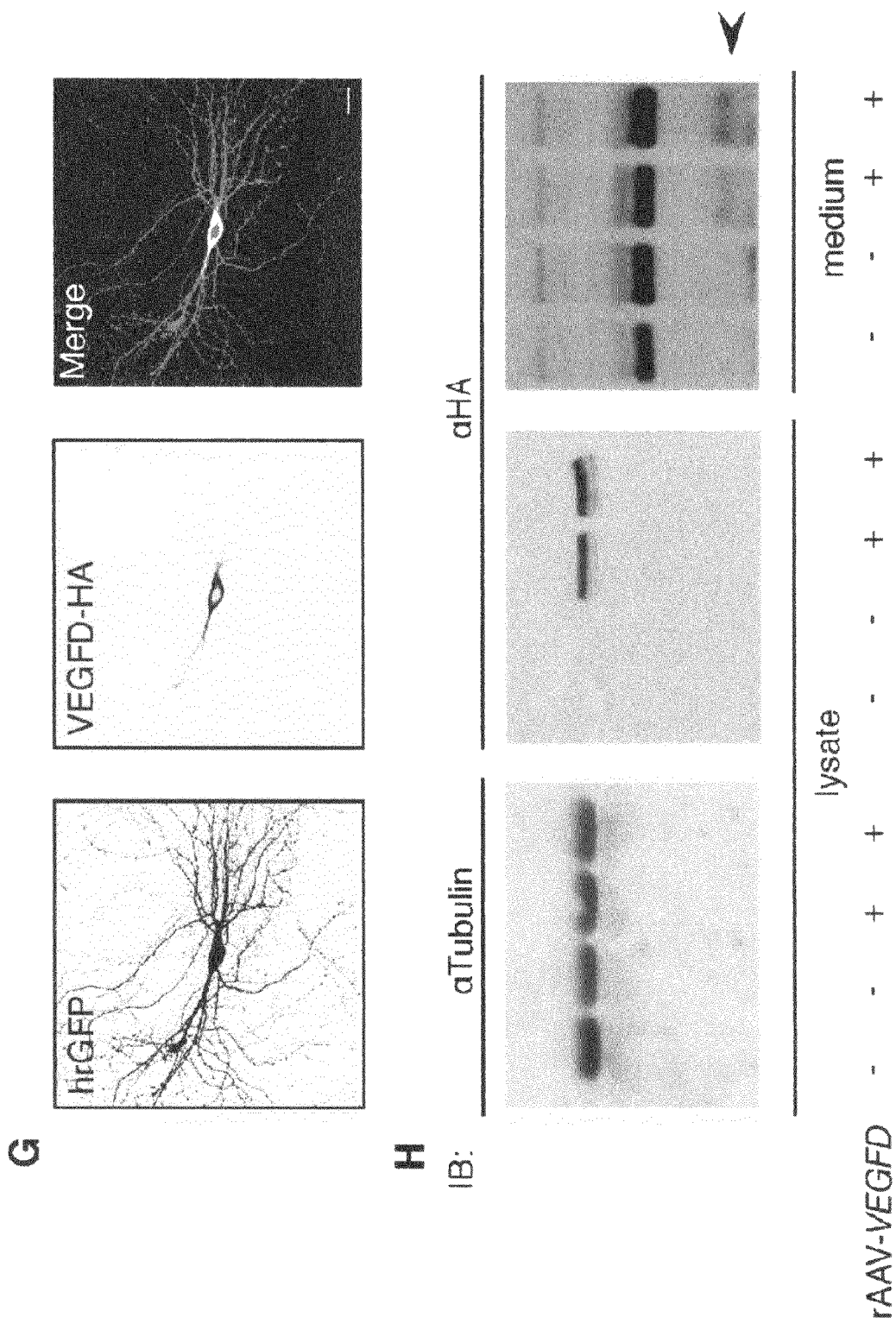
Figure 3 G, H

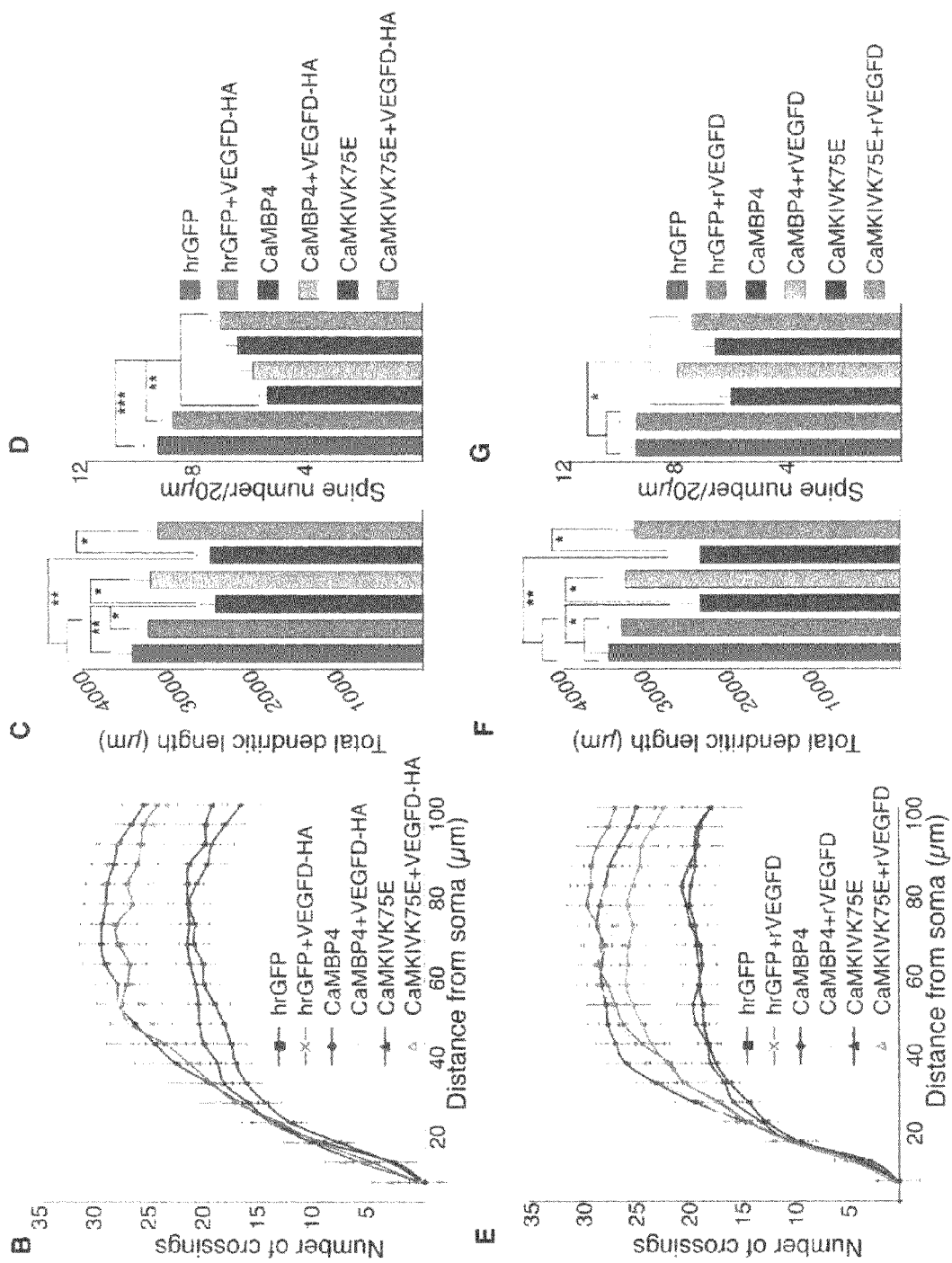
Figure 4 B to G

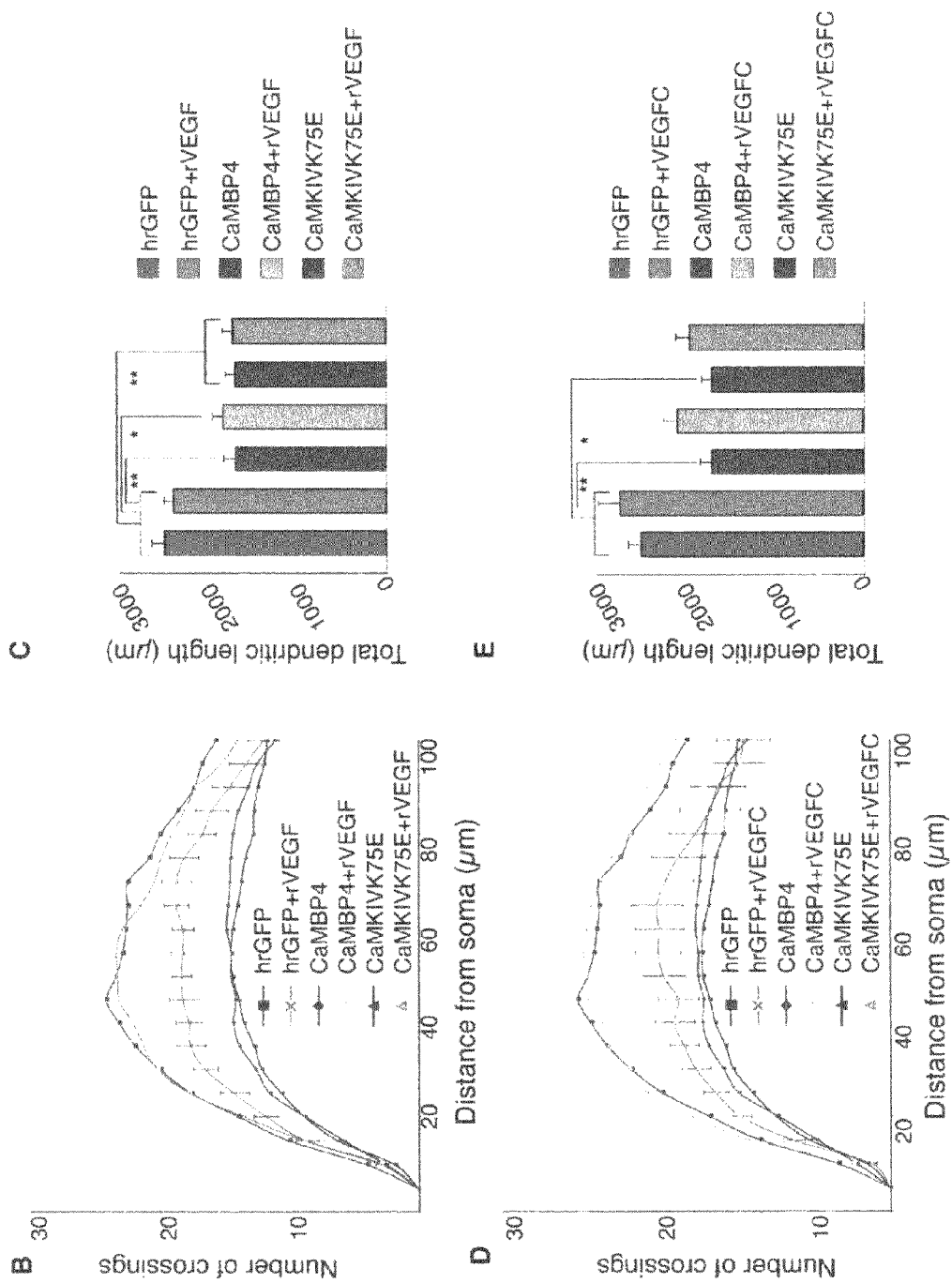
Figure 5 B to E

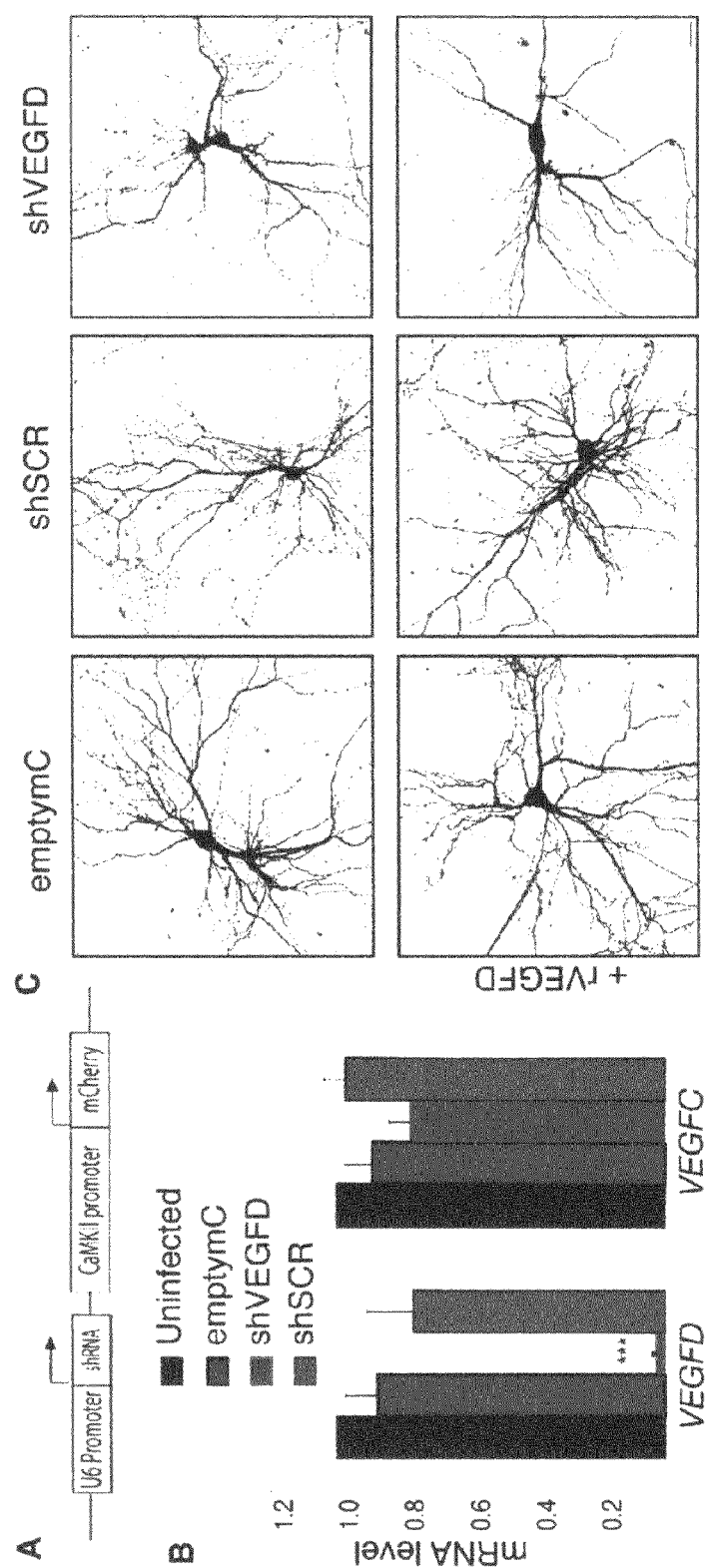
Figure 6 A to C

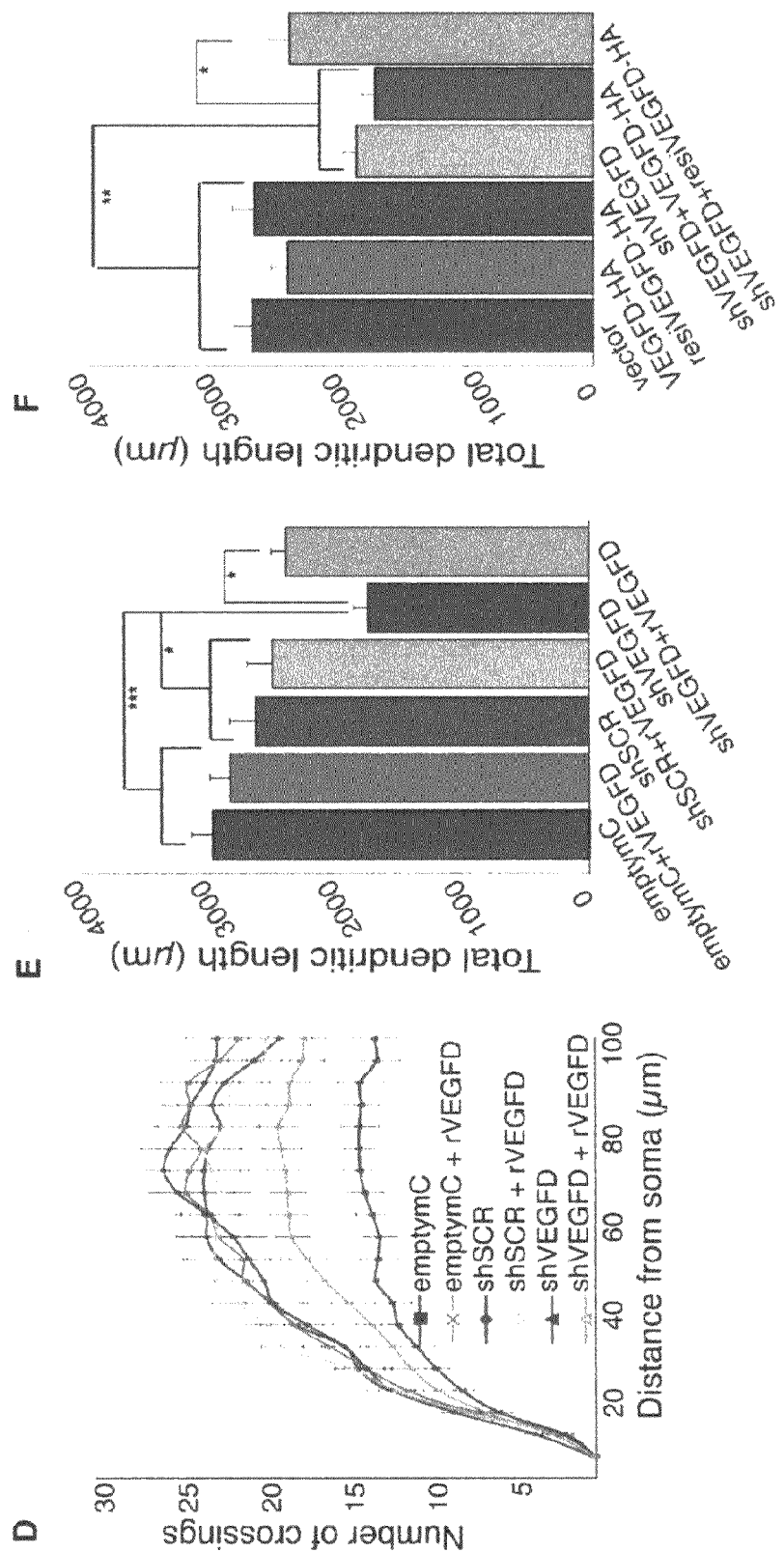
Figure 6 D to F

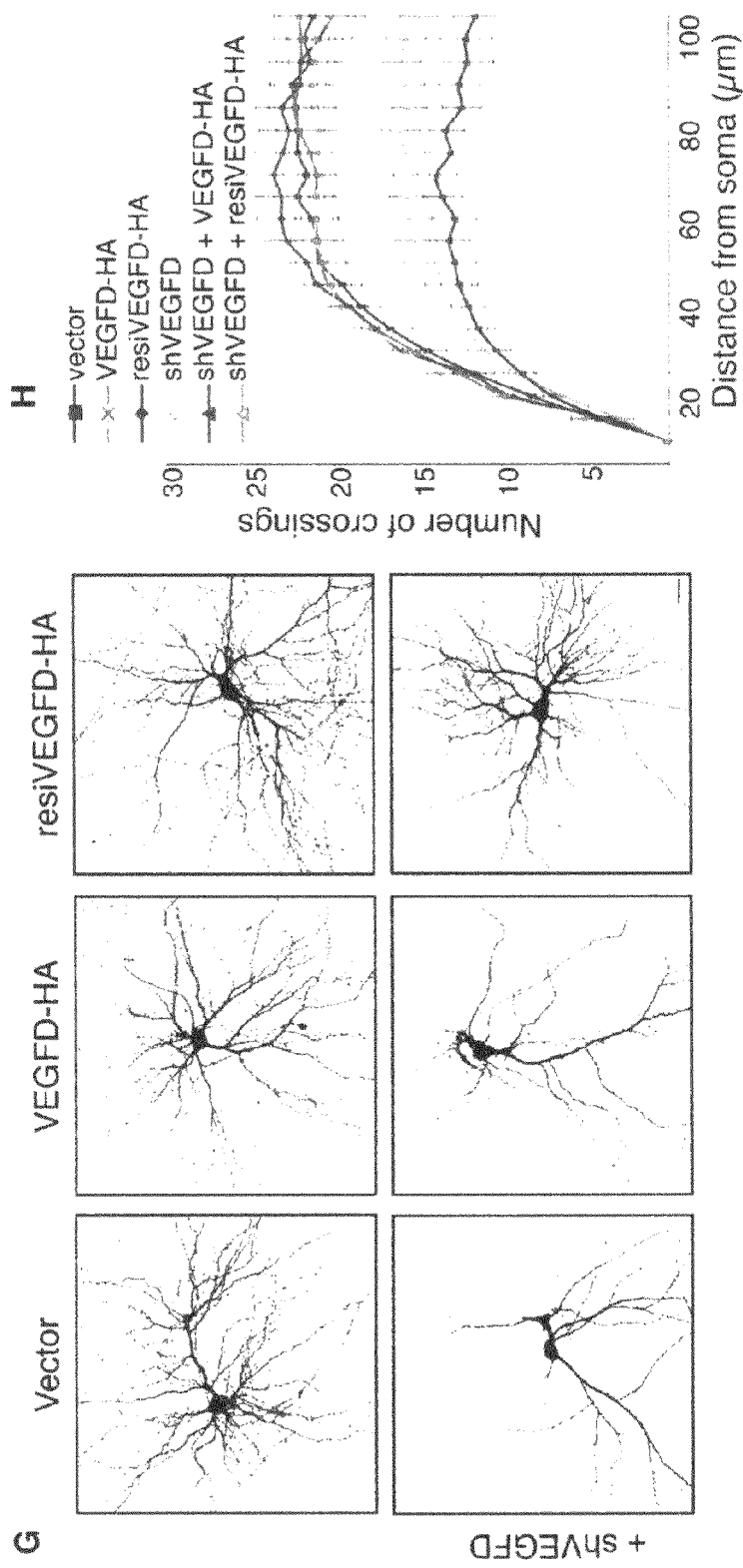
Figure 6 G, H

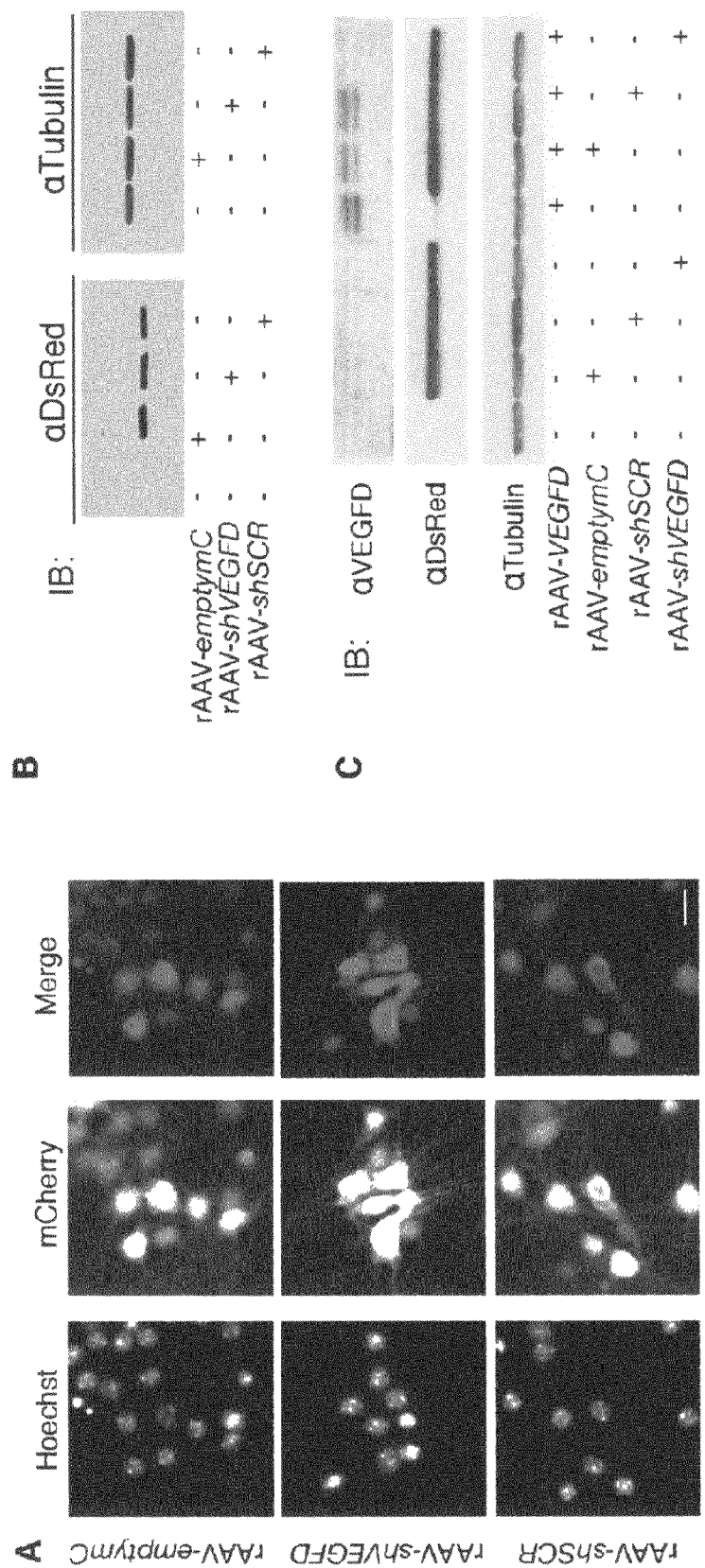
Figure 7 A to C

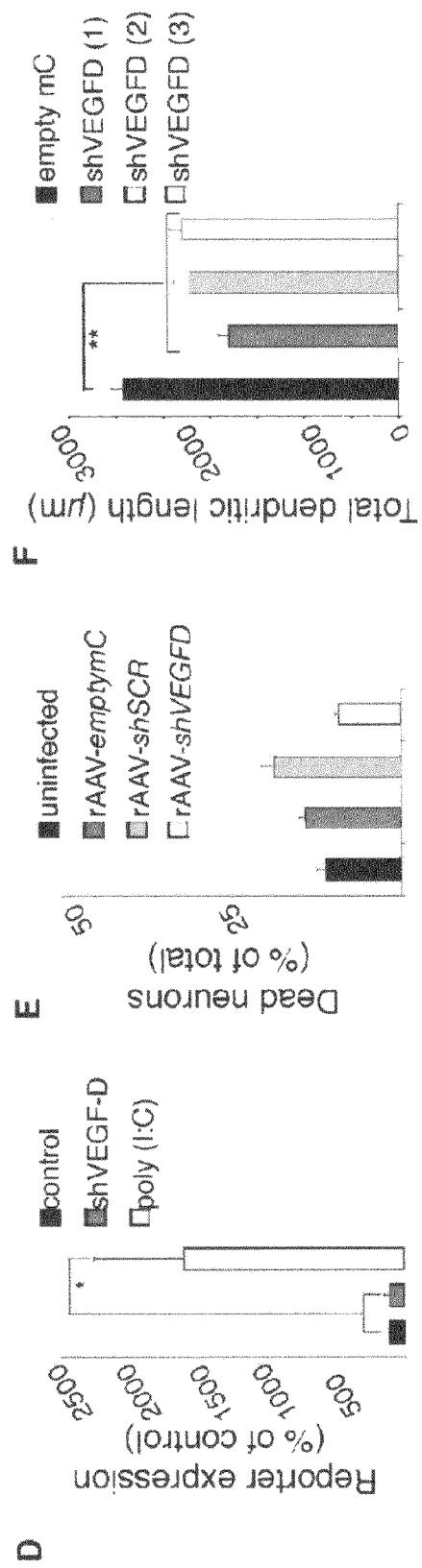
Figure 7 D to F

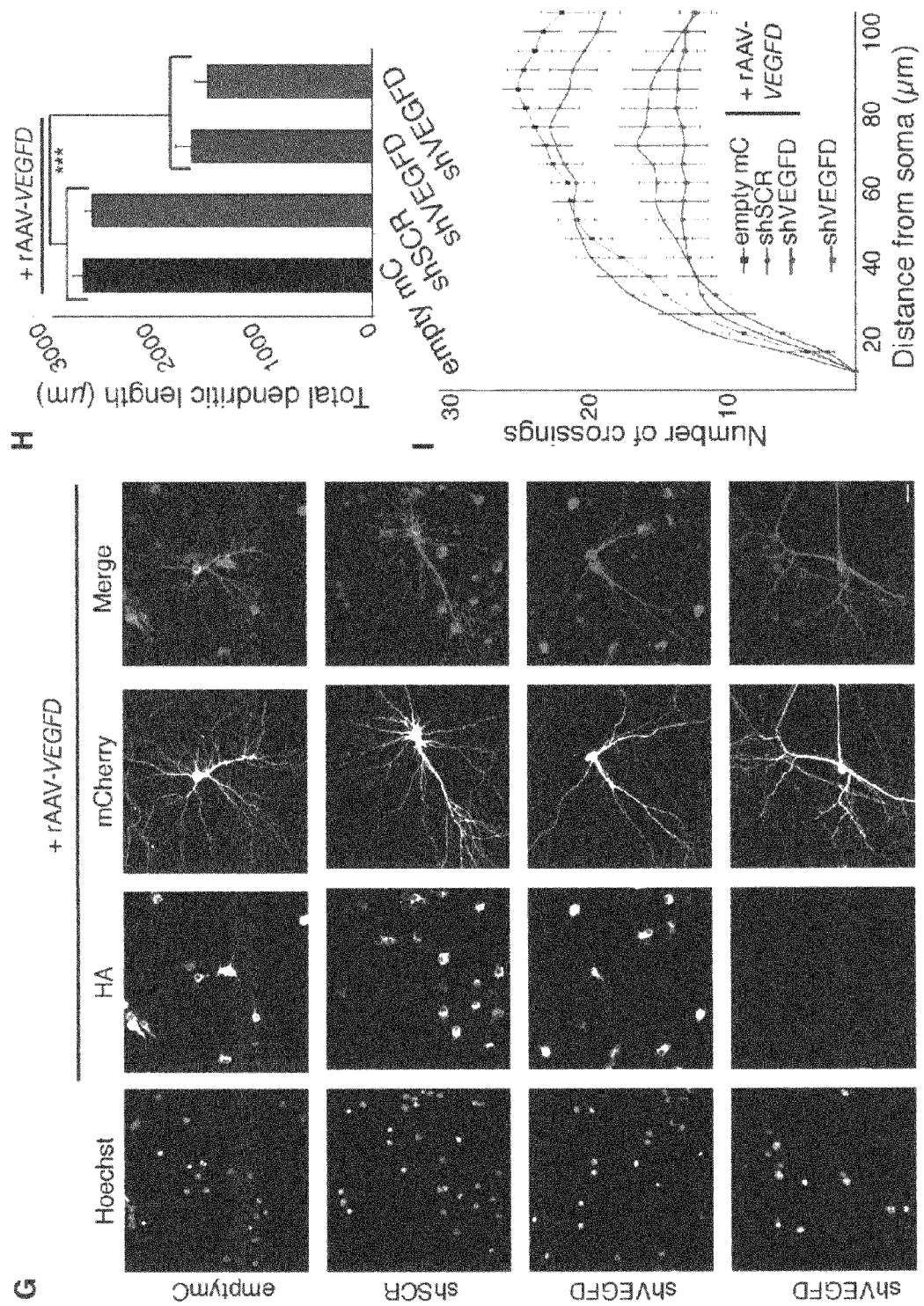
Figure 7 G to I

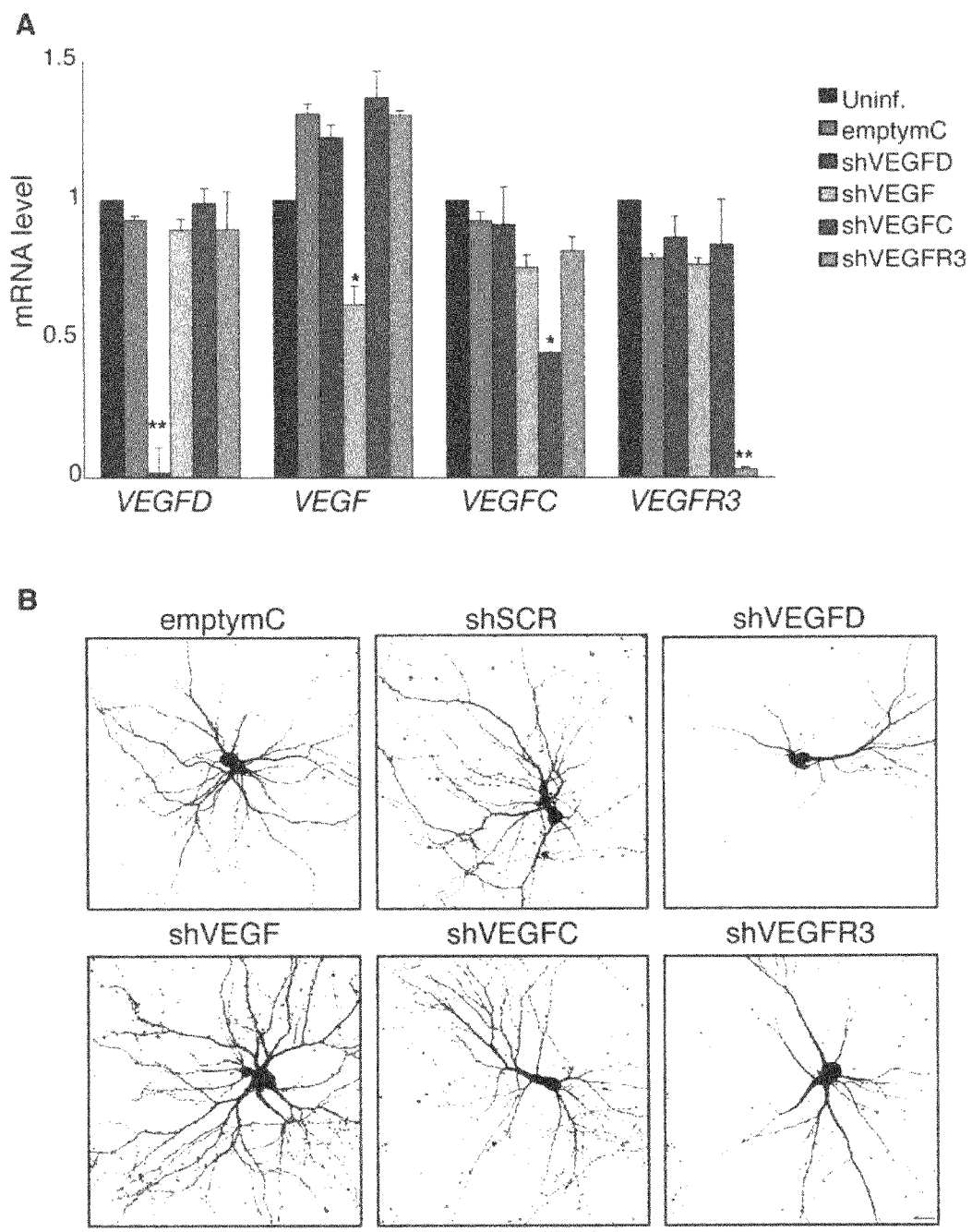
Figure 8 A, B

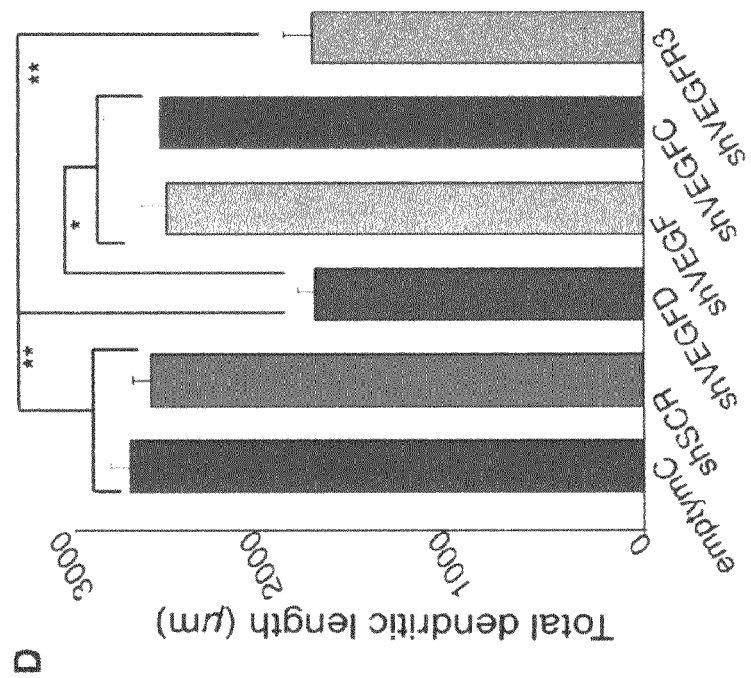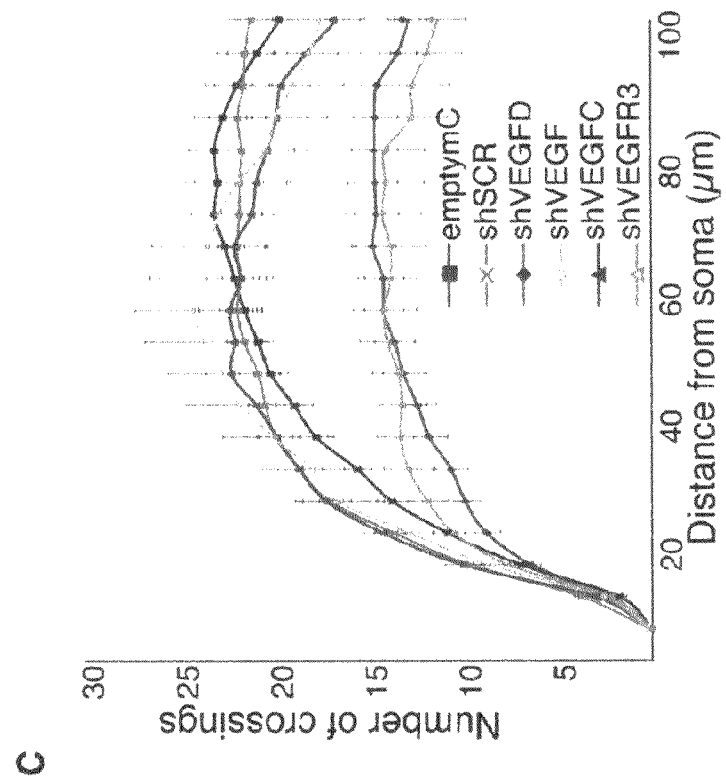
Figure 8 C, D

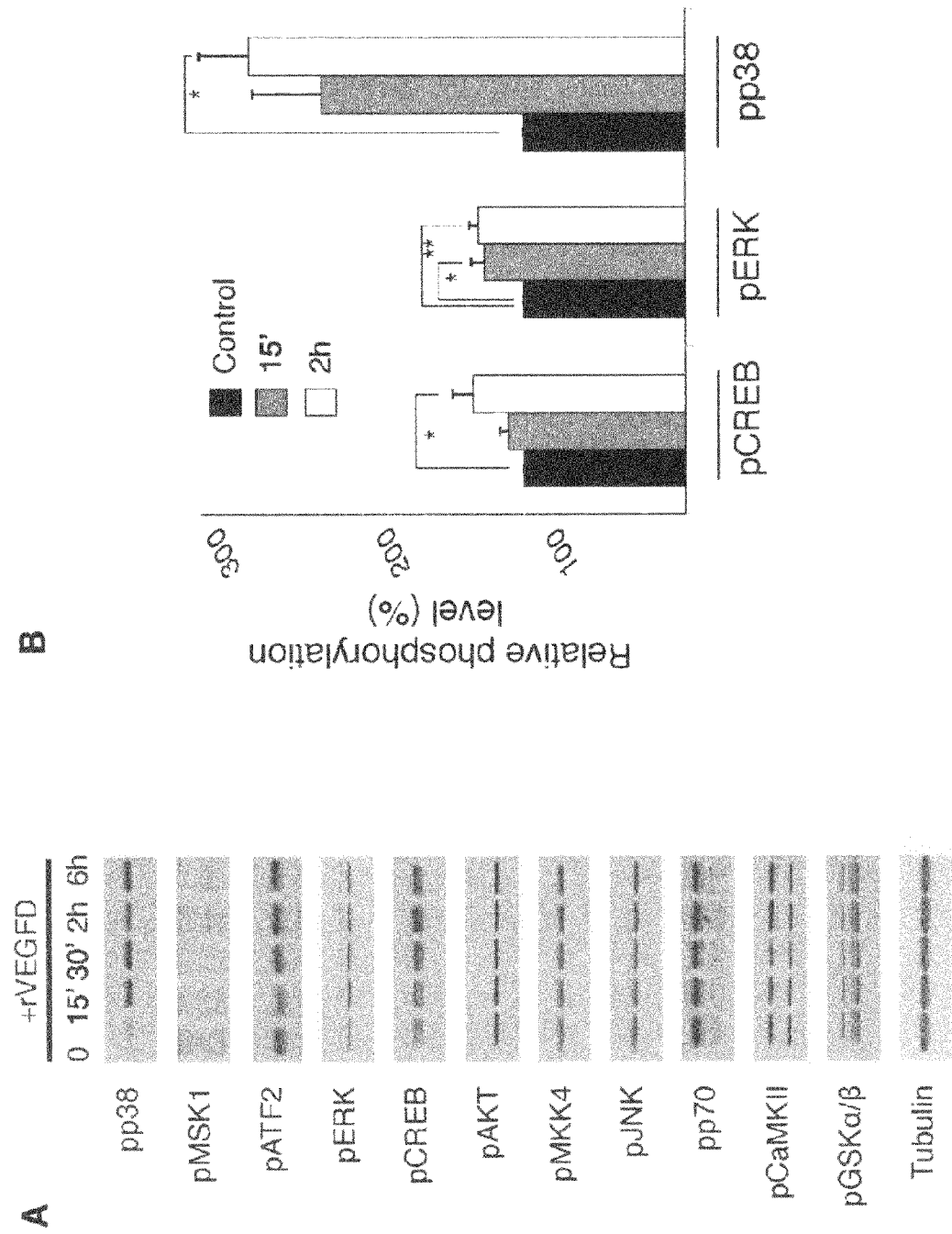
Figure 9 A, B

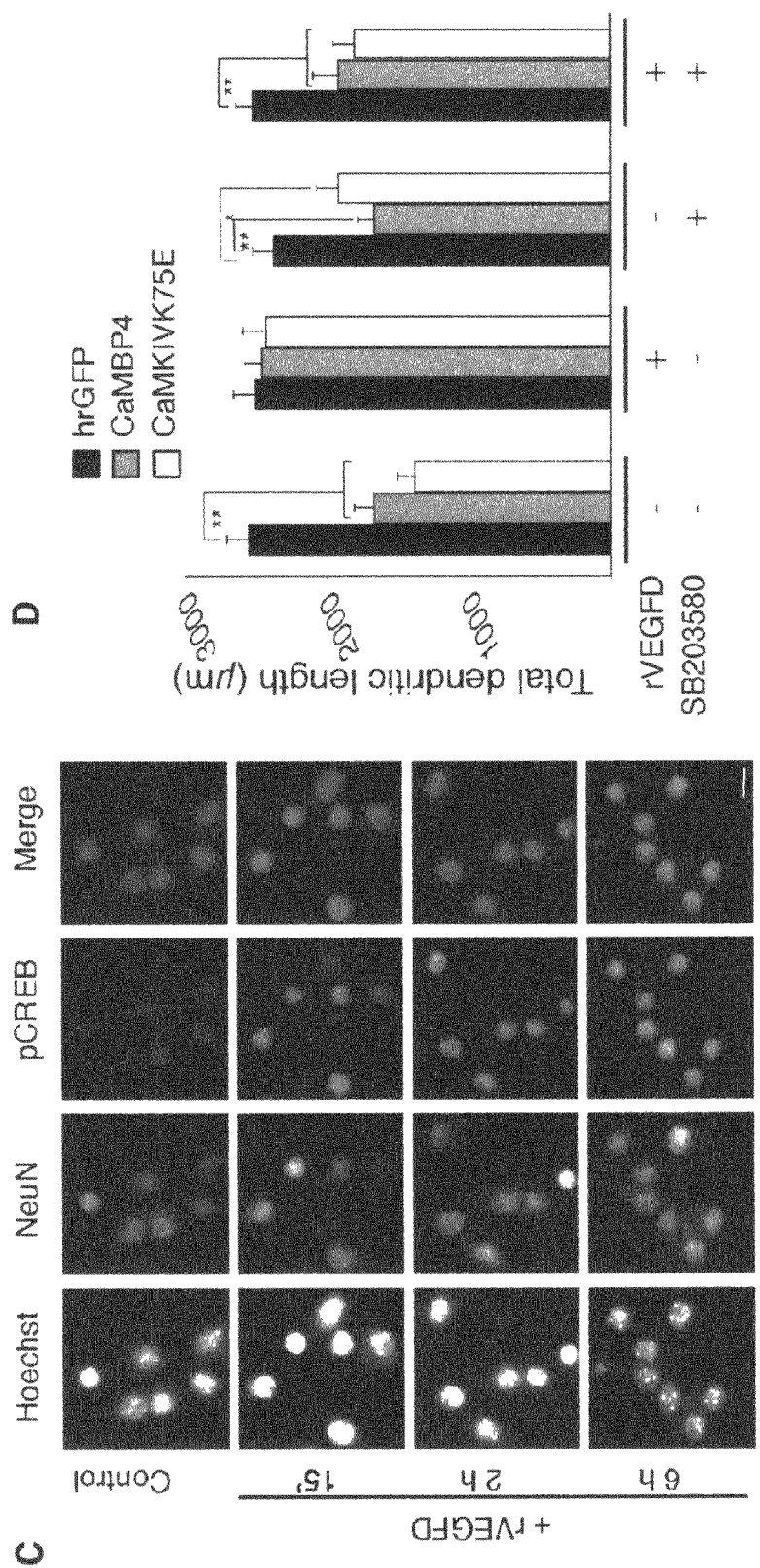
Figure 9 C, D

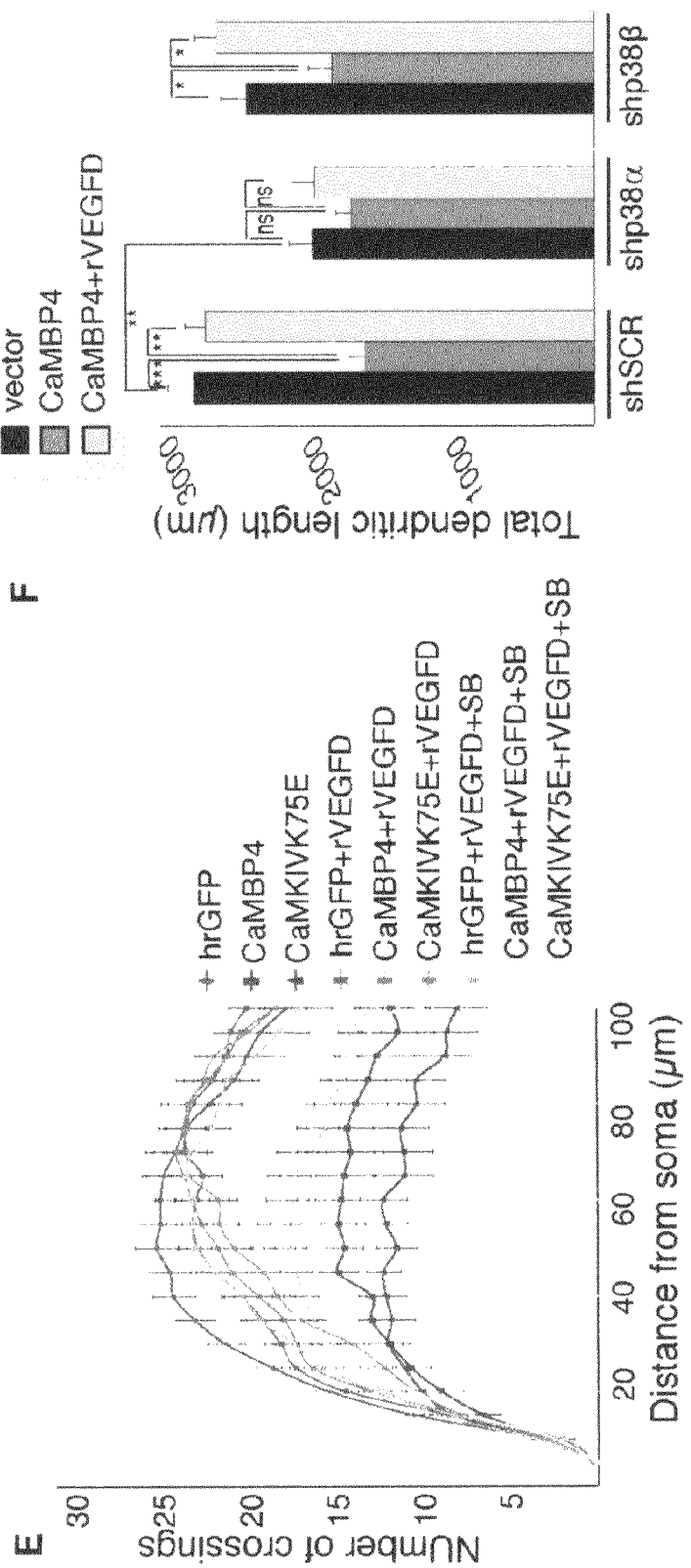
Figure 9 E, F

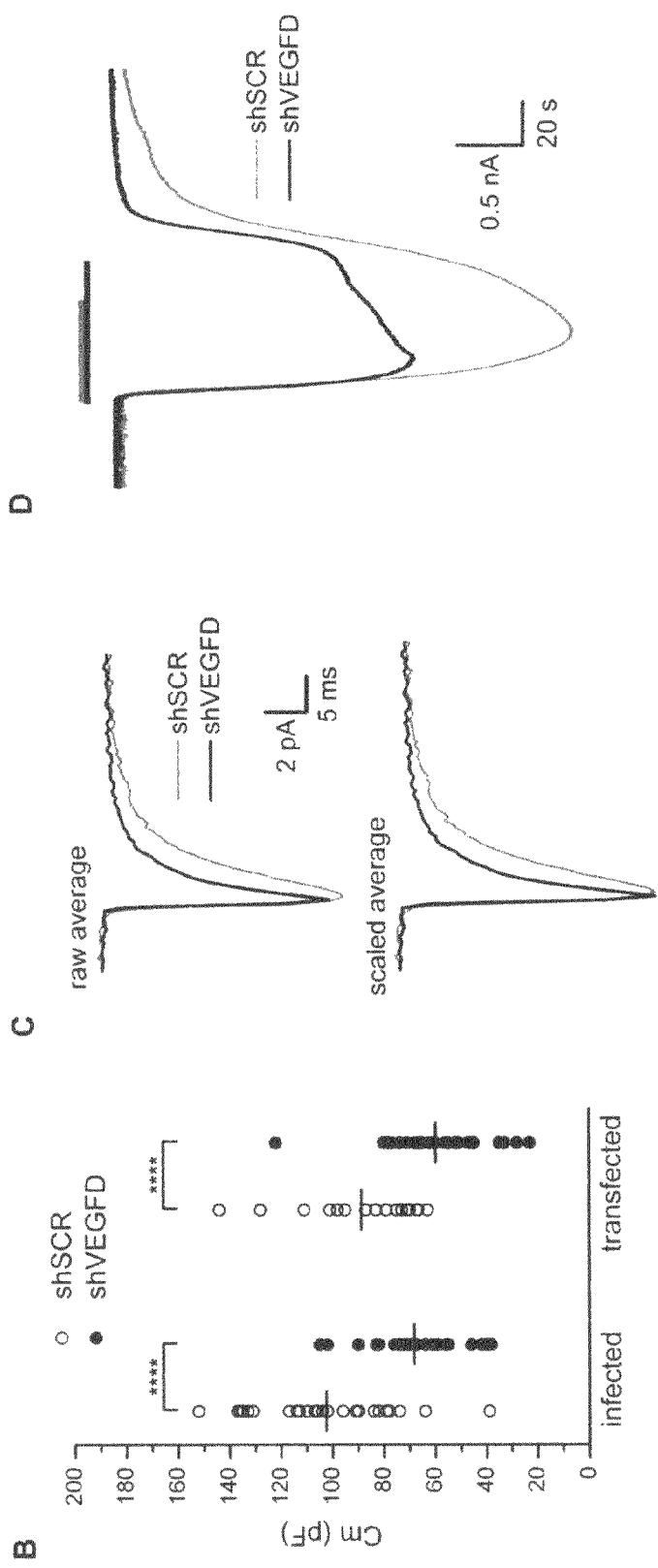
Figure 10 B to D

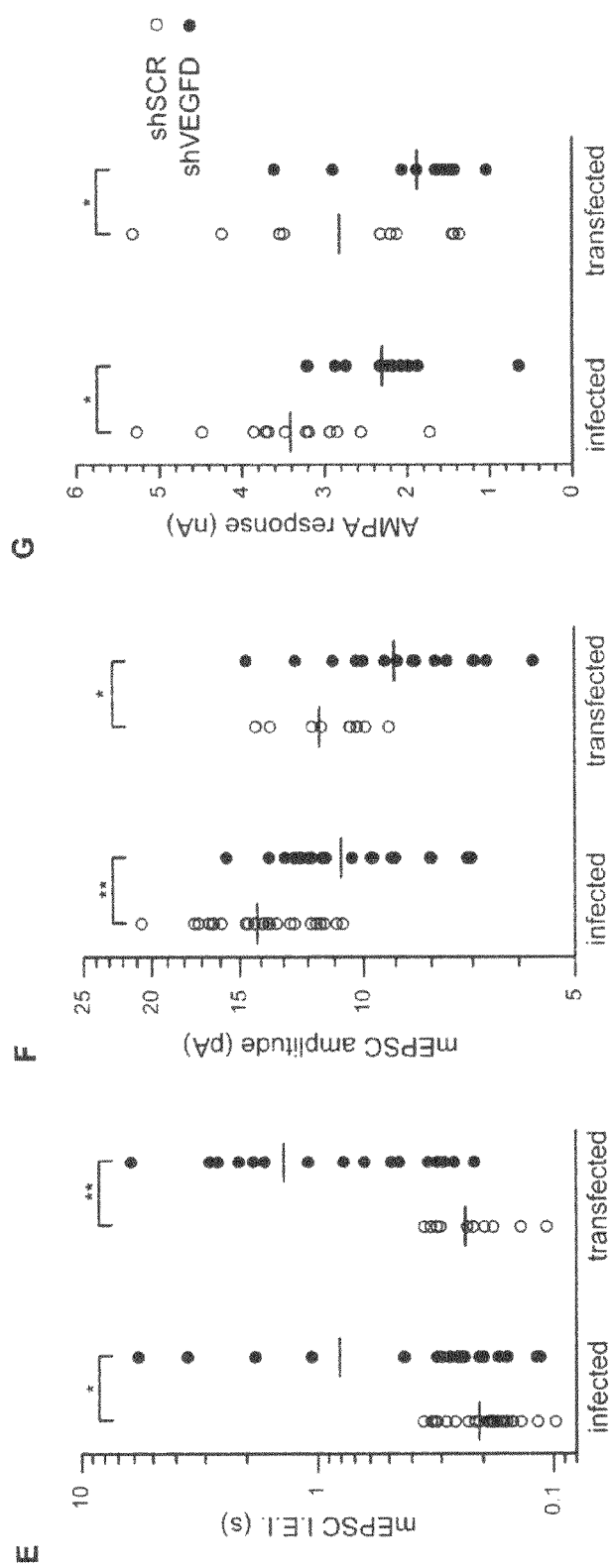
Figure 10 E to G

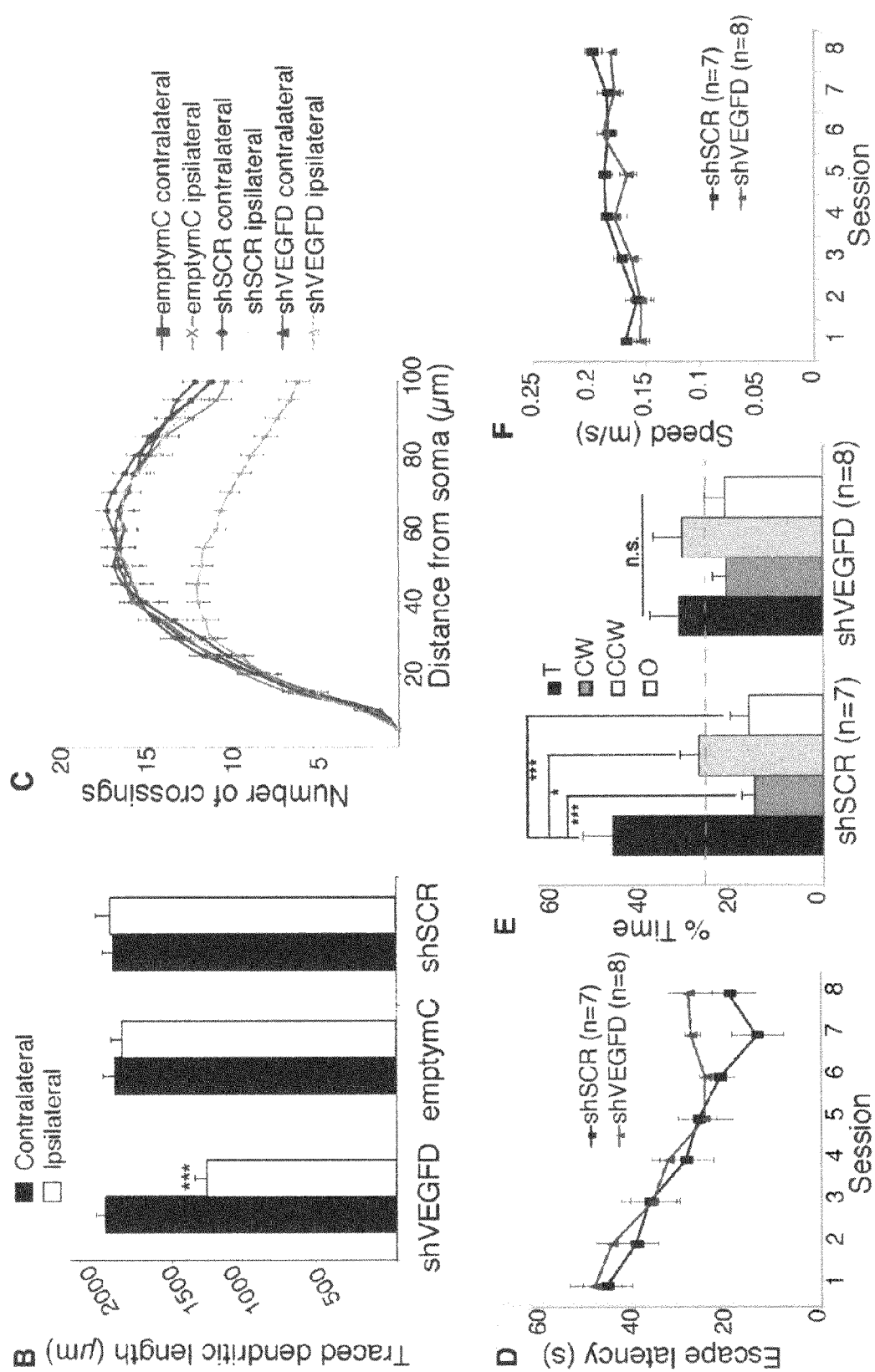
Figure 11 B to F

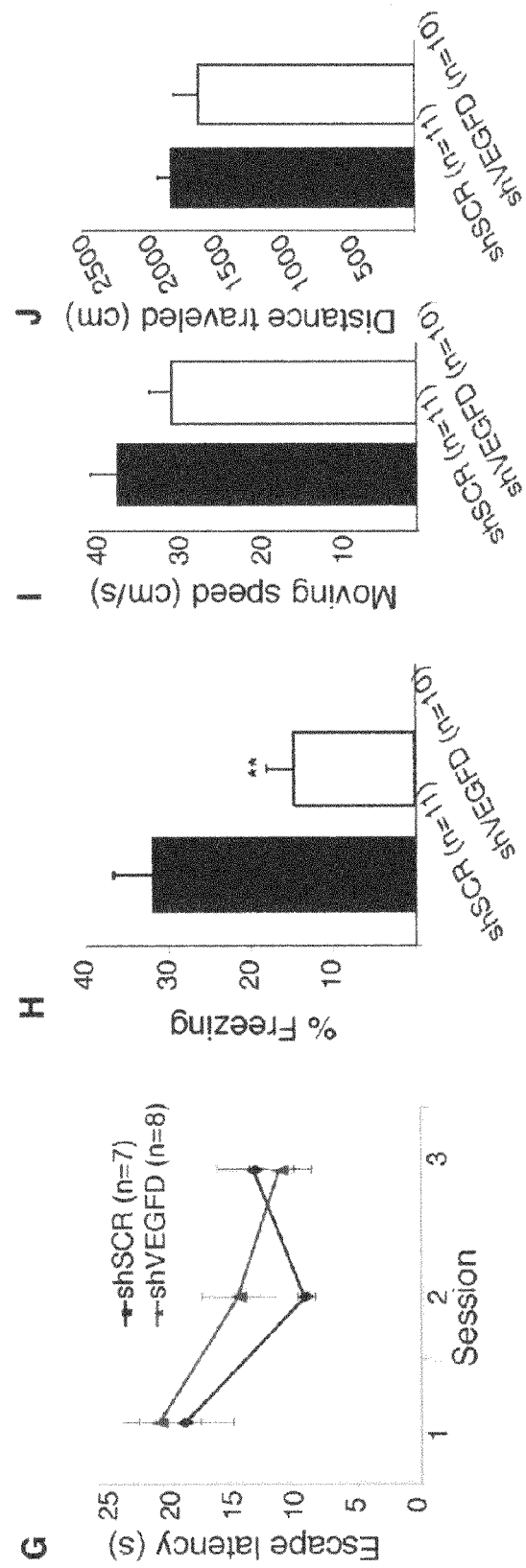
Figure 11 G to J

| PEPTIDE # | P38 | GSK | PEPTIDE # | efficacy on rec | bin | morpho | vegf-d | D | I | E | T | L | K | V | I | D | E | E | W | Q | R | T | Q | C | S |
|---|---|---|---|---|---|---|---|---|---|---|---|---|---|---|---|---|---|---|---|---|---|---|---|---|---|
| 38 | 174 | 100 | 38 | 0.77 | | | | Ac- | A | L | T | L | K | E | I | D | E | E | F | Q | R | K | G | I | -amid |
| 39 | 261 | 117 | 39 | 1.16 | + | | | Ac- | A | L | T | L | K | E | I | D | E | E | L | Q | R | K | G | I | -amid |
| 40 | 167 | 135 | 40 | 0.74 | | | | Ac- | A | L | T | L | K | E | I | D | E | E | L | Q | A | K | G | I | -amid |
| 41 | 228 | 132 | 41 | 1.01 | + | | | Ac- | A | L | T | L | K | E | I | D | E | E | W | Q | R | R | G | I | -amid |
| 42 | 358 | 126 | 42 | 1.58 | + | | | Ac- | A | L | T | L | K | E | I | D | E | E | W | D | R | N | G | I | -amid |
| 43 | 323 | 129 | 43 | 1.43 | + | | | Ac- | A | L | T | L | K | E | I | D | E | E | W | E | R | K | G | I | -amid |
| 44 | 223 | 119 | 44 | 0.99 | | | | Ac- | A | L | T | L | K | E | I | D | E | E | W | K | R | K | G | I | -amid |
| 45 | 230 | 103 | 45 | 1.02 | | | | Ac- | A | L | T | L | K | E | I | D | E | E | W | Q | K | K | G | I | -amid |
| 46 | 179 | 112 | 46 | 0.79 | | | | Ac- | A | L | T | L | K | E | I | D | E | E | W | Q | Q | K | G | I | -amid |
| 47 | 270 | 88 | 47 | 1.19 | + | | | Ac- | A | L | T | L | K | E | I | D | E | E | W | Q | W | K | G | I | -amid |
| 48 | 350 | 165 | 48 | 2.92 | ++ | | | Ac- | A | L | T | L | K | E | I | D | E | E | W | N | K | K | G | I | -amid |
| 49 | 397 | 183 | 49 | 3.30 | +++ | | | Ac- | A | L | T | L | K | E | I | D | E | E | W | Q | R | A | G | I | -amid |
| 51 | 239 | 76 | 51 | 1.99 | + | | | Ac- | A | L | T | L | K | E | I | D | E | E | W | Q | R | N | G | I | -amid |
| 52 | 197 | 115 | 52 | 1.64 | ++ | | | Ac- | A | L | T | L | K | E | I | D | E | E | W | R | R | G | G | I | -amid |
| 53 | 293 | 146 | 53 | 2.44 | +++ | | | Ac- | A | L | T | L | K | E | I | D | E | E | W | Q | R | R | G | I | -amid |
| 54 | 513 | 140 | 54 | 4.27 | ++++ | | | Ac- | A | L | T | L | K | E | I | D | E | E | W | Q | Q | G | I | -amid |
| 55 | 197 | 116 | 55 | 1.64 | + | | | Ac- | A | L | T | L | K | E | I | D | E | E | W | Q | R | K | V | I | -amid |
| 56 | 590 | 132 | 56 | 4.92 | ++++ | | | Ac- | A | L | T | L | K | E | I | D | E | E | W | Q | R | K | G | V | -amid |
| 57 | 110 | 51 | 57 | 0.92 | | | | Ac- | A | L | T | L | K | E | I | D | E | E | W | Q | R | K | V | I | -amid |
| 58 | 250 | 72 | 58 | 2.08 | + | | | Ac- | A | L | T | L | K | E | I | D | E | E | W | Q | R | K | G | V | -amid |
| 59 | 260 | 123 | 59 | 2.08 | ++ | | | Ac- | A | L | T | L | K | E | I | D | E | E | W | Q | R | K | G | F | -amid |
| 60 | 349 | 118 | 60 | 2.79 | | | | Ac- | A | L | T | L | K | E | I | D | E | E | W | Q | R | K | G | L | -amid |
| 61 | 98 | 87 | 61 | 0.78 | | | | Ac- | A | L | T | L | K | E | I | D | E | E | W | Q | R | K | G | I | -amid |
| 62 | 94 | 83 | 62 | 0.75 | | | | alt L | T | L | K | E | I | D | E | E | W | Q | R | K | G | I | -amid |
| 64 | 140 | 84 | 64 | 1.12 | | | | Ac- | A | alt T | L | K | E | I | D | E | E | W | Q | R | K | G | I | -amid |
| 65 | 349 | 122 | 65 | 2.79 | ++ | | | Ac- | A | L | alt L | K | E | I | D | E | E | W | Q | R | K | G | I | -amid |
| 66 | 188 | 81 | 66 | 1.50 | + | | | Ac- | A | L | T | alt K | E | I | D | E | E | W | Q | R | K | G | I | -amid |
| 67 | 214 | 92 | 67 | 1.71 | + | | | Ac- | A | L | T | L | alt E | I | D | E | E | W | Q | R | K | G | I | -amid |
| 68 | 413 | 135 | 68 | 3.30 | +++ | | | Ac- | A | L | T | L | K | alt I | D | E | E | W | Q | R | K | G | I | -amid |
| 69 | 392 | 93 | 69 | 3.14 | +++ | | | Ac- | A | L | T | L | K | E | alt D | E | E | W | Q | R | K | G | I | -amid |
| 70 | 314 | 111 | 70 | 1.83 | + | | | Ac- | A | L | T | L | K | E | I | alt E | E | W | Q | R | K | G | I | -amid |
| 71 | 266 | 93 | 71 | 1.55 | + | | | Ac- | A | L | T | L | K | E | I | D | alt E | W | Q | R | K | G | I | -amid |
| 72 | 87 | 75 | 72 | 0.50 | | | | Ac- | A | L | T | L | K | E | I | D | E | alt W | Q | R | K | G | I | -amid |
| 73 | 215 | 106 | 73 | 1.25 | + | | | Ac- | A | L | T | L | K | E | I | D | E | E | alt Q | R | K | G | I | -amid |
| 74 | 203 | 95 | 74 | 1.18 | + | | | Ac- | A | L | T | L | K | E | I | D | E | E | W | alt R | K | G | I | -amid |
| 75 | 236 | 108 | 75 | 1.37 | + | | | Ac- | A | L | T | L | K | E | I | D | E | E | W | Q | alt K | G | I | -amid |
| 76 | 210 | 120 | 76 | 1.22 | + | | | Ac- | A | L | T | L | K | E | I | D | E | E | W | Q | R | alt G | I | -amid |
| 77 | 214 | 108 | 77 | 1.24 | + | | | Ac- | A | L | T | L | K | E | I | D | E | E | W | Q | R | K | alt I | -amid |
| 78 | 137 | 78 | 78 | 0.80 | | | | Ac- | A | L | T | L | K | E | I | D | E | E | W | Q | R | K | G | alt I | -amid |
| 79 | 222 | 112 | 79 | 1.29 | + | | | gpL | K | E | I | D | E | E | W | Q | R | K | G | I | alt A | -amid |

Figure 13 C

```
                        SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: DNA coding for an shRNA

<400> SEQUENCE: 1
gggcttcagg agcgaacat                                           19

<210> SEQ ID NO 2
<211> LENGTH: 19
<212> TYPE: DNA
<213> ORGANISM: Artificial Sequence
<220> FEATURE:
<223> OTHER INFORMATION: DNA coding for an shRNA

<400> SEQUENCE: 2
gtgccaagac gggtagtca                                           19

<210> SEQ ID NO 3
<211> LENGTH: 21
<212> TYPE: DNA
<213> ORGANISM: Artificial Sequence
<220> FEATURE:
<223> OTHER INFORMATION: DNA coding for an shRNA

<400> SEQUENCE: 3
aaacacgaaa atgtgattgg t                                        21

<210> SEQ ID NO 4
<211> LENGTH: 21
<212> TYPE: DNA
<213> ORGANISM: Artificial Sequence
<220> FEATURE:
<223> OTHER INFORMATION: DNA coding for an shRNA

<400> SEQUENCE: 4
aagcacgaga acgtcatagg a                                        21

<210> SEQ ID NO 5
<211> LENGTH: 19
<212> TYPE: DNA
<213> ORGANISM: Artificial Sequence
<220> FEATURE:
<223> OTHER INFORMATION: DNA coding for an shRNA

<400> SEQUENCE: 5
acctcaccaa agccagcac                                           19

<210> SEQ ID NO 6
<211> LENGTH: 19
<212> TYPE: DNA
<213> ORGANISM: Artificial Sequence
<220> FEATURE:
<223> OTHER INFORMATION: DNA coding for an shRNA
```

-continued

<400> SEQUENCE: 6
gttcattcca ttattagac                                                                                  19

<210> SEQ ID NO 7
<211> LENGTH: 21
<212> TYPE: DNA
<213> ORGANISM: Artificial Sequence
<220> FEATURE:
<223> OTHER INFORMATION: DNA coding for an shRNA

<400> SEQUENCE: 7
cccagtattg tgtggtacaa a                                                                              21

<210> SEQ ID NO 8
<211> LENGTH: 55
<212> TYPE: PRT
<213> ORGANISM: Artificial Sequence
<220> FEATURE:
<223> OTHER INFORMATION: Vascular endothelial growth factor receptor
      (VEGFR)-binding peptide

<400> SEQUENCE: 8

Ser Met Asp Ser Arg Ser Ala Ser His Arg Ser Thr Arg Phe Ala Ala
1               5                   10                  15

Thr Phe Tyr Asp Thr Glu Thr Leu Lys Val Ile Asp Glu Glu Trp Gln
            20                  25                  30

Arg Thr Gln Cys Ser Pro Arg Glu Thr Cys Val Glu Val Ala Ser Glu
        35                  40                  45

Leu Gly Lys Thr Thr Asn Thr
    50                  55

<210> SEQ ID NO 9
<211> LENGTH: 16
<212> TYPE: PRT
<213> ORGANISM: Artificial Sequence
<220> FEATURE:
<223> OTHER INFORMATION: Vascular endothelial growth factor receptor
      (VEGFR)-binding peptide

<400> SEQUENCE: 9

Ala Leu Ala Leu Lys Glu Ile Asp Glu Glu Trp Gln Arg Lys Gly Ile
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Vascular endothelial growth factor receptor
      (VEGFR)-binding peptide

<400> SEQUENCE: 10

Ala Leu Thr Leu Lys Glu Ala Asp Glu Glu Trp Gln Arg Lys Gly Ile
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Vascular endothelial growth factor receptor
      (VEGFR)-binding peptide

<400> SEQUENCE: 11

```
Ala Leu Thr Leu Lys Glu Ile Asp Glu Glu Trp Gln Arg Lys Gly Val
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Vascular endothelial growth factor receptor
      (VEGFR)-binding peptide

<400> SEQUENCE: 12

Ala Leu Thr Leu Lys Glu Ile Asp Glu Glu Trp Gln Arg Lys Gly Gly
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Vascular endothelial growth factor receptor
      (VEGFR)-binding peptide
<220> FEATURE:
<221> NAME/KEY: misc_feature
<222> LOCATION: (3)..(3)
<223> OTHER INFORMATION: Xaa denotes amino-isobutyric acid

<400> SEQUENCE: 13

Ala Leu Xaa Leu Lys Glu Ile Asp Glu Glu Trp Gln Arg Lys Gly Ile
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Vascular endothelial growth factor receptor
      (VEGFR)-binding peptide
<220> FEATURE:
<221> NAME/KEY: misc_feature
<222> LOCATION: (7)..(7)
<223> OTHER INFORMATION: Xaa denotes amino-isobutyric acid

<400> SEQUENCE: 14

Ala Leu Thr Leu Lys Glu Xaa Asp Glu Glu Trp Gln Arg Lys Gly Ile
1               5                   10                  15
```

VEGF-D/VEGFR2/3-MEDIATED REGULATION OF DENDRITES

CROSS-REFERENCE

This application is a section 371 of International application no. PCT/EP2012/002333, filed Jun. 1, 2012 which claims priority from EP Patent application no. 11 004490.6, filed Jun. 1, 2011 and is a continuation-in-part of U.S. patent application Ser. No. 13/150,846, filed Jun. 1, 2011, now abandoned.

FIELD

The present invention relates to methods for modulating, i.e. increasing or decreasing, the length and/or the complexity of the dendrites of a neuronal cell by influencing the amount of vascular endothelial growth factor D (VEGFD)-related signaling. The present invention further relates to methods for treating age- and/or disease-related cognitive dysfunctions, or for impairing the memory of a subject. Finally, the present invention relates to recombinant VEGFD (rVEGFD) for use in the treatment of age- and/or disease-related cognitive dysfunctions.

BACKGROUND

Many brain functions, including memory formation and acquired neuroprotection, are controlled by transient increases in the intracellular calcium concentration induced by synaptic activity. Calcium can act locally near the site of entry to switch on signaling mechanisms that modulate several biochemical processes that in turn lead to changes in neuronal excitability and/or the efficacy of synaptic transmission. The long-term maintenance of such activity-induced, functional adaptations requires that calcium transients invade the cell nucleus and activate or repress gene expression. Nuclear calcium is one of the most potent signals in neuronal gene expression and represents a key player in the dialogue between synapse and nucleus. It controls cAMP Response Element Binding (CREB)- and CREB-binding protein (CBP)-mediated transcription and is critical for the acquisition of memories and the build-up of neuroprotective activity in synaptically-activated neurons. A picture of how genomic events induced by nuclear calcium signaling regulate persistent neuroprotection is emerging. In contrast, nuclear calcium-regulated processes required for memory formation are unknown. Here, the possibility that nuclear calcium signaling modulates structural features of neurons, in particular the complexity of the dendritic arbor that determines their ability to receive and process inputs, was considered. The calcium/calmodulin dependent protein kinase IV (CaMKIV), a target of calcium in the nucleus, has been implicated in the regulation of dendritic growth and spine remodeling, suggesting that nuclear calcium may represent an important signal in these processes.

The role of neuronal dendrites is to receive and process synaptic inputs. The geometry of the dendritic arbor can undergo neuronal activity-dependent changes, which may impact on the cognitive abilities of the organism. The geometry of dendrites specifies the connectivity of neurons and strongly influences how signals are integrated and transmitted to the cell soma, and, therefore, also which output is produced. Changes in the lengths and branching patterns of dendrites would be expected to alter not only the performance of a neuron but also the computational power of the network the neuron is part of, ultimately causing changes in the organism's behavior.

Shortening and simplification of dendrites have been observed in a variety of disorders that are associated with mental retardation or cognitive deficits, including ischemia, in particular cerebral ischemia, genetic abnormalities, such as Down syndrome or Rett syndrome, neurodegenerative conditions, including Alzheimer's disease and ageing, metabolic dysfunctions and infection with human immunodeficiency virus (HIV).

Therefore, a strong need exists to provide means for modifying the length and/or the complexity of the dendrites of a neuronal cell, which could prove to be useful in the treatment of conditions that would benefit from such modification.

SUMMARY

This need is satisfied by providing the embodiments characterized in the claims.

In the present invention, vascular endothelial growth factor D (VEGFD), a mitogen for endothelial cells and regulator of angiogenesis and lymphatic vasculature, is identified as a target of nuclear calcium-CaMKIV signaling in hippocampal neurons. Further, it is shown that VEGFD is required for the maintenance of a complex dendritic arbor and provides the molecular link between neuronal activity, the regulation of dendritic geometry and cognitive functioning.

Accordingly, the present invention relates to a method for increasing at least one of the length and the complexity of the dendrites of a neuronal cell, comprising administering recombinant VEGFD (rVEGFD) to the neuronal cell and/or increasing the expression of VEGFD in the neuronal cell and/or activating the VEGFD receptor 2 and/or the VEGFD receptor 3 (VEGFR2/3) in the neuronal cell.

Further, the present invention relates to a method for decreasing at least one of the length and the complexity of the dendrites of a neuronal cell, comprising decreasing the expression of VEGFD and/or VEGFR2/3 in the neuronal cell and/or blocking VEGFD and/or VEGFR2/3 in the neuronal cell.

Furthermore, the present invention relates to a method for treating an age- and/or disease-related cognitive dysfunction in a subject in need thereof, comprising administering rVEGFD to the subject and/or increasing the expression of VEGFD in the subject's neuronal cells and/or activating VEGFR2/3 in the subject's neuronal cells.

Moreover, the present invention relates to a method for impairing the memory of a subject, comprising decreasing the expression of VEGFD and/or VEGFR2/3 in the subject's neuronal cells and/or blocking VEGFD and/or VEGFR2/3 in the subject's neuronal cells.

Finally, the present invention relates to rVEGFD for use in the treatment of an age- and/or disease-related cognitive dysfunction in a subject in need thereof.

The present invention will be further illustrated in the following examples without any limitation thereto.

Figure 1A:
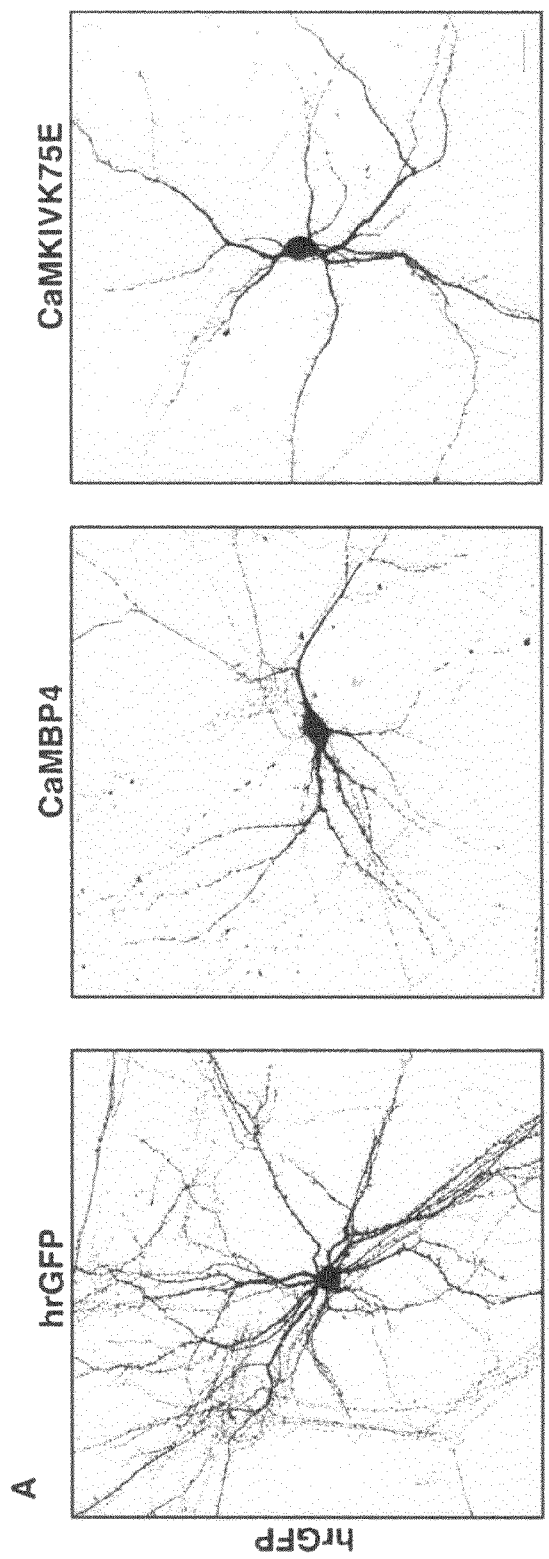
FIG. 1: Nuclear calcium signaling regulates neuronal morphology.

A: Representative micrographs of hippocampal neurons transfected with an expression vector for hrGFP or co-transfected with expression vectors for hrGFP and CaMBP4 or for hrGFP and CaMKIVK75E. Scale bar is 20 µm.

B-C: Quantification of total dendritic length and Sholl analysis in hippocampal neurons transfected with the indicated constructs.

D: Representative micrographs of dendritic spines of hippocampal neurons transfected as indicated. Scale bar is 5 μm.

E: Quantification of spine density of neurons transfected as in D.

F-G: Cumulative frequency plots of spine length and spine width in neurons transfected as indicated. More than 1000 spines and 12 neurons from a minimum of 3 independent preparations were examined for each construct. Statistically significant differences are indicated with asterisks ($p<0.005$, *$p<0.0005$).

FIG. 2: VEGFD expression is nuclear calcium signaling/CBP-dependent.

A: qRT-PCR analysis of VEGFD expression in hippocampal cultures at the indicated days in vitro (DIV) (n=5).

B: qRT-PCR analysis of VEGFD expression in uninfected hippocampal neurons and in hippocampal neurons infected with rAAVs giving rise to the indicated proteins (n=5).

C: qRT-PCR analysis of VEGFD, VEGFC, cFos, gapdh, beta tubulin and beta-microglobulin expression in cultured hippocampal neurons on DIV10 with or without treatment from DIV5 to DIV10 with 1μM TTX (n=3).

D: qRT-PCR analysis of VEGFD, VEGFC and cFos expression in cultured hippocampal neurons with or without treatment for 2 hrs with 50 μM bicuculline. VEGFD and VEGFC (Y) axis scale is shown on the left; cFos (Y) axis scale on the right (n=3).

E: qRT-PCR analysis of VEGFD, VEGFC and cFos expression in cultured hippocampal neurons with or without treatment from DIV5 to DIV10 with 10 μM MK801, 10 μM nifedipine or both (n=3).

F: qRT-PCR analysis of expression of cFos and VEGFD in uninfected hippocampal neurons and in hippocampal neurons infected with rAAV-CaMBP4 with or without treatment with actinomycin D (10 μg/ml) for 30min, 1h, 2hrs, 4hrs and 24 hrs (n=3).

G: qRT-PCR analysis of expression of cFos and VEGFD in uninfected hippocampal neurons and in hippocampal neurons infected with rAAV-E1A or rAAV-E1A ΔCR1 with or without treatment for 2 hrs with 50 μM bicuculline (bic). VEGFD (Y) axis scale is shown on the right; cFos (Y) axis scale on the left (n=3).

H: qRT-PCR analysis of expression of gapdh, CBP, and VEGFD in hippocampal neurons with or without treatment from DIV8-DIV13 with the indicated siRNAs (n=3).

I-J: Analysis of total dendritic length and Sholl analysis of neurons infected with rAAVE1A or rAAV-E1A CR1. 12 neurons from a minimum of 3 independent preparations were examined for each construct. Statistically significant differences are indicated with asterisks (*$p<0.05$, $p<0.005$, *$p<0.0005$).

See also FIG. 3.

FIG. 3: VEGFD expression in the nervous system and characterization of VEGFD-HA.

A: qRT-PCR analysis of VEGFD expression in hippocampal cultures uninfected and infected with rAAVs giving rise to the indicated proteins and analyzed at the indicated days in vitro (DIV) (n=4). Data are normalized to DIV10 which are the same data shown in FIG. 2B. Statistically significant differences are indicated with asterisks (*$p<0.05$, **$p<0.005$).

B: qRT-PCR analysis of Arc, bdnf, cFos, zif268, VEGFC, VEGF and VEGFR3 expression in hippocampal cultures uninfected or infected with rAAVs giving rise to the indicated proteins and analyzed at DIV10 (n=4).

C: qRT-PCR analysis of VEGFD expression in the mouse hippocampus and cortex at the indicated age (n=3). Statistically significant differences are indicated with asterisks (*$p<0.05$).

D: Immunocytochemical analysis of VEGFD in cultured hippocampal neurons using anti-VEGFD antibody or normal rabbit IgG as control, Hoechst to visualize the nuclei, NeuN is used as neuronal marker. Scale bar is 20 μm.

E: Immunohistochemistry of VEGFD in the CA1 region of the hippocampus of adult mice using anti-VEGFD antibody or normal rabbit IgG as control, Hoechst to visualize the nuclei, NeuN is used as neuronal marker; top panels show merge. Scale bar is 50 μm.

F: The boxed region indicated in E at higher magnification. Scale bar is 20 μm.

G: Hippocampal neurons were transfected with expression vectors for hrGFP and HA-tagged VEGFD; HA-tag immunoreactivity was highest in the perinuclear region. The hrGFP signal was used to visualize the neurons. Merge panel is shown on the right. Scale bar is 20 μm.

H: Immunoblot analysis of uninfected hippocampal neurons and of hippocampal neurons infected with rAAV-VEGFD. The immature, unprocessed form of VEGFD could be detected in the lysate and the partially cleaved form of VEGFD in the medium obtained from the same cultures through its HA-tag. Tubulin immunoblot is shown as control for protein loading.

Figure 4:
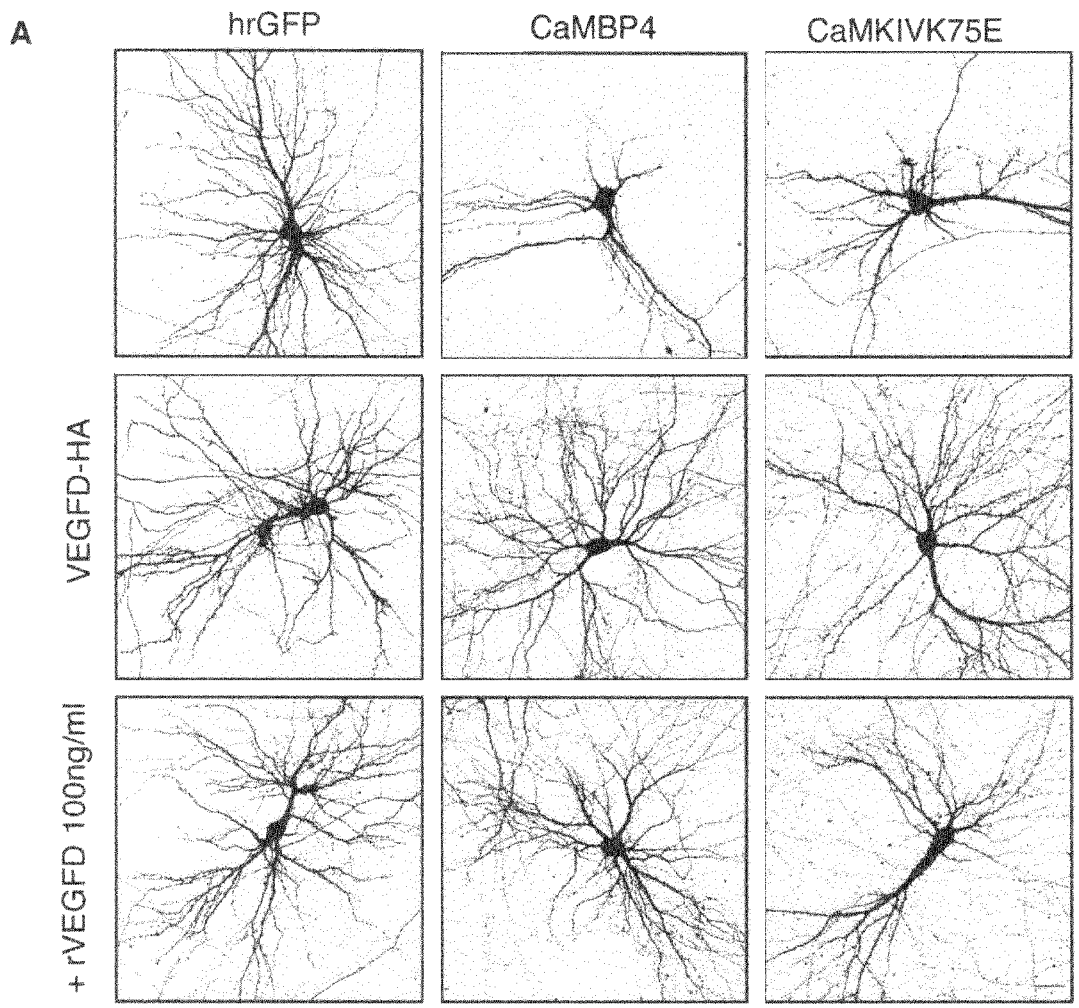

FIG. 4: VEGFD regulates dendritic architecture.

A: Representative micrographs of neurons transfected with expression vectors for the indicated proteins with or without treatment for 3 days with rVEGFD (100 ng/ml). Scale bar is 20 μm.

B-D: Sholl analysis and analysis of total dendritic length and spine density of neurons transfected, as indicated, with expression vectors for hrGFP, CaMBP4, CaMKIVK75E, VEGFD-HA.

E-G: Sholl analysis and analysis of total dendritic length and spine density of neurons transfected with expression vectors for hrGFP, CaMBP4, CaMKIVK75E with or without treatment for 3 days with rVEGFD. 12 neurons from a minimum of 3 independent preparations were examined for each construct. Statistically significant differences are indicated with asterisks (*$p<0.05$, $p<0.005$, *$p<0.0005$).

Figure 5:
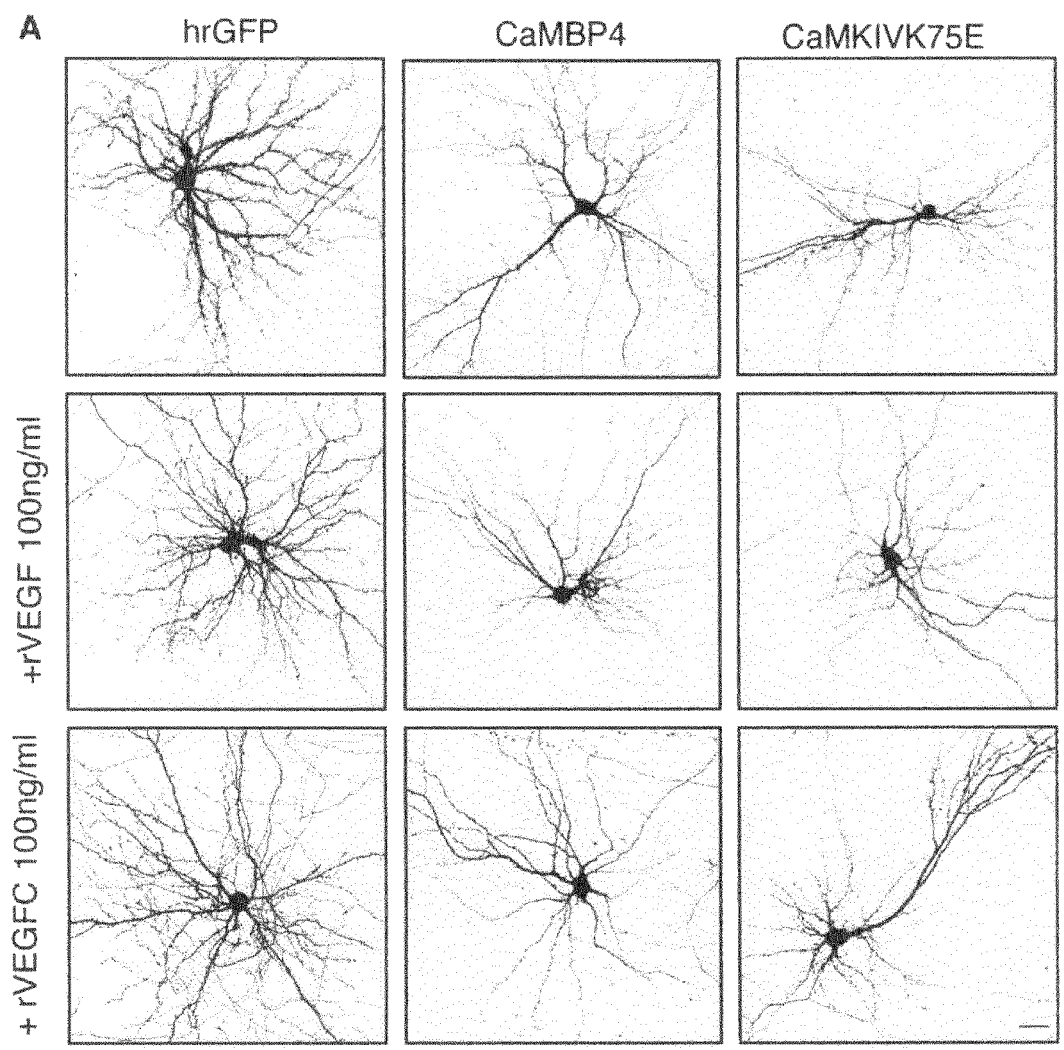

See also FIG. 5.

FIG. 5: VEGF and VEGFC did not rescue the altered dendritic morphology caused by nuclear calcium signaling blockade.

A: Representative micrographs of neurons transfected with expression vectors for the indicated proteins with or without treatment for 3 days with rVEGF or rVEGFC as indicated (100 ng/ml). Scale bar is 20 μm.

B-C: Sholl analysis and analysis of total dendritic length of neurons transfected, as indicated, with expression vectors for hrGFP, CaMBP4, CaMKIVK75E, with or without rVEGF treatment for 3 days.

D-E: Sholl analysis and analysis of total dendritic length of neurons transfected with expression vectors for hrGFP, CaMBP4, CaMKIVK75E with or without treatment for 3 days with rVEGFC. Data relative to hrGFP, CaMBP4, CaMKIVK75E without any treatment are the same shown in B to C and D to E; all conditions were performed at the same time, for clarity they are plotted as two separate sets. 12 neurons from a minimum of 3 independent preparations were examined for each construct. Statistically significant differences are indicated with asterisks (*$p<0.05$, **$p<0.005$).

FIG. 6: RNAi-mediated suppression of VEGFD expression is sufficient to alter dendritic morphology.

A: Schematic representation of the rAAV vector used for shRNA expression.

B: qRT-PCR analysis of expression of VEGFD and VEGFC in uninfected hippocampal neurons and in hippocampal neurons infected with rAAV-emptymC, rAAV-shVEGFD or with rAAV-shSCR (n=5).

C: Representative micrographs of hippocampal neurons transfected with pAAVemptymC or pAAV-shVEGFD, or with pAAV-shSCR with or without treatment for 3 days with rVEGFD (100ng/ml). The mCherry signal was used to visualize the neurons. Scale bar is 20 µm.

D-E: Sholl analysis and analysis of total dendritic length of neurons transfected as in C and, where indicated, treated with rVEGFD. 12 neurons from a minimum of 3 independent preparations were examined for each construct.

F: Analysis of total dendritic length of neurons transfected as in G. 12 neurons from a minimum of 3 independent preparations were examined for each construct.

G: Representative micrographs of hippocampal neurons transfected with pAAV-hrGFP (vector) or pAAV-VEGFD-HA, or with pAAV-resiVEGFD-HA with or without co-transfection with pAAV-shVEGFD. Scale bar is 20 µm.

H: Sholl analysis of neurons transfected as in G. 12 neurons from a minimum of 3 independent preparations were examined for each construct. Statistically significant differences are indicated with asterisks (*p<0.05, ***p<0.0005).

See also FIG. 7.

FIG. 7: Analysis of hippocampal neurons infected with rAAV-emptymC, rAAV-shVEGFD and rAAV-shSCR and of the VEGFD autocrine mechanism of action.

A: Representative micrographs of hippocampal cultures infected at DIV3 with rAAVemptymC, rAAV-shVEGFD or rAAV-shSCR. At DIV10 cells were fixed and stained with Hoechst (left panels) to visualize the nuclei; mCherry signal (right panels) identifies infected cells and was used to determine infection rates. Merge images are shown on the right. Scale bar is 20 µm.

B: Immunoblot analysis of uninfected hippocampal neurons and of hippocampal neurons infected with the indicated rAAVs. rAAV-emptymC, rAAV-shVEGFD and rAAV-shSCR carry all an mCherry cassette which was used for detection via an anti-DsRed antibody. Tubulin immunoblot is shown as control for protein loading.

C: Immunoblot analysis of VEGFD expression in uninfected hippocampal neurons and in hippocampal neurons infected with the indicated rAAVs. Tubulin was used for loading control. Neurons infected with rAAV-emptymC, rAAV-shVEGFD and rAAV-shSCR were detected by DsRed immunostaining (see above).

D: Analysis of interferon response using an Mx2:luc reporter gene in hippocampal neurons 30 hours after transfection. pAAV-shVEGFD did not induce an interferon response; poly (I:C) is used as positive control of the assay. Statistically significant differences are indicated with asterisks (*p<0.05).

E: Analysis of apoptosis of hippocampal cultures uninfected or infected with the indicated rAAVs. Values are expressed as percentage of the total number of cells analyzed.

F: Analysis of total dendritic length of neurons transfected with different shRNA sequences (indicated as '1', '2', '3') targeting VEGFD. 12 neurons from a minimum of 3 independent preparations were examined for each construct. Throughout the application the construct here referred as shVEGFD (T) was used. Statistically significant differences are indicated with asterisks (**p<0.005).

G: Representative micrographs of hippocampal cultures uninfected or infected at DIV3 with HA-tagged rAAV-VEGFD. At DIV8 cells were transfected with pAAV-emptymC, pAAV- shSCR or pAAV-shVEGFD as indicated. At DIV13 cultures were fixed and stained with Hoechst (left panels) to visualize the nuclei; HA to visualize rAAV-VEGFD infected neurons, mCherry signal identifies transfected cells and was used for morphometric analysis. Merge images are shown on the right. Scale bar is 20 µm.

H-I: Sholl analysis and analysis of total dendritic length of neurons infected and transfected as in G. 12 neurons from a minimum of 3 independent preparations were examined for each condition. Statistically significant differences are indicated with asterisks (***p<0.0005).

FIG. 8: RNAi-mediated suppression of VEGFR3 causes the same simplified dendritic arborization phenotype observed by silencing VEGFD.

A: qRT-PCR analysis of expression normalized to uninfected cells of VEGFD, VEGF, VEGFC and VEGFR3 in uninfected hippocampal neurons and in hippocampal neurons infected with rAAV-emptymC, rAAV-shVEGFD, rAAV-shVEGF, rAAV-shVEGFC or with rAAV-shVEGFR3 (n=3).

B: Representative micrographs of hippocampal neurons transfected with pAAVemptymC, pAAV-shSCR, pAAV-sh-VEGFD, pAAV-shVEGF, pAAV-sh VEGFC or with pAAV-shVEGFR3. The mCherry signal was used to visualize the neurons. Scale bar is 20 µm.

C-D: Sholl analysis and analysis of total dendritic length of neurons transfected as in C. 12 neurons from a minimum of 3 independent preparations were examined for each construct. Statistically significant differences are indicated with asterisks (*p<0.05, ***p<0.0005).

FIG. 9: VEGFD-induced signaling events.

A: Immunoblot analysis using phosphor-specific antibodies of hippocampal neurons with or without rVEGFD treatment for the indicated times. Tubulin was used as loading control.

B: Quantification of the experiment shown in A. rVEGFD treatment causes a significant increase of CREB, ERK1/2 and p38 MAP kinase phosphorylation. All values are expressed as percentage of untreated controls (n=5).

C: Immunocytochemical analysis using phosphor-CREB specific antibodies of hippocampal neurons with or without rVEGFD treatment for the indicated times. Nuclei of cells were counterstained with Hoechst 33258; NeuN was used as a neuronal marker. Representative images are shown. Scale bar is 20 µm.

D: Analysis of total dendritic length of neurons transfected with expression vectors for hrGFP, CaMBP4, CaMKIVK75E with or without treatment for 3 days with rVEGFD and/or SB203580. 12 neurons from a minimum of 3 independent preparations were examined for each experimental condition.

E: Sholl analysis of neurons transfected and treated as in D. Sholl analysis data of neurons expressing hrGFP, CaMBP4 or CaMKIVK75E and treated with SB203580 showed no difference compared to the respective untreated controls and were omitted from the graph for clarity.

F: Analysis of total dendritic length of neurons transfected with expression vectors for hrGFP, CaMBP4, shSCR, shp38alpha or shp38beta (as indicated) with or without treatment for 3 days with rVEGFD. 12 neurons from a minimum of 3 independent preparations were examined for each experimental condition. Statistically significant differences are indicated with asterisks (*p<0.05, p<0.005, *p<0.0005).

Figure 10:
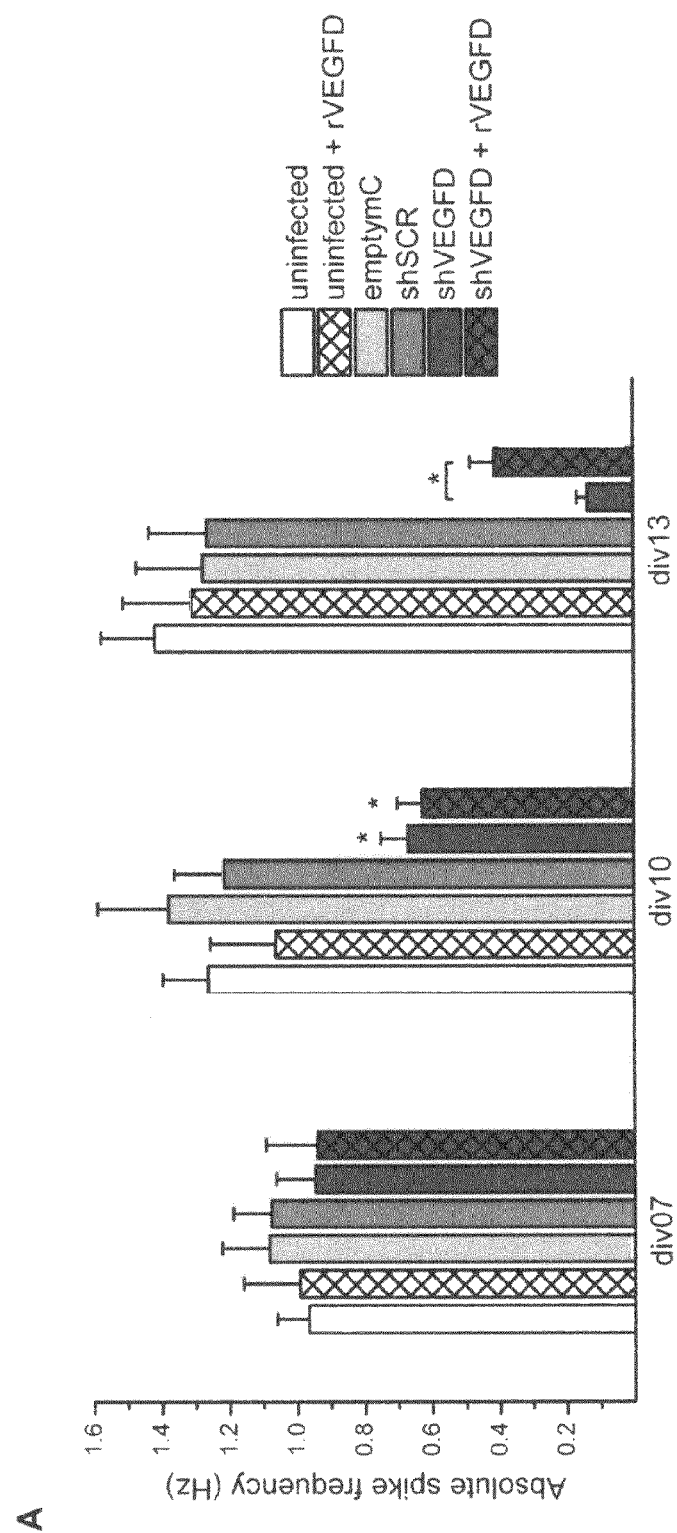

FIG. 10: MEA and patch clamp analysis reveals reduced activity, surface area and synaptic transmission in shVEGFD expressing neurons.

A: MEA analysis of absolute spike frequencies of uninfected hippocampal neurons and hippocampal neurons infected with rAAV-emptymC, rAAV-shVEGFD and rAAV-shSCR. Where indicated, cultures were treated at DIVE with 100 ng/ml rVEGFD. Statistically significant differences are indicated with asterisks (*p<0.05, ***p<0.0005).

B: Scatter plot showing the distribution and mean (horizontal bar) membrane capacitance (Cm) of transfected and infected neurons expressing shVEGFD or shSCR.

C: Representative mEPSCs averaged from 160 to 220 events in a pAAV-shVEGFD and a pAAV-shSCR transfected cell showing the raw average above and the scaled average below.

D: Representative responses to bath application of AMPA (10 μM, black or red bar) in the presence of cyclothiazide (20 μM), TTX (1 μM) and gabazine (5 μM) recorded from pAAV-shVEGFD and pAAV-shSCR transfected cells.

E-G: Scatter plots showing the distribution and mean (horizontal bar) mEPSC inter-event interval (IEI) (E), mEPSC amplitude (F) and AMPA response (G). Note the log scale of the ordinate axis in E and F. Significant differences between shVEGFD expressing cells and their respective transfected or infected shSCR expressing controls are indicated (* p <0.05, p<0.01, *p<0.001, ****p<0.0001 using Kolmogorov-Smirnov two sample tests; n =26 to 31 cells per group). See also Table 1.

Figure 11:
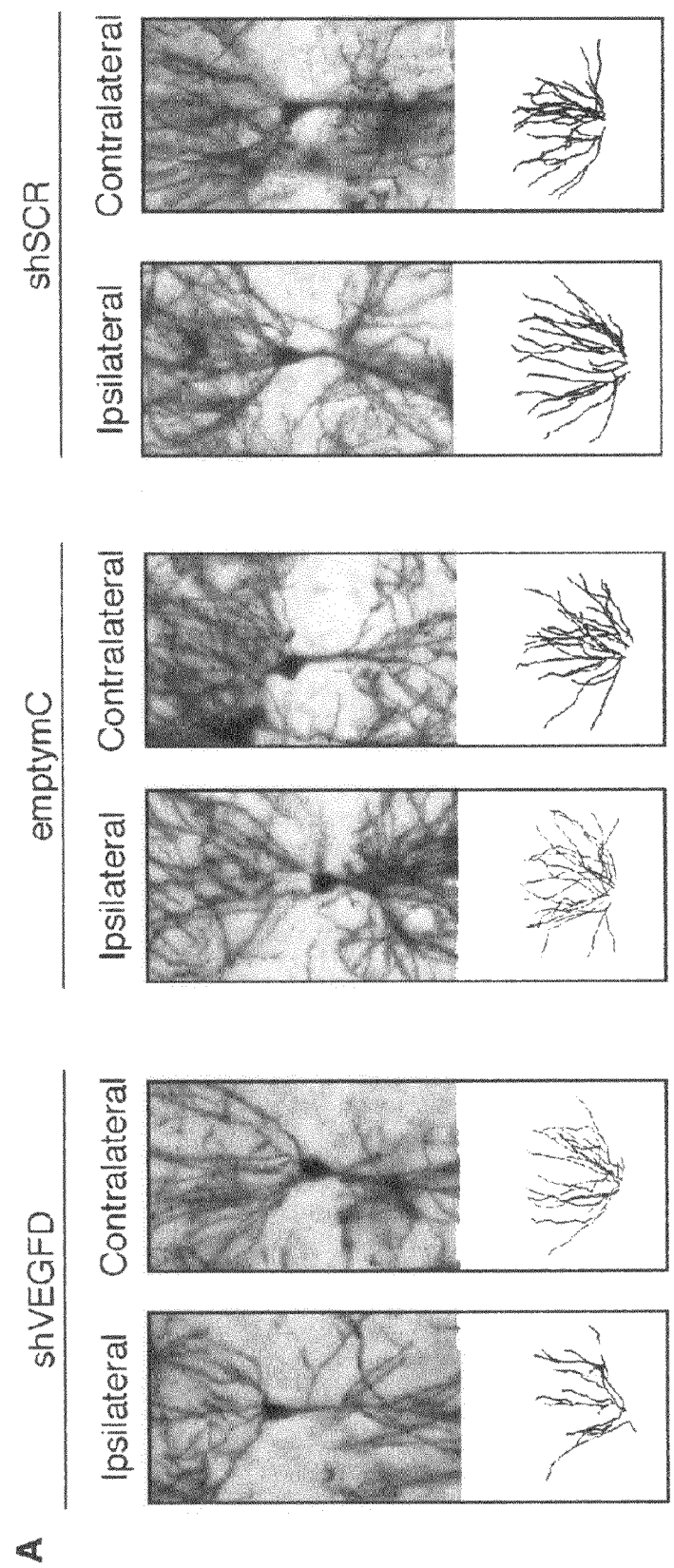

FIG. 11: RNAi-mediated suppression of VEGFD expression in vivo affects dendritic morphology and impairs memory formation.

A: Golgi-stained CA1 pyramidal neurons from the ipsilateral and contralateral hemispheres of mice stereotaxically-injected into the hippocampus with rAAVshVEGFD, rAAV-emptymC, or rAAV-shSCR. Representative tracings of the basal dendritic tree are shown. Scale bar is 10 μm.

B-C: Sholl analysis and analysis of total dendritic length of CA1 Golgi-stained pyramidal neurons from the ipsilateral and contralateral hippocampus of mice stereotaxically injected into the hippocampus with the indicated constructs. 20 neurons for each condition obtained from 4 injected animals per construct were analyzed.

D: Mean escape latency during acquisition of the hidden-platform version of the Morris water maze (rAAV-shVEGFD, n=8; rAAV-shSCR n=7).

E: Mean percent time spent in each quadrant during the probe trial test of the Morris water maze. T, target quadrant; CW, clockwise quadrant in relation to target; CCW, counter-clockwise quadrant in relation to target; 0, opposite quadrant in relation to target (rAAV-shVEGFD, n=8; rAAV-shSCR n=7).

F: Mean swimming speed during acquisition of the hidden-platform version of the Morris water maze (rAAV-shVEGFD, n=8; rAAV-shSCR n=7).

G: Mean escape latency during acquisition of the visible-platform version of the Morris water maze (rAAV-shVEGFD, n=8; rAAV-shSCR n=7).

H: Long-term contextual fear memory. Mice were injected with rAAV-shVEGFD or rAAV-shSCR; results are expressed as the percentage of time spent immobile during the contextual memory test (24 hours after training). (rAAV-shVEGFD, n=10; rAAV-shSCR, n=11).

I: Speed of movement during the 2 seconds electric foot shock delivered in training session of animals represented in H (rAAV-shVEGFD, n=10; rAAV-shSCR n=11).

J: Distance traveled during the initial 2.5 minutes exposure to the training chamber of animals represented in H (rAAV-shVEGFD, n=10; rAAV-shSCR n=11). Statistically significant differences (ANOVA followed by Tukey's posthoc test for morphometric, repeated measures ANOVA and one-way ANOVA followed by Tukey's posthoc test for Morris water maze and Student's t-test for behavioral analysis) are indicated with asterisks (p<0.005, *p<0.0005). See also FIG. 12.

Figure 12:
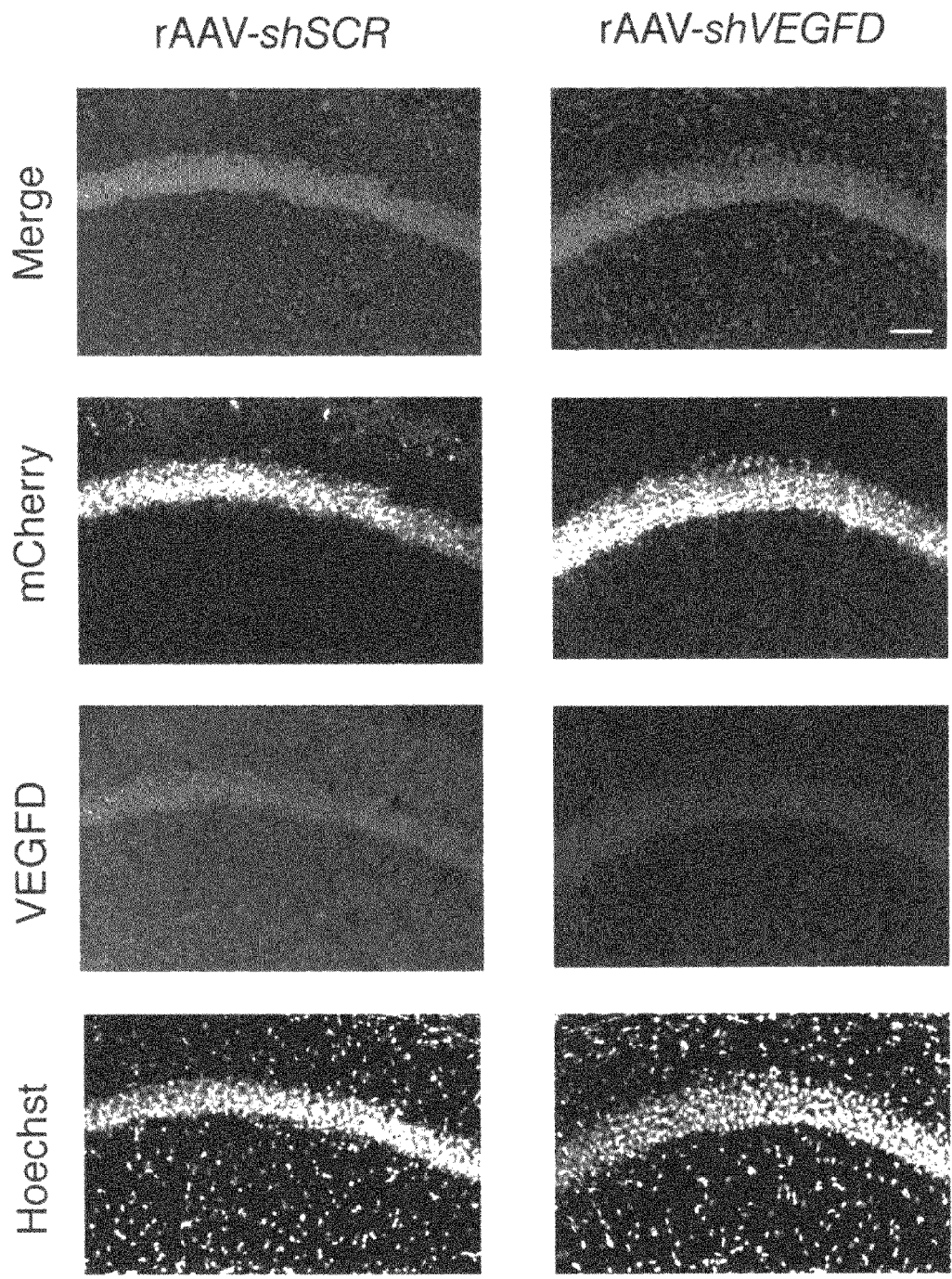

FIG. 12: Analysis of the hippocampus of mice stereotaxically injected with rAAV-shVEGFD and rAAV-shSCR. Immunohistochemistry of VEGFD expression in the CA1 region of the hippocampus of adult mice stereotaxically injected with rAAV-shVEGFD or rAAVshSCR using an anti-VEGFD antibody. Hoechst was used to visualize the nuclei; mCherry fluorescence was used to detect infected neurons. Scale bar is 50 μm.

Figure 13A:
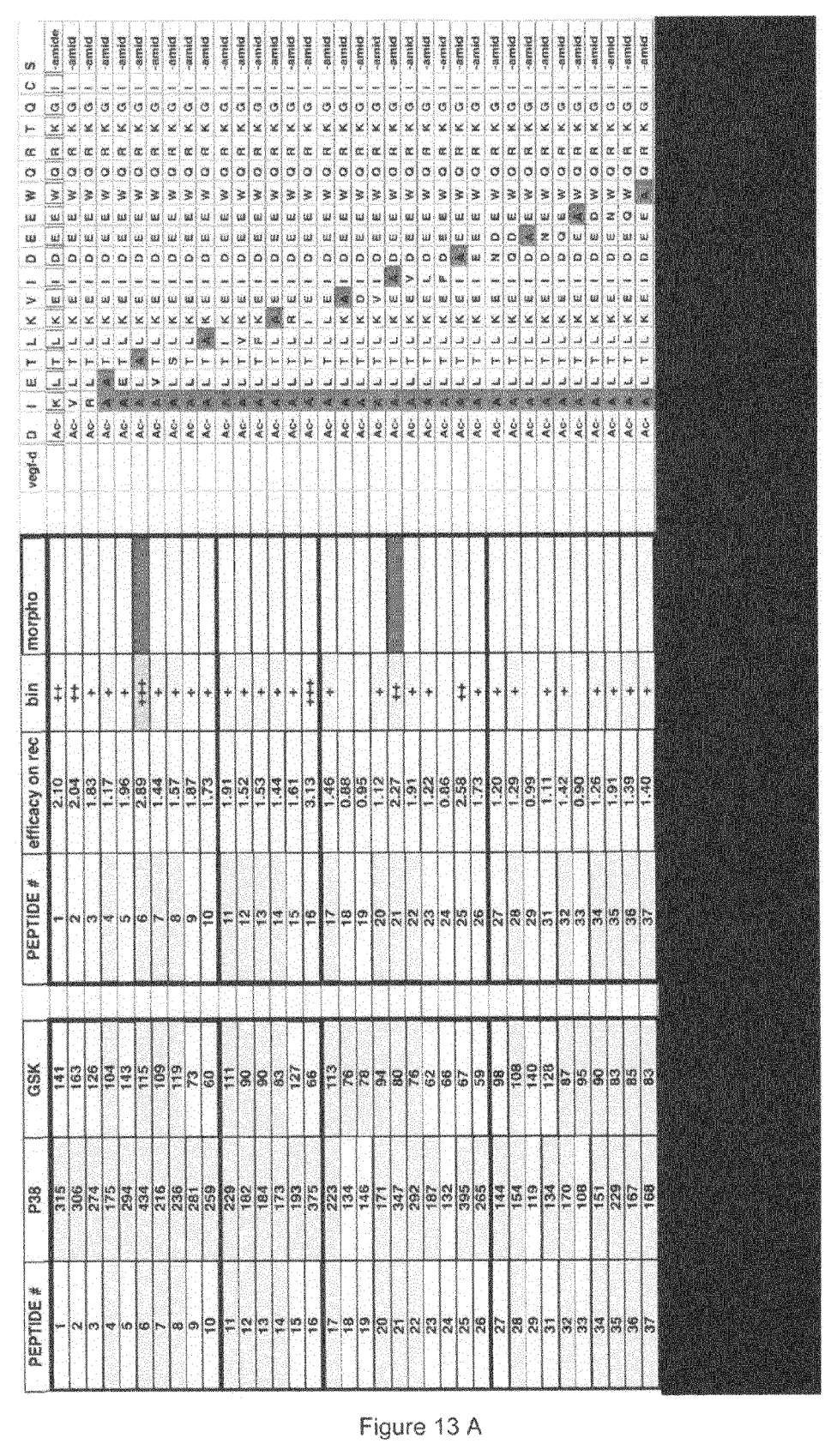
Figure 13C:
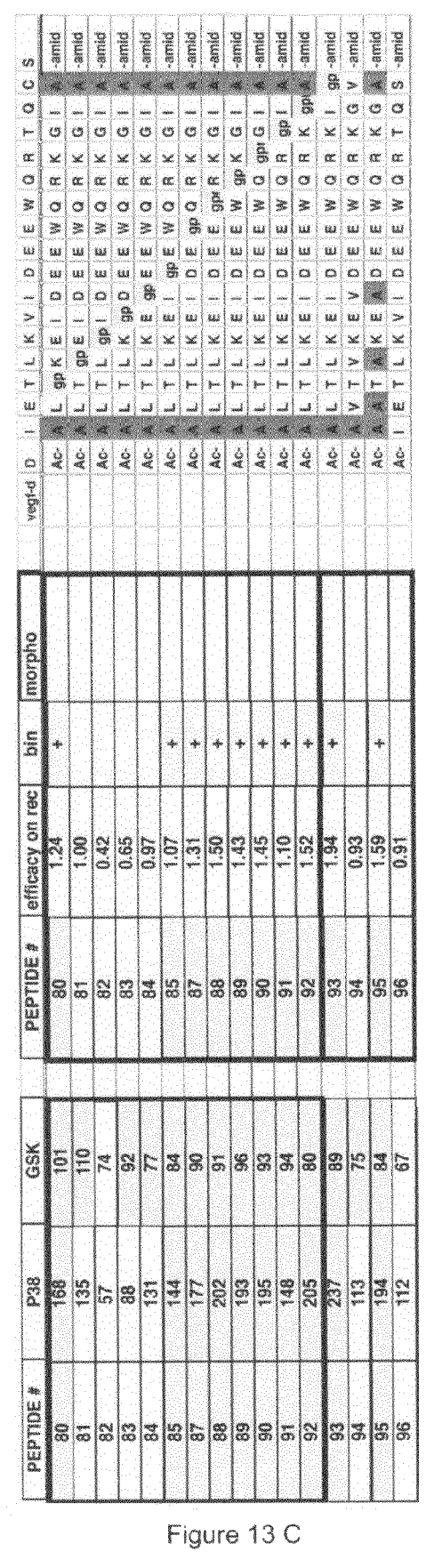

FIG. 13: Activity screening of a synthetic peptide library containing a sequence motif of VEGF-D and peptides that are varied in a systematic manner. A: Peptides 1 to 37; B: peptides 38 to 79; C: peptides 80 to 96.

Figure 14:
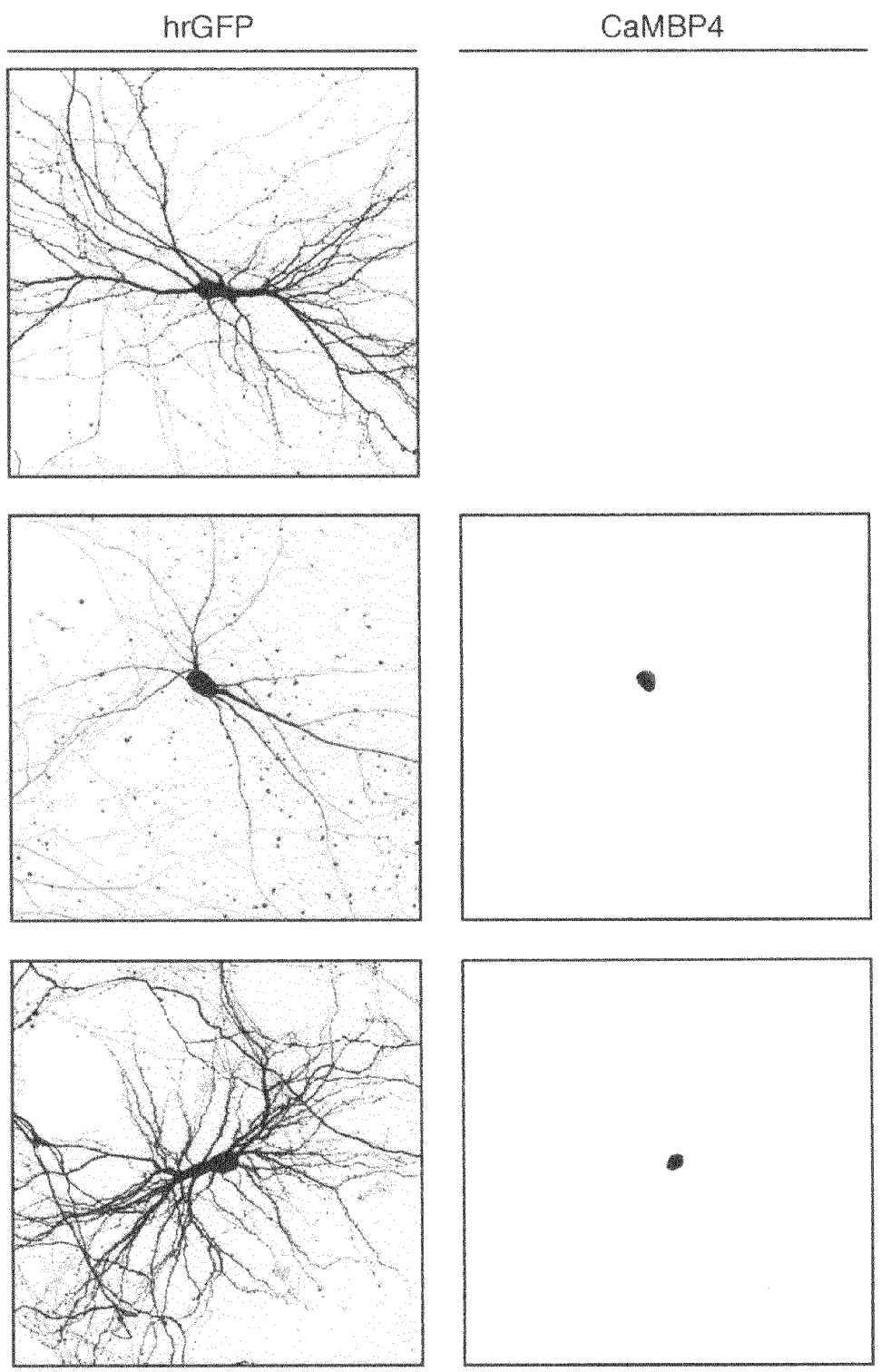

FIG. 14: Over-expression of CaMBP4 (Calcium/Calmodulin Binding Peptide 4) results in a decrease of dendritic length and complexity which can be rescued to normal levels by rVEGFD-treatment.

Figure 15:
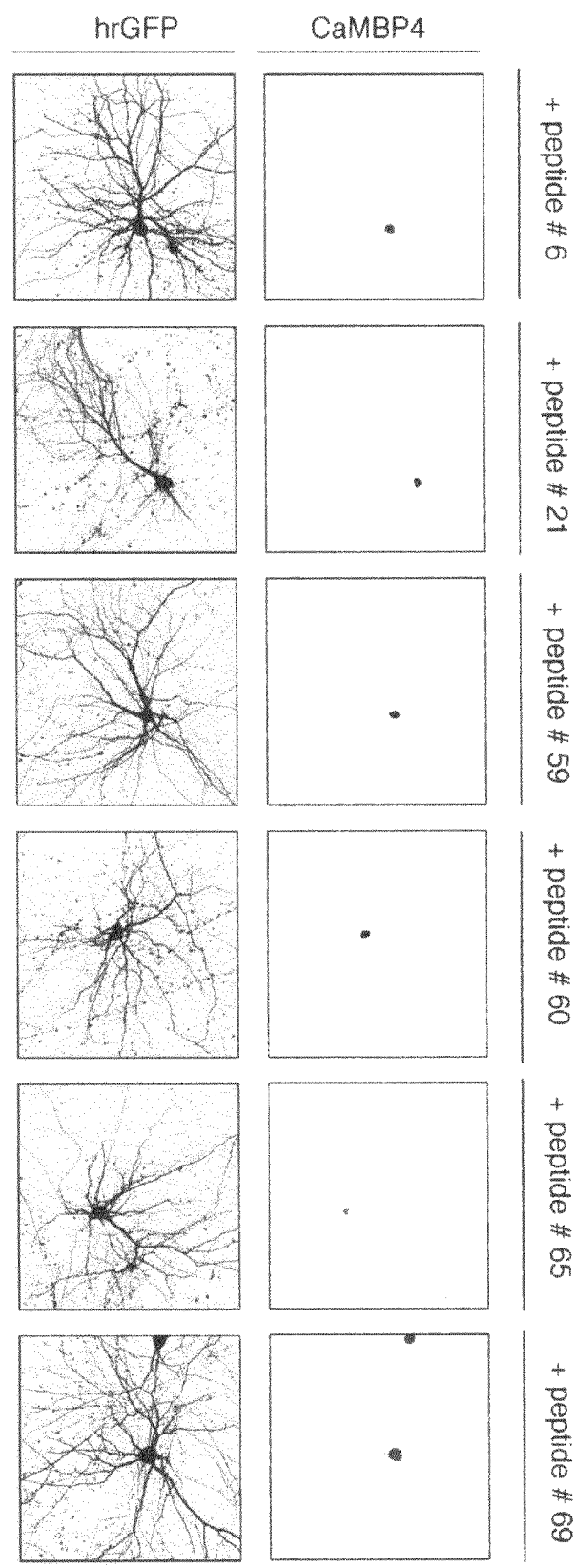

FIG. 15: Ability of six synthetic peptides to rescue the reduction of dendrite length and complexity caused by expression of CaMBP4.

Figure 16:
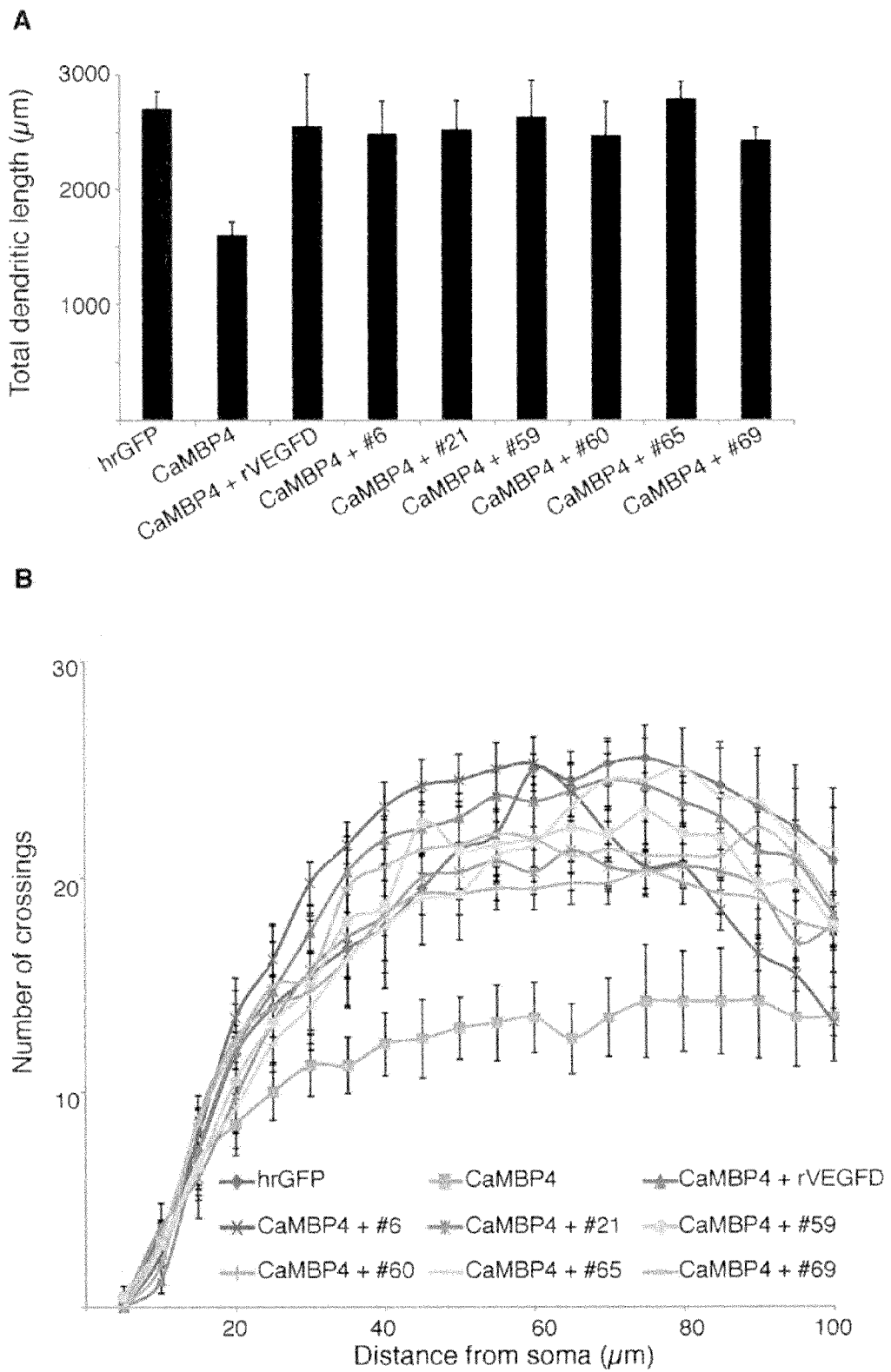

FIG. 16: Morphometric analysis of primary hippocampal neurons transfected with hrGFP and CaMBP4 and treated with peptides.

A: Total dendritic length. B: Dendritic complexity as measured by number of crossings vs. distance from soma.

DETAILED DESCRIPTION

In one aspect, the present invention relates to a method for increasing at least one of the length and the complexity of the dendrites of a neuronal cell, comprising at least one of the steps selected from the group consisting of (i) administering recombinant vascular endothelial growth factor D (rVEGFD) to the neuronal cell;

(ii) increasing the expression of VEGFD in the neuronal cell by transfecting the neuronal cell with a vector encoding rVEGFD; and (iii) activating at least one of the VEGFD receptor 2 and the VEGFD receptor 3 (VEGFR2/3) in the neuronal cell by administering an VEGFR2/3 activating agent to the neuronal cell.

In this context, the length of the dendrites of a neuronal cell is defined as the sum of the lengths of each individual dendrite of the neuronal cell, i.e. the sum of the lengths from the point where an individual dendrite branches off from the cell soma or from another dendrite to the furthest tip of that individual dendrite.

Further, the complexity of the dendrites of a neuronal cell is defined as the degree of arborization of the dendrite. The complexity of a dendrite can be quantified as the number of branching points, i.e. the number of points in which a dendrite further divides into others. Further, the complexity of a dendrite can be quantified using Sholl analysis, i.e. by computing the number of intersections between dendrites and circles of increasing diameter centered on the soma, wherein a higher number of intersections corresponds to a higher complexity.

The terms "vascular endothelial growth factor D" and "VEGFD" as used herein relate to VEGFD in its native, wild-type form, as well as to mutant forms of VEGFD having the same or higher efficacy as wild-type VEGFD, and tagged forms of VEGFD, e.g. VEGFD conjugated to green fluorescent protein (gfp-VEGFD), hemagglutinin (HA-VEGFD) or C-myc (myc-VEGFD). Furthermore, VEGFD can activate subtypes 2 and 3 of the VEGFD receptor (VEGFR). Accordingly, the term "VEGFR2/3" as used herein refers to both subtypes, i.e. the VEGFD receptor 2 and/or the VEGFD receptor 3.

Methods for the production of rVEGFD are not particularly limited and include for example the heterologous expression of rVEGFD in microorganisms such as *Escherichia coli*, insect cells such as Sf21 cells, or mammalian cells such as HEK293 cells. Respective methods for the expression of heterologous proteins in a wide range of host organisms are well known in the art.

Further, means for administering rVEGFD to neuronal cells are not particularly limited and include for example the supplementation of the culture medium of an in vitro cell culture. Administration routes in vivo include intravenous (i.v.), intraperitoneal (i.p.), intracerebroventricular (i.c.v.), intracerebral (i.c.), and intraspinal injections, intranasal delivery, transnasal convection-enhanced diffusion (CED), and implanted intracerebroventricular (ICV) catheters. Further, strategies for the in vivo delivery of peptides across the blood-brain barrier are known in the art and include for example linking rVEGFD to carriers such as antibodies, chemicals or liposomes. In this context, the blood-brain barrier is strongly compromised during cerebral ischemic events, facilitating the delivery of rVEGFD in this particular form of cognitive dysfunction.

Methods for increasing the expression of VEGFD in neuronal cells by transfecting the neuronal cells with a vector encoding rVEGFD are known in the art and are not particularly limited in the context of the present invention. They include for example the transfection of the cells with viral vectors encoding rVEGFD. Respective vectors, transfection methods and methods for the over-expression of VEGFD are well known in the art.

Finally, methods for activating VEGFR2/3 in neuronal cells by administering an VEGFR2/3 activating agent to the neuronal cells are not particularly limited and include for example the administration of activating antibodies to the cells. Respective activating agents include the natural ligands of VEGFR2/3 such as VEGF, VEGFD, VEGFC and VEGFB. In a preferred embodiment, the VEGFR2/3 activating agent is a peptide. Preferably, the peptide comprises at least 10 to 25 consecutive amino acids of the peptide sequence shown in SEQ ID NO: 8 (amino acid sequence SMDSRSASHRSTRFAATFYDTETLKVIDE EWQRTQCSPRETCVEVASELGKTTNT). This stretch of consecutive amino acids can be modified vis-á-vis the peptide sequence shown in SEQ ID NO: 8 by deletions, insertions or point mutations. The peptide preferably has a length of 10 to 25 amino acids. In particularly preferred embodiments, the peptide comprises at least one of the amino acid sequences shown in SEQ ID NO: 9 to 14, or consists of said amino acid sequences. Means for the delivery of activating agents and/or antibodies and/or peptides are known in the art and include the above means as defined for rVEGFD.

In a preferred embodiment of this aspect of the present invention, the respective method is performed in vitro, i.e. it is not practiced on the human or animal body.

In another aspect, the present invention relates to a method for decreasing at least one of the length and the complexity of the dendrites of a neuronal cell, comprising at least one of the steps selected from the group consisting of (i) decreasing the expression of vascular endothelial growth factor D (VEGFD) in the neuronal cell by administering at least one of a suitable shRNA and a vector encoding a suitable shRNA to the neuronal cell;

(ii) decreasing the expression of at least one of the VEGFD receptor 2 and the VEGFD receptor 3 (VEGFR2/3) in the neuronal cell by administering at least one of a suitable shRNA and a vector encoding a suitable shRNA to the neuronal cell;

(iii) blocking VEGFD in the neuronal cell by administering a VEGFD blocking agent to the neuronal cell; and (iv) blocking VEGFR2/3 in the neuronal cell by administering a VEGFR2/3 blocking agent to the neuronal cell.

Methods for decreasing the expression of VEGFD and/or VEGFR2/3 in neuronal cells by administering at least one of a suitable shRNA and a vector encoding a suitable shRNA to the neuronal cell are known in the art and are not particularly limited. They rely on the knock-down of the respective genes using RNA interference (RNAi). RNAi techniques are well known in the art and include for example the transfection of the cells with respective shRNAs or vectors encoding such shRNAs. In the present application, a DNA sequence encoding an shRNA for the efficient knock-down of murine VEGFD was found to be the sequence GGGCTTCAGGAGCGAACAT (SEQ ID NO: 1). Methods for identifying further sequences for the knockdown of VEGFD or VEGFR2/3 in various species are known in the art.

Further, methods for blocking VEGFD and/or VEGFR2/3 in neuronal cells by administering a VEGFD or VEGFR2/3 blocking agent to the neuronal cells are not particularly limited and include for example the administration of respective blocking antibodies to the cells. Means for the delivery of blocking agents and/or antibodies are known in the art and include the above means as defined for rVEGFD.

In a preferred embodiment of this aspect of the present invention, the respective method is performed in vitro, i.e. it is not practiced on the human or animal body.

In any pathological situation where dendritic trees and cognition are impaired, positive regulation of VEGFD signaling can be used to restore normal functioning. Strategies aimed at maintaining or restoring appropriate dendrite lengths and branching patterns, involving the modulation of neuronal VEGFD levels, represent novel ways in the development of effective therapies for age- and/or disease-related cognitive dysfunctions. Further, drugs aimed at activating VEGFR2/3 can also find therapeutic use.

Accordingly, in another aspect, the present invention relates to a method for treating an age- and/or disease-related cognitive dysfunction in a subject in need thereof, comprising at least one of the steps selected from the group consisting of (i) administering recombinant vascular endothelial growth factor D (rVEGFD) to the subject;

(ii) increasing the expression of VEGFD in the subject's neuronal cells by administering a vector encoding rVEGFD to the subject; and (iii) activating at least one of the VEGFD receptor 2 and the VEGFD receptor 3 (VEGFR2/3) in the subject's neuronal cells by administering a VEGFR2/3 activating agent to the subject.

In this context, cognitive dysfunctions are any malfunctions, disorders or functional disorders of the cognitive systems of the subject. Age- and/or disease-related cognitive dysfunctions are preferably cognitive dysfunctions that are caused by a condition, selected from the group consisting of ischemia, in particular cerebral ischemia, Down syndrome, Rett syndrome, neurodegenerative disease, Alzheimer's disease, ageing, metabolic dysfunction, and infection with human immunodeficiency virus (HIV).

Methods for administering rVEGFD to a subject are known in the art and include for example the in vivo means of administration as defined above for rVEGFD.

Further, methods for increasing the expression of VEGFD in a subject's neuronal cells by administering a vector encoding rVEGFD to the subject are known in the art and include for example transfection or infection with viral vectors encoding rVEGFD. Respective vectors, transfection methods, infection methods and methods for the over-expression of VEGFD are well known in the art.

Finally, methods for activating VEGFR2/3 in a subject's neuronal cells by administering a VEGFR2/3 activating agent to the subject are known in the art and include for example the administration of a VEGFR2/3-activating antibody to the subject. Respective activating agents include the natural ligands of VEGFR2/3 such as VEGF, VEGFD, VEGFC and VEGFB. In a preferred embodiment, the VEGFR2/3 activating agent is a peptide. Preferably, the peptide comprises at least 10 to 25 consecutive amino acids of the peptide sequence shown in SEQ ID NO: 8. This stretch of consecutive amino acids can be modified vis-á-vis the peptide sequence shown in SEQ ID NO: 8 by deletions, insertions or point mutations. The peptide preferably has a length of 10 to 25 amino acids. Means for the delivery of activating agents and/or antibodies are known in the art and include the above in vivo means as defined for rVEGFD.

In a preferred embodiment of this aspect of the present invention, the subject is a non-human vertebrate. In another preferred embodiment, the subject is a non-human mammal. In another preferred embodiment, the subject is human.

Means to specifically shorten and simplify dendrites provide new tools for developing animal models of cognitive impairments. In this context, silencing the expression of VEGFD or VEGFR2/3 or blocking VEGFD or VEGFR2/3 also proves to be useful. A respective method can further be used for the treatment of post-traumatic stress syndrome by impairing the patient's memory. Accordingly, in another aspect, the present invention relates to a method for impairing the memory of a subject, comprising at least one of the steps selected from the group consisting of
(i) decreasing the expression of vascular endothelial growth factor D (VEGFD) in the subject's neuronal cells by administering at least one of a suitable shRNA and a vector encoding a suitable shRNA to the subject;
(ii) decreasing the expression of at least one of the VEGFD receptor 2 and the VEGFD receptor 3 (VEGFR2/3) in the subject's neuronal cells by administering at least one of a suitable shRNA and a vector encoding a suitable shRNA to the subject;
(iii) blocking VEGFD in the subject's neuronal cells by administering a VEGFD blocking agent to the subject; and
(iv) blocking VEGFR2/3 in the subject's neuronal cell by administering a VEGFR2/3 blocking agent to the subject.

Methods for decreasing the expression of VEGFD and/or VEGFR2/3 in a subject's neuronal cells by administering at least one of a suitable shRNA and a vector encoding a suitable shRNA to the subject are known in the art and rely on the knock-down of the respective genes using RNA interference (RNAi). RNAi techniques are well known in the art and include for example the transfection or infection with respective shRNAs or vectors encoding such shRNAs. Methods for identifying sequences for the knockdown of VEGFD or VEGFR2/3 in various species are known in the art.

Further, methods for blocking VEGFD and/or VEGFR2/3 in a subject's neuronal cells by administering a VEGFD or VEGFR2/3 blocking agent to the subject are known in the art and include for example the administration of respective blocking antibodies to the subject. Means for the delivery of blocking agents and/or antibodies are known in the art and include the above means as defined for rVEGFD.

In a preferred embodiment of this aspect of the present invention, the method is used for the generation of an animal that provides a model system for cognitive dysfunctions. Accordingly, the subject is preferably an animal, preferably a non-human vertebrate or a non-human mammal, preferably a mouse.

In another preferred embodiment of this aspect of the present invention, the subject is human. In case the subject is a human, the method is preferably used for the treatment of post-traumatic stress syndrome.

In further aspects, the present invention relates to a member, selected from the group consisting of rVEGFD, a vector encoding rVEGFD, and a VEGFR2/3 activating agent, for use in increasing at least one of the length and the complexity of the dendrites of a subject's neuronal cells.

In preferred embodiments, increasing at least one of the length and the complexity of the dendrites of a subject's neuronal cells is for the treatment of an age- and/or disease-related cognitive dysfunction in a subject. In these embodiments, the age- and/or disease-related cognitive dysfunction as well as the method for the treatment thereof is as defined above. Further, the subject is preferably human. Furthermore, rVEGFD, vectors encoding rVEGFD, and VEGFR2/3 activating agents are as defined above.

In further aspects, the present invention relates to a member, selected from the group consisting of small hairpin RNAs (shRNAs) capable of decreasing the expression of VEGFD in a subject, shRNAs capable of decreasing the expression of VEGFR2/3 in a subject, VEGFD blocking agents, and VEGFR2/3 blocking agents, for use in decreasing at least one of the length and the complexity of the dendrites of a subject's neuronal cells.

In preferred embodiments, decreasing at least one of the length and the complexity of the dendrites of a subject's neuronal cells is for impairing the memory of a subject and/or for the treatment of post-traumatic stress syndrome. Further, the subject is preferably human. Furthermore, shRNAs capable of decreasing the expression of VEGFD in a subject, shRNAs capable of decreasing the expression of VEGFR2/3 in a subject, VEGFD blocking agents, and VEGFR2/3 blocking agents are as defined above.

In the present invention, VEGFD is identified as a regulator of neuronal dendrite geometry. VEGFD mediates the effects of synaptic activity and nuclear calcium-CaMKIV signaling on the maintenance of complex dendrite arborization, which is necessary for memory formation.

Neurons, even once fully developed, remain plastic and undergo activity-dependent functional or structural alterations. Changes in gene expression—induced by synaptic activity and calcium transients propagating towards and into the nucleus—are often essential for the long-term maintenance of adaptive responses. Dendritic trees, the branched projections of the input-receiving ends of neurons, are prime targets for activity-regulated structural alterations.

Intrinsic, pre-determined genetic programs and cell autonomous mechanisms have been shown to determine dendrite morphogenesis in developing neurons. However, there is an increasing appreciation of the influence of the electrical activity of neurons on dendrite arborization. The present invention shows that VEGFD plays a central role in this process; as a target of nuclear calcium-CaMKIV signaling, it links basal neuronal activity to the control of total dendrite length and branching patterns, thereby providing neurons of the adult nervous system with the structural features needed for proper cognitive performance of the organism. These new findings explain why interference either with nuclear calcium signaling or with CaMKIV activity compromises the ability of mice to form long-term memories. They also suggest a generally applicable concept, in which impairments of synaptic transmission, for example due to synapse loss in ageing or Alzheimer's Disease, and/or malfunctioning of activity-induced calcium signaling towards and within the cell nucleus, may lead to a decrease in VEGFD expression, followed by a reduction in dendrite complexity and finally, an emergence of cognitive deficits. Strategies aimed at maintaining or restoring appropriate dendrite lengths and branching patterns—either through supplementation of VEGFD or enhancement of nuclear calcium signaling—therefore represent novel avenues in the development of effective therapies for age- and disease-related cognitive dysfunction.

EXAMPLES

Materials and Methods

Hippocampal cultures and transfection. Hippocampal neurons from newborn C57BL/6 mice were cultured as known in the art. Experiments were done after a culturing period of 10 to 14 days in vitro (DIV). DNA transfection was done on DIV8 using Lipofectamine 2000 (Invitrogen, San Diego, Calif.). For the studies on dendrite morphology, neurons were analyzed 4-5 days after transfection.

Stereotaxic delivery of rAAVs. rAAVs were delivered by stereotaxic injection into the right dorsal hippocampus of 2 months old male C57BL/6 mice. For the Golgi staining-based morphometric analysis, viral particles were unilaterally injected over a period of 20 min at the following coordinates relative to Bregma: anteroposterior, −2.1 mm; mediolateral, −1.4 mm; dorsoventral, −1.4 to −1.8 mm from the skull surface. For behavior experiments mice were injected bilaterally.

Morphometric analyses. For 3D Sholl Analysis, total dendritic length and spine morphology were calculated using Object-Image freeware software with a specific set of macros (written by Dr. E. Ruthazer, McGill University, Quebec). Briefly, a z-Stack acquisition was imported, calibrated in Object-Image and manually traced. Total dendritic length was then computed. For Sholl analysis, the shell interval was set at 5 µm. All analyses were performed blind. In all in vitro experiments, for each condition, a minimum of 12 neurons from three independent preparations was analyzed. For the Golgi staining quantifications of 20 neurons for each condition from 4 different injected animals per viral construct were traced and analyzed.

MEA recordings. MEA recordings were done as known in the art. From DIV7 to DIV13, recordings of spontaneous network activity were acquired for 5 min once per day.

Patch clamp recordings. Whole-cell patch clamp recordings were made at room temperature from cultured hippocampal neurons plated on coverslips secured with a platinum ring in a recording chamber (Open access chamber-1, Science Products GmbH, Hofheim, Germany) mounted on a fixed-stage upright microscope (BX51WI, Olympus, Hamburg, Germany). Differential interference contrast optics, infrared illumination and a CCD camera (PCO, Visitron Systems, Puchheim, Germany) connected to a contrast enhancement unit (Argus, Hamamatsu, Herrsching am Ammersee, Germany) were used to view neurons on a video monitor. Recordings were made with a Multiclamp 700A amplifier, digitized through a Digidata 1322A ND converter and acquired using pClamp software (Molecular Devices, CA, USA). All membrane potentials have been corrected for the calculated junction potential of −11 mV (JPCalc program by Dr. Peter H. Barry). mEPSCs and whole-cell AMPA (10 µM, 6 ml/min, Biotrend) responses were recorded as known in the art except for the solutions and that a holding potential of −71 mV was used and both TTX (1 µM, Biotrend, Cologne, Germany) and gabazine (5 µM, Biotrend) were included in the ACSF. TTX was applied before gabazine to prevent the induction of action potential bursting. Access (range: 7-18 MU) and membrane resistance (see Table 1) were monitored before and after mEPSC recordings and data was rejected if changes greater than 20% occurred.

Behavioral experiments. The behavioral experiments started three weeks after stereotaxic delivery of rAAVs. Mice were habituated to the experimental room and handled once a day for three consecutive days before testing started. Two different sets of mice were used for Morris water maze and contextual fear conditioning experiments. At the end of the experiments, virus infection was assessed.

Morris water maze. Mice were first tested in the hidden-platform version and next in the visible-platform version of the water maze. The water maze consisted of a circular pool (120 cm diameter) filled with opaque water (water was made opaque with non-toxic white paint). The platform (10 cm diameter) was submerged 1 cm below the water level. On the first day of the hidden-platform version, mice were habituated to the water and the platform for two 60 seconds trials. In each habituation trial, mice were allowed to swim for 30 seconds and then placed on the platform for another 30 seconds. During the acquisition phase, mice were placed four times a day into a pool with a submerged platform located in a fixed position (approximately 5 minutes inter-trial interval) for four days. Each training trial lasted a maximum of 60 seconds, and when mice did not find the platform they were placed on it and allowed to sit for 20 seconds. On the fifth day, mice were given a 60 second probe trial, for which the platform was not in the pool. This was followed by four more days of training. A second probe trial was given on the tenth day. In the visible-platform version, mice were trained to find the platform using a proximal visible cue (red ball placed 10 cm above the platform). All other visual cues were removed from the room and the location of the platform was different in each trial. The training consisted of four trials a day during three consecutive days. Each trial lasted a maximum of 60 seconds and when mice did not find the platform they were placed on it for 20 seconds. The path of the mouse was recorded using a video tracking system (ANY-Maze, Stoelting, Ireland).

Contextual fear conditioning. On the training day, mice were placed into the conditioning chamber (23×23×35 cm; TSE, Bad Homburg, Germany) and received a 2 second, 0.5 mA scrambled foot shock 148 seconds after placement into the chamber. Mice were removed from the chamber 30 seconds after the shock. During testing, mice received one 5 minute exposure to the same context in the absence of foot shock 24 hours after conditioning. Freezing, defined as absence of movement except for respiration, was scored continuously during training and testing sessions.

Data analysis. All plotted data represent mean±SEM. One-way analysis of variance (ANOVA) with Tukey's post hoc test was used for statistical analyses except where stated otherwise. In those experiments where only two conditions are tested, comparisons were made using a Student's t-test for independent samples. In the Morris water maze experiment, repeated measures ANOVA and one-way ANOVA were used to analyze acquisition curves and probe trial, respectively.

RNA extraction and cDNA synthesis. Total RNA was isolated at DIV10 to DIV13 from hippocampal primary neuron cultures or isolated brain tissues with Rneasy Mini Kit (Qiagen, Hilden, Germany) including an optional Dnase I treatment at room temperature for 15 min according to manufacturer's instructions (Qiagen). 1.2 µg of extracted RNA was reverse transcribed into first strand cDNA using High Capacity cDNA Reverse Transcription kit (Applied Biosystems, Foster City, Calif.).

Real Time Quantitative PCR. Quantitative reverse transcriptase PCR (qRT-PCR) was done on an ABI7300 thermal cycler using Universal qRT-PCR master mix with TaqMan Gene Expression Assays for the indicated genes (Applied Biosystems). The following TaqMan Gene Expression Assays were used in this study: Gusb (Mm00446953_m1), cFos (Mm00487425_m1), VEGFD (Mm00438965_m1), VEGFC (Mm01202432_m1), VEGF (Mm01281449_m1), VEGFR3 (Mm01292618_m1), beta-actin (Mm00607939_s1), beta-2 microglobulin (Mm00437762_m1), CBP (Mm01342435_m1), p38 MAPK alpha (Mm00442497_m1), p38 MAPK beta (Mm00440955_m1). Expression of target genes was normalized against the expression of Gusb as endogenous control gene. Data were derived from at least 5 independent experiments.

Recombinant adeno-associated viruses. The vectors used to construct and package rAAVs have been described in the art. rAAV-CaMKIVK75E, rAAV-LacZ, and rAAV-CaMBP4 all generate Flag-tagged proteins which have been previously characterized in the art. The cDNA encoding mouse VEGFD, mouse VEGFD resistant to shVEGFD, E1A and E1AΔCR1 fused to the sequence encoding an HA tag were cloned in the same rAAV vector by standard molecular biology techniques and verified by sequencing. Viral particles were produced and purified as known in the art. For viral infection, neurons were infected with $2-5\times10^9$ particles/ml on DIV3 and harvested on DIV10. Infection efficiencies were determined immunocytochemically and by immunoblotting using antibodies to the appropriate tag or by analyzing mCherry fluorescence and ranged from 80 to 95 percent of the neuronal population.

Short hairpin RNA- and small interfering RNA-mediated knockdown.

For expression of shRNAs, an rAAV vector containing the U6 promoter for shRNA expression and a CaMKII promoter driving mCherry expression was used. Three different sequences were obtained from Open Biosystems (shVEGFD 1, shVEGFD 2 and shVEGFD 3), cloned and tested for silencing efficiency. shVEGFD (1) (GGGCTTCAGGAGCGAACAT; SEQ ID NO: 1) was selected as being the most potent. As control, a scramble version of this sequence (shSCR; GTGCCAAGACGGGTAGTCA; SEQ ID NO: 2) and the vector carrying only the mCherry (emptymC) were used. Shp38alpha (AAACACGAAAATGTGATTGGT; SEQ ID NO: 3), shp38beta (AAGCACGAGAACGTCATAGGA; SEQ ID NO: 4), shVEGF (ACCTCACCAAAGCCAGCAC; SEQ ID NO: 5), shVEGFC (GTTCATTCCATTATTAGAC; SEQ ID NO: 6) and shVEGFR3 (CCCAGTATTGTGTGGTACAAA; SEQ ID NO: 7; sequence obtained from Open Biosystems) were also cloned into the same vector. CBP expression level was knocked down using a pool of four short interfering RNAs (siRNAs) targeting mouse CBP (Accell siRNA SMARTpool; Thermo Scientific Dharmacon). The SMARTpool is a group of four siRNAs that have been screened to reduce a variety of potential off-target effects including the inclusion of miRNA (microRNA)-like seed motifs. Silencing of GAPDH was measured using Accell mouse GAPDH as a positive control, and as a negative control, a non-targeting Accell mouse siRNA pool was used. In addition, a fluorescently labeled non-targeting Accell mouse siRNA was also used to evaluate penetration efficiency in hippocampal neurons via immunocytochemistry. Briefly, 500 nM siRNAs were supplemented in the serum-free culturing medium at DIV8, and mRNA levels were analyzed at DIV13.

Immunocytochemistry. Hippocampal neurons were fixed with 4% paraformaldehyde at room temperature for 20 min. For immunostaining, primary and secondary antibodies were applied in GDB buffer (30 mM phosphate buffer [pH7.4] containing 0.2% gelatin, 0.5% Triton X-100, and 0.9 M NaCl). For the morphometric analyses, fluorescence images were acquired using a confocal laser-scanning microscope TCS SP2 (Leica, Mannheim, Germany) equipped with an inverted fluorescence microscope DM IRE2 (Leica) and Leica confocal scan software. All images were obtained with sequential acquisition setting at a resolution of 1024×1024 pixels. Each image was a z series projection of images taken at 1 μm intervals.

Immunohistochemistry. Animals were deeply anesthetized with Nembutal, pre-perfused trans-cardially with PBS, and perfused with neutral phosphate buffered 10% formalin (Sigma-Aldrich, Munich, Germany). Brains were removed and post-fixed overnight in the same fixative solution. For cryoprotection, brains were incubated for 2 days in 30% sucrose in 0.1M phosphate buffer containing 0.04% thimerosal (Sigma). 40 μm thick frozen sections, cut at −20° C., were collected in PBS containing 0.04% thimerosal. Neurons were identified by NeuN immunostaining (1:500, mouse monoclonal; Chemicon); VEGFD was detected with an antibody raised against the immature precursor (1:250, rabbit polyclonal, Santa Cruz). Sections were blocked in 1% BSA, 5% normal goat serum (NGS), 0.1% triton X-100 in PBS for 1 hour at room temperature, incubated with primary antibody diluted in 1% BSA, 1% normal goat serum (NGS), 0.1% Triton X-100 at 4° C., overnight. Sections were rinsed twice with PBS containing 0.1% Triton X-100, and incubated with the secondary antibody in the same solution as the primary antibody. Sections were incubated in Hoechst 33258 (1:5000) for 5 min rinsed twice with distilled water and then mounted on glass slides.

Golgi staining. Golgi impregnation was performed using a Rapid Golgi Stain Kit (FD Neuro Technologies) according to the manufacturer's protocol. Z-stacks of Golgi-stained CA1 neurons were acquired with a 20× objective mounted on a Nikon Eclipse 90i upright automated microscope at 5 μm interval.

Interferon response reporter assay. The Mx2:luc reporter plasmid containing the Mx2-response element was co-transfected with a pAAV containing an expression cassette for *Renilla* luciferase for normalization plus either pAAV-shVEGFD or polyinosine-polycytidylic acid (poly(I:C)), Sigma); poly (I:C) transfected into cells is known to induce a strong interferon response. Neurons were harvested 30 hrs post-transfection. Luciferase activities were measured with the Dual-luciferase Assay kit (Promega, Mannheim, Germany). Data derive from three independent experiments, each performed in duplicates.

Animals. Procedures were done in accordance with German guidelines for the care and use of laboratory animals and to the respective European Community Council Directive 86/609/EEC.

Patch clamp recordings. Patch electrodes (3-4 MU) were made from borosilicate glass (1.5 mm, WPI, Sarasota, Fla., USA) and filled with intracellular solution (containing in mM: $KCH_3SO_4$, 145; NaCl, 8; HEPES, 10; $K_2$-phosphocreatine, 10; $Mg_2$-ATP, 4; $Na_3$-GTP, 0.3; pH 7.35 with KOH). The extracellular solution was an artificial cerebrospinal fluid (ACSF, in mM: NaCl, 125; KCl, 3.5; $MgCl_2$, 1.3; $NaH_2PO_4$, 1.2; $CaCl_2$, 2.4; glucose, 25; $NaHCO_3$, 26; gassed with 95% $O_2$ and 5% $CO_2$).

Reagents. The following drugs were used: TTX (Biotrend, Cologne, Germany), Bicuculline (Alexis Biochemicals, Gruenberg, Germany), MK801 (Tocris), Nifedipine (Sigma-Aldrich, Munich, Germany), Actinomycin D (Applichem, Darmstadt, Germany), recombinant mouse VEGFD, (R&D Systems GmbH, Wiesbaden-Nordenstadt, Germany), recombinant mouse VEGF and VEGFC (Biocat, Heidelberg, Germany).

Antibodies. Mouse monoclonal antibody to tubulin (Sigma); mouse monoclonal NeuN antibody (Chemicon); mouse monoclonal anti-phospho-p38 MAP kinase antibody (BD); rabbit polyclonal antibodies to the HA tag, anti-VEGFD antibodies, anti-VEGFR3 (Santa Cruz); rabbit polyclonal antibody to phosphor-CREB (Upstate-Millipore); rabbit polyclonal antibody to phosphor-CaMKII (Promega); rabbit polyclonal antibodies to phosphor-MSK1, phosphor-ATF2, phosphor-ERK, phosphor-Akt, phosphor-MKK4, phosphor-JNK, phosphor-p70, phosphor-GSKα/β (Cell Signaling). Rabbit polyclonal antibodies to DsRed (Clontech). AlexaFluor 488-, AlexaFluor 594-, and AlexaFluor 633-labeled secondary antibodies were from Molecular Probes (Eugene, Oreg., USA).

Example 1

Nuclear Calcium Controls Dendrite Geometry and Spine Density

To investigate the role of nuclear calcium signaling in the regulation of dendrite architecture, CaMBP4 was expressed in the nuclei of hippocampal neurons. CaMBP4 contains four repeats of the M13 calmodulin (CaM) binding peptide derived from the rabbit skeletal muscle myosin light chain kinase. CaMBP4 effectively inactivates the nuclear calcium/CaM complex and blocks genomic responses induced by nuclear calcium signaling. Morphometric analyses revealed that, compared to control, hippocampal neurons expressing CaMBP4 along with humanized *Renilla reniformis* green fluorescent protein (hrGFP) to visualize the cells, showed a significant decrease both in the total dendritic length and in the complexity of the dendrites assessed by Sholl analysis (FIG. 1 A to C). Expression of CaMBP4 also caused a significant decrease in dendritic spine density (FIG. 1 D to E), and a considerable shortening and thinning of the remaining spines (FIG. 1 F to G). A similar reduction in total dendritic length, dendritic complexity, and spine size and density was observed in hippocampal neurons expressing CaMKIVK75E, a dominant negative mutant of CaMKIV (FIG. 1). These results indicate that nuclear calcium is an important signal in the control of dendritic geometry and spine density.

Example 2

Nuclear Calcium-CaMKIV Signaling Regulates VEGFD Expression

Next it was attempted to identify nuclear calcium/CaMKIV-regulated genes that mediate the observed structural changes. Examination of transcriptome data obtained from hippocampal neurons expressing CaMBP4 hinted at Vascular Endothelial Growth Factor D (VEGFD) as a possible candidate. VEGFD is well known for its role in angiogenesis and lymphangiogenesis in healthy tissues and in several types of cancer. VEGFD is detectable in the nervous system but a function for this secreted factor in neurons has not been described, although two other VEGF family members, VEGF (also known as VEGFA) and VEGFC, have been implicated in neurogenesis and the maturation of newly-born neurons. Quantitative reverse transcriptase PCR (qRT-PCR) analysis revealed that VEGFD is expressed in cultured hippocampal neurons, and reaches peak levels of expression after a culturing period of 10 to 13 days (FIG. 2A, 3A). VEGFD mRNA and protein are detectable in cultured neurons and in vivo at different developmental stages in the mouse hippocampus and cortex (FIG. 3 C to F). VEGFD expression is significantly lower in hippocampal neurons infected with a recombinant adeno-associated virus (rAAV) containing an expression cassette for either CaMBP4 (rAAV-CaMBP4) or CaMKIVK75E (rAAV-CaMKIVK75E) than in uninfected neurons or in neurons infected with an rAAV expressing LacZ (rAAV-LacZ) (FIG. 2B, 3A). The expression levels of many other genes, including other members of the VEGF family, were not affected by CaMBP4 or CaMKIVK75E (FIG. 3B). The neurotropism of these rAAVs specifically targets neurons over glia, indicating that the modulation of VEGFD expression is restricted to neurons.

To investigate a possible contribution of neuronal activity to VEGFD expression, cultured hippocampal neurons were treated with TTX for 5 days (from day in vitro 5 until the time point of gene expression analysis on day in vitro 10). It was found that compared to controls, this treatment reduced expression of VEGFD and also that of cFos, a well characterized neuronal activity marker (FIG. 2C). For several other genes analyzed in parallel, no differences in expression levels following TTX treatment were found (FIG. 2C). Given the prolonged duration of the TTX treatment, the possibility that the observed reduction in VEGFD expression may be caused indirectly through secondary effects cannot be ruled out. To determine if VEGFD mRNA levels are affected by an increase in synaptic activity, hippocampal neurons were exposed to the GABAA receptor blocker bicuculline. This treatment relieves tonic, GABAA receptor-mediated inhibition of synaptic transmission from the hippocampal network and induces bursts of action potentials (Aps). Bicuculline treatment caused a robust induction of cFos mRNA but did not alter VEGFC or VEGFD mRNA levels (FIG. 2D). To investigate the involvement of NMDA receptors and voltage-gated calcium channels in VEGFD expression, hippocampal neurons were treated with the NMDA receptor blocker MK801 and/or nifedipine, a blocker of L-type voltage-gated calcium channels. Both MK801 and nifedipine significantly reduced the expression of VEGFD mRNA; treatment with a combination of both channel blockers yielded the largest reduction in VEGFD mRNA levels (FIG. 2E). These results indicate that VEGFD expression is controlled by basal neuronal activity through a mechanism that is initiated by NMDA receptors and L-type voltage-gated calcium channels and requires nuclear calcium-CaMKIV signaling.

Because the observed reduction of VEGFD mRNA levels following inhibition of nuclear calcium signaling could be due to a change in VEGFD mRNA stability, the half life of VEGFD mRNA was determined next. The levels of VEGFD mRNA, and in parallel those of cFos, were measured in both uninfected and rAAV-CaMBP4 infected hippocampal neurons before and at various time points (0.5 h to 24 hrs) after treatment of the cells with actinomycin D, an inhibitor of gene transcription. It was found that VEGFD mRNA has a half life of more than 24 hours in uninfected hippocampal neurons; a virtually identical decay rate for VEGFD was observed in rAAV-CaMBP4 infected neurons (FIG. 2F), although compared to uninfected controls, the absolute amounts of VEGFD mRNA in these neurons were lower (see also FIG. 2B, 3A). Analysis of cFos mRNA revealed a half life of less than 1 hour (FIG. 2F). These results indicate that the regulation of VEGFD expression by nuclear calcium signaling takes place at the level of gene transcription rather than at the post-transcriptional level.

Example 3

CBP Regulates VEGFD Expression

In silico analysis using TESS (Transcription Element Search System; http://www.cbil.upenn.edu/cgi-bin/tess/tess) of a 2000 base pairs long upstream regulatory region of the murine VEGFD gene revealed a large number of possible binding sites for several transcription factors including the AP-1 complex, NF-AT, MEF-2, HiNF, NF-κB, POU2-Oct and HNF4. However, a cAMP Response Element (CRE) appears to be lacking, suggesting that nuclear calcium-CaMKIV mediated regulation of VEGFD takes place by transcription factors other than CREB, the prototypical target of this signaling pathway. Because the activity of the transcriptional co-activator CBP is controlled by nuclear calcium and CaMKIV, the role of CBP in VEGFD regulation was tested next. CBP interacts with a variety of transcription factors, which includes some of those for which putative binding sites have been identified in the VEGFD gene (see above). Moreover, a contribution of CBP to the regulation of the human VEGFD promoter in cancer cells has been suggested. To directly investigate a possible role of CBP in the regulation of the endogenous VEGFD gene in hippocampal neurons, the neurons were infected with an rAAV expressing the adenovirus protein E1A. E1A binds to CBP via its amino-terminal conserved region 1 (CR1) and disrupts CBP function. As expected, rAAV-mediated expression of E1A blocked the AP bursting-induced increase in the expression of cFos (FIG. 2G), a known target of the CREB/CBP transcription factor complex. Expression of E1A also significantly reduced VEGFD mRNA levels (FIG. 2G). Infection of hippocampal neurons with an rAAV expressing a mutant version of E1A (E1AΔCR1) that lacks CR1 and fails to interact with CBP had no effect on cFos regulation or VEGFD transcription (FIG. 2G). RNA interference (RNAi) was also used to specifically decrease CBP mRNA levels in hippocampal neurons (FIG. 2H). This caused a significant reduction of VEGFD mRNA levels (FIG. 2H), confirming the role of CBP in modulating VEGFD transcription. A morphometric analysis revealed that hippocampal neurons expressing E1A have shorter and simplified dendritic trees compared to neurons expressing E1AΔCR1 (FIG. 2 I to J). These results indicate that CBP acts downstream of nuclear calcium-CaMKIV signaling to regulate VEGFD expression in hippocampal neurons.

Example 4

VEGFD Restores Dendrite Complexity but not Spine Density in Nuclear Calcium Signaling-Depleted Neurons To investigate whether VEGFD is involved in mediating the effects of nuclear calcium-CaMKIV signaling on neuronal structure, hippocampal neurons were either transfected or infected, respectively, with an rAAV plasmid (pAAV-VEGFD) or an rAAV (rAAVVEGFD) containing an expression cassette for HA-tagged VEGFD, or the neurons were treated with recombinant VEGFD (rVEGFD). Expression of HA-tagged VEGFD was detected immunocytochemically and by immunoblotting in rAAV-VEGFD infected hippocampal neurons and in the culture media (FIG. 3 G, H). Although VEGFD-HA expression or exogenously applied rVEGFD had no detectable effect on neuronal morphology, both treatments rescued the reduction in dendrite length and complexity caused by expression of CaMBP4 or CaMKIVK75E (FIG. 4 A to C, E to F). In contrast, VEGFD-HA and rVEGFD failed to restore normal spine density in CaMBP4 or CaMKIVK75E expressing neurons (FIG. 4 D, G), indicating that the mechanisms through which nuclear calcium-CaMKIV signaling regulate dendrite geometry and spine density are distinct. Because VEGFD belongs to a family of closely related factors that, in part, share the receptors, it was tested whether VEGF or VEGFC also affect dendrite arborization. However, neither recombinant VEGF (rVEGF) nor recombinant VEGFC (rVEGFC) was able to rescue the reduction in dendrite length and complexity caused by CaMBP4 or CaMKIVK75E expression (FIG. 5), indicating a specific role for VEGFD in the control of dendrite arborization by nuclear calcium-CaMKIV signaling.

Example 5

VEGFD Autocrine Signaling is Essential for Complex Dendritic Arborization

To determine whether the observed reduction in VEGFD expression which followed blockade of nuclear calcium-CaMKIV signaling is sufficient to alter dendritic architecture, RNAi was used to lower VEGFD expression in hippocampal neurons. DNA sequences encoding short hairpin RNAs (shRNAs) designed to target the mouse VEGFD mRNA were inserted downstream of the U6 promoter of an rAAV vector. The resulting rAAV, rAAV-shVEGFD, also harbors a calcium/calmodulin-dependent protein kinase II (CaMKII) promoter-containing expression cassette for the red fluorescent protein mCherry (FIG. 6A). Control rAAVs were identical to rAAV-shVEGFD except that they either lacked DNA sequences encoding shRNAs (rAAV-emptymC) or contained DNA sequences encoding a scrambled version of the VEGFD-specific shRNA (rAAV-shSCR). Infection rates of 80 to 95 percent of the neuron population were obtained for all three rAAVs (FIG. 7 A, B). qRT-PCR and immunoblot analysis revealed that rAAVshVEGFD, but not rAAV-shSCR or rAAV-emptymC, reduced VEGFD mRNA levels and blocked VEGFD protein expression (FIG. 6B; FIG. 7C). Expression of VEGFC was not affected by rAAV-shVEGFD or by the two control rAAVs (FIG. 6B). It has been reported that expression of certain shRNAs can have an effect on neuronal morphology due to the induction of an interferon response. However, using an interferon-responsive reporter gene system no evidence for an interferon response induced by rAAV-shVEGFD was found (FIG. 7D). In addition, no increase in cell death in hippocampal neurons infected with rAAV-shVEGFD was observed (FIG. 7E).

Morphological analyses revealed that, compared to hippocampal neurons transfected with pAAV-shSCR or pAAV-emptymC, neurons transfected with pAAV-shVEGFD showed a less complex dendritic arbor and a reduction in total dendritic length (FIG. 6 C to E). In contrast, RNAi-mediated knock-down of VEGFD did not change spine density (number of spines/20 μm: 7.1±0.36, pAAV-emptymC; 6.17±0.56, pAAV-shSCR; 6.52±0.51, pAAV-shVEGFD). Similar results were obtained with different shRNA sequences directed against VEGFD (FIG. 7F). The effect of pAAV-shVEGFD transfection on the dendritic tree could be reversed by treatment with rVEGFD. In contrast, rVEGFD did not affect dendrite length or complexity of hippocampal neurons transfected with pAAV-shSCR and pAAV-emptymC (FIG. 6 C to E). These results identify a role for VEGFD in the regulation of dendritic architecture and further support the above-mentioned concept (see FIG. 4) that dendrite arborization and spine morphogenesis are controlled by distinct nuclear calcium/CaMKIV-regulated processes.

The observation that the dendrite structure is altered in shVEGFD expressing neurons even if the surrounding, untransfected cells have a normal VEGFD expression level suggests a possible autocrine mechanism of action of VEGFD. To investigate this deeper, hippocampal neurons were transfected with pAAV-VEGFD-HA or with a plasmid containing an expression cassette for HA-tagged VEGFD resistant to shVEGFD (pAAVresiVEGFD-HA) together with pAAV-shVEGFD in order to over-express VEGFD in the same neurons expressing shVEGFD. Expression of resiVEGFD-HA rescued the reduction of dendrite length and complexity caused by expression of shVEGFD (FIG. 6F, H), indicating that VEGFD acts in an autocrine manner. This conclusion is further supported by an experiment in which hippocampal neurons were first infected with rAAV-VEGFD and subsequently transfected with pAAV-shVEGFD. Since infection rates are very high but transfection rates are very low, this creates a situation in which a small number of transfected cells with low VEGFD expression levels and reduced dendrite length and arborization are surrounded by infected cells overexpressing VEGFD. It was found that even under these conditions the impairment in dendrite morphology caused by shVEGFD cannot be overcome by the VEGFD overexpressed in the infected neurons (FIG. 7 G to I). Thus, although paracrine action of VEGFD cannot be fully excluded, all available evidence strongly suggests that VEGFD regulates total dendrite length and complexity through an autocrine mechanism.

Example 6

VEGFD Regulates Dendritic Arborization Via VEGFR3

Human VEGFD and its close relative VEGFC can bind and activate both Vascular Endothelial Growth Factor Receptor 2 and 3 (VEGFR2 and VEGFR3); however, murine VEGFD can only activate VEGFR3. To investigate whether dendritic architecture is specifically controlled by VEGFD acting via VEGFR3, rAAVs expressing shRNAs specific for VEGF (rAAV-shVEGF), VEGFC (rAAV-shVEGFC), and VEGFR3 (rAAV-sh VEGFR3) were generated. Using qRT-PCR it could be shown that rAAV-shVEGF, rAAV-shVEGFC, rAAV-sh VEGFR3, and rAAV-shVEGFD reduced mRNA levels of their respective targets leaving unaltered the expression of the other VEGF family members (FIG. 8A). Morphological analyses revealed that transfection of hippocampal neurons with pAAVshVEGF or pAAV-shVEGFC, similar to transfection with the control plasmids, pAAVshSCR or pAAV-emptymC, had no effect on dendrite length or complexity (FIG. 8 B to D). In contrast, knock-down of VEGFR3 by transfecting neurons with pAVV-VEGFR3 led to changes in the dendritic structure that were virtually identical to those obtained in hippocampal neurons transfected with pAAV-shVEGFD (FIG. 8 B to D; see also FIG. 6 C to H, and FIG. 7 G to I), for the effects of pAAV-shVEGFD on dendrite morphology). These results indicate that amongst VEGF family members, VEGFD, acting through VEGFR3, plays a specific role in the regulation of dendrite arborization.

Example 7

VEGFD Regulates Multiple Signaling Pathways in Hippocampal Neurons and Shapes Dendrite Morphology Via p38 MAP Kinase Activation Next, the signaling mechanisms through which VEGFD controls dendrite architecture were determined. Cell lysates from hippocampal neurons treated with rVEGFD for various lengths of time were subjected to immunoblot analysis using a large panel of antibodies that are specific for the phosphorylated (i.e. activated) forms of signaling molecules (FIG. 9). It was found that rVEGFD activates ERK1/2, p38 MAP kinase (MAPK) and CREB (FIG. 9A, B). The increase in ERK1/2 phosphorylation and CREB phosphorylation (which takes place in neurons and not in glial cells as shown by double immunostaining using the neuronal marker NeuN; FIG. 9C) was significant but moderate (FIG. 9A, B). In contrast, the activation of p38 MAPK was very robust (FIG. 9A, B), indicating that it may be a major transducer of VEGFD signaling in hippocampal neurons. Therefore, it was determined whether p38 MAPK mediates the effects of VEGFD on dendrite geometry. Indeed, selective blockade of p38 MAPK using the p38 MAPK inhibitor SB203580 severely compromised the ability of rVEGFD to rescue the impairment of dendrite length and complexity in hippocampal neurons expressing CaMBP4 and CaMKIVK75E (FIG. 9D, E; see also FIG. 4A, E to F). Because SB203580 inhibits the alpha and beta isoforms of p38 MAPK, the role of p38 MAPK in VEGFD-mediated dendritic arborization by RNAi was further investigated. Two pAAVs, shp38α and shp38β, that contain expression cassettes for shRNAs specific for the alpha and the beta isoform, respectively, of p38 MAPK, were generated. It was found that the reduction of p38 alpha MAPK expression prevented the rVEGFD-induced rescue of the dendrite phenotypes of hippocampal neurons expressing CaMBP4 (FIG. 9F). These results indicate that p38 alpha MAPK is required for VEGFD regulation of dendrite architecture.

Example 8

VEGFD Modulates Network Activity

To investigate whether VEGFD-regulated changes in the structure of dendrites are associated with changes in neuronal network activity, microelectrode array (MEA) recordings were used. Indeed, the spike frequencies of hippocampal cultures infected with rAAV-shVEGFD were reduced compared to cultures infected with rAAV-shSCR or rAAV-emptymC. This decrease could be partly rescued by the addition of rVEGFD to the media (FIG. 10A). The decrease in network activity caused by infection with rAAVshVEGFD was first observed at day in vitro (DIV) 10 (FIG. 10A), coinciding with the onset of robust VEGFD mRNA expression in vitro (see FIG. 2A, 3A).

Example 9

Patch Clamp Recordings Verify Reduced Surface Area and Excitability after Silencing VEGFD Expression The effects of silencing VEGFD expression on the electrical properties of neurons was investigated with whole-cell patch clamp (Table 1, FIG. 10B). Neurons either transfected with pAAV-shVEGFD or infected with rAAV-shVEGFD showed, in comparison to their respective control group, a markedly smaller membrane capacitance indicative of a reduced plasma membrane surface area, a finding consistent with the observed reduction in dendritic arborization (FIG. 6, 8). Despite this difference, shVEGFD-expressing neurons did not show an altered resting membrane potential or threshold membrane potential for action potential initiation (Table 1). This reflects the healthy integrity of these neurons despite their altered morphology. Slightly more current injection was necessary to elicit an action potential in shVEGFD expressing cells although this trend was only significant in the group of hippocampal neurons in which infection was used to express shVEGFD (Table 1). Moreover, stronger accommodation was found in spike patterns induced by square wave current injections in shVEGFD expressing neurons (data not shown). This suggests a mildly reduced excitability in shVEGFD expressing neurons, consistent with the reduced absolute spike frequency identified with MEA recordings (see FIG. 10A). Increased accommodation may be due to a reduced contribution of dendritic sodium channels, h-channels or calcium activated potassium channels, which in pyramidal neurons can drive slow repetitive firing and influence burst waveforms.

synapses in shVEGFD expressing cells. mEPSCs of hippocampal neurons expressing shVEGFD also showed faster rise and decay time constants than their respective shSCR expressing controls (FIG. 10C, Table 1), most likely due to reduced filtering of mEPSCs in their more compact dendritic trees. Alternatively, a synaptic NMDA-receptor mediated slow component of the mEPSC may have been reduced in shVEGFD expressing neurons, although significant NMDA currents are unlikely in our recording conditions (−71 mV holding potential, 1.3 mM $Mg^{2+}$). Responses were also recorded to bath applied AMPA, which produced a peak within 30 s whose amplitude was used as an indication of the total number of functional AMPA receptors per cell (FIG. 10D). AMPA response amplitudes were smaller in hippocampal neurons expressing shVEGFD (FIG. 10D, G) indicative of a reduced total number of surface-expressed AMPA receptors per cell. Taken together, this patch clamp analysis has identified a reduced plasma membrane surface area, as well as a reduced number of AMPA receptor-containing synapses, a reduced number of AMPA receptors per synapse and a reduced total number of AMPA receptors in shVEGFD expressing cells. These results are consistent with the reduced dendritic morphology identified by morphometric analyses.

TABLE 1

Effects of silencing VEGFD expression on the electrical properties of neurons as measured with whole-cell patch clamp

| | $V_{rest}$ (mV) | Cm (pF) | Rm (MΩ) | AP thresh (mV) | AP induc thresh (pA) | mEPSC τ rise (ms) | mEPSC τ decay (ms) |
|---|---|---|---|---|---|---|---|
| shSCR infected (n = 31) | −78.7 ± 1.7 | 102.4 ± 4.4 | 275 ± 15 | −48.4 ± 1.0 | 116 ± 10 | 3.36 ± 0.07 | 5.70 ± 0.12 |
| shVEGFD infected (n = 26) | −82.9 ± 1.9 | 68.3 ± 3.3 **** | 316 ± 19 | −46.5 ± 1.1 | 162 ± 14 | 2.91 ± 0.10 *** | 4.14 ± 0.15 **** |
| shSCR transfected (n = 26) | −76.5 ± 2.3 | 88.6 ± 5.5 | 291 ± 32 | −44.1 ± 1.6 | 125 ± 13 | 3.18 ± 0.14 | 6.06 ± 0.07 |
| shVEGFD transfected (n = 27) | −79.7 ± 2.0 | 59.7 ± 3.8 **** | 352 ± 29 | −45.6 ± 1.6 | 149 ± 14 | 2.82 ± 0.23 | 3.82 ± 0.26 *** |

Passive membrane properties, action potential thresholds and mEPSC kinetics. Values indicate resting membrane potential (Vrest), Membrane capacitance (Cm), membrane resistance (Rm), the membrane potential at which action potentials initiate (AP thresh), the current injection required to induce an action potential (AP induc thresh) and the rise and decay time constants of mEPSCs. Significant differences between shVEGFD expressing cells and their respective transfected or infected shSCR-expressing controls are indicated (*p < 0.001, ** p < 0.0001) using a Kolmogorov-Smirnov test for independent samples.

Example 10

Lowering VEGFD Expression Reduces the Number of Functional AMPA Receptors

The influence of VEGFD expression on synaptic transmission in hippocampal neurons in culture was directly assessed by recording miniature excitatory postsynaptic currents (mEPSCs) in the presence of TTX and the GABAA receptor blocker gabazine. Neurons transfected with pAAV-shVEGFD or infected with rAAV-shVEGFD showed longer mEPSC inter-event intervals (IEIs, 1/frequency) and smaller mEPSC amplitudes than their respective shSCR expressing controls (FIG. 10 E to F). The reduced mEPSC frequency in transfected hippocampal neurons suggests that the effect was not mediated by a reduced release probability presynaptically since the low transfection rate ensures that the majority of synaptic input to shRNA expressing cells comes from non-shRNA expressing cells. The reduced mEPSC frequency is thus most likely indicative of fewer AMPA receptor-containing synapses per cell. The 21 to 24% reduction in mEPSC amplitude also suggests a lower density of AMPA receptors at Example 11

VEGFD Shapes Dendritic Arborization In Vivo

Next, the role of VEGFD in vivo was investigated. rAAV-shVEGFD or the appropriate control rAAVs were stereotaxically delivered to the dorsal hippocampus of 2 month old C57BL/6 male mice. Infected neurons were readily identified by analysis of the mCherry fluorescence (FIG. 12). The morphology of neurons in the CA1 area of the hippocampus was assessed by manually tracing the basal dendrites of Golgi-stained brain slices obtained from animals 2.5 weeks after viral gene delivery. As in cultured neurons, infection of hippocampal neurons in vivo with rAAV-shVEGFD but not with rAAVshSCR or rAAV-emptymC reduced both the total length of dendrites and their complexity (FIG. 11 A to C).

Example 12

VEGFD is Required for Memory Formation

Finally, it was investigated whether the changes in neuronal structure induced by RNAi-mediated knock-down of VEGFD causes cognitive deficits. Mice stereotaxically injected with rAAV-shVEGFD or rAAV-shSCR into the hippocampus were tested in two well characterized hippocampus-dependent memory tests: Morris water maze and contextual fear conditioning. In the hidden-platform version of the Morris water maze, mice learn the location of the platform using distal visual cues. It was found that mice stereotaxically injected with rAAV-shSCR or rAAV-shVEGFD needed significantly less time to find the hidden platform across training trials (main effect of training session: $F[7,91]=11.30$, $p<0.0001$), however no effect of treatment was observed (main effect of treatment: $F[1,13]=1.34$, $p=NS$) (FIG. 11D). This suggests that both groups have developed a learning strategy to find the hidden platform. Multiple behavioral strategies may be employed by the mice to obtain the reward (escape from water) and some of these strategies may be comparably efficient but distinct on the requirement for hippocampal function. To assess spatial memory, a probe trial was performed during which the platform was removed from the water maze and the mice were given 60 sec to search for it. The search pattern during the probe trial can reveal a spatial preference that is believed to represent spatial memory. It was observed that rAAV-shSCR injected mice show a spatial preference for the target quadrant whereas rAAV-shVEGFD injected mice did not (FIG. 11E). This was expressed as a significantly higher time spent in the target quadrant by the rAAV-shSCR injected mice in comparison to the other quadrants (One-way ANOVA: $F[3,28]=9.84$, $p<0.001$; multiple post-hoc comparisons: time in target quadrant versus time in adjacent or opposite quadrants; $p<0.05$). In contrast, rAAV-shVEGFD injected mice spent similar amounts of time in the different quadrants ($F[3,24]=1.2$, $p=NS$). This suggests that the rAAV-shVEGFD injected mice did not develop a spatial searching strategy pointing to spatial memory impairment in these mice. Swimming speed was not different between the two groups (FIG. 11F, main effect of treatment: $F[1,13]=3.94$, $p=NS$).

To determine whether abnormalities in motivation, motor coordination or vision could account for the deficit in spatial memory, mice were also trained on a visible-platform version of the water maze, a hippocampus-independent task. In this task, the mice use a proximal, visual cue to locate the platform (FIG. 11G). rAAV-shSCR and rAAV-shVEGFD injected mice showed similar escape latencies to find the visible platform (main effect of training session: $F[2,26]=7.12$, $p<0.01$; main effect of treatment: $F[1,13]=0.36$, $p=NS$) demonstrating that both groups acquired the task (FIG. 11G). Overall, these results suggest that rAAV-shVEGFD injected mice have impaired spatial memory.

In the contextual fear conditioning, mice learn the association between an aversive stimulus, a mild foot shock, and the context where it was delivered. In mice that have formed an associative memory, a second exposure to the same context induces a fearful response expressed as freezing or immobility, parameters used to quantify the formation of memory. It was found that mice stereotaxically injected with rAAVsh-VEGFD showed significantly lower levels of freezing during the 24-hour test session than did mice injected with rAAV-shSCR (FIG. 11H). The reduction in freezing levels was not due to decreased locomotor activity or pain sensitivity since the basal exploratory activity and reaction to shock during the training session were not different between the two groups (FIG. 11I, J). These findings together with the results obtained with the Morris water maze indicate that VEGFD is important for memory formation.

Example 13

Selected Peptides Display Agonistic Activity at VEGFR2/3

It was reasoned that peptides could be generated to act as mimics of VEGF-D, which could have potential clinical implications.

The recently reported structural data of VEGF-D provided some insight on the essential structural features for the molecular interactions between VEGF-D and VEGFR-2. Based on this data, a sequence motif in VEGF-D was identified which was expected to have agonistic properties at the receptor. This sequence was varied in a systematic manner to identify analogs with increased agonistic activity. Since the helical folding of the motif appears to be of critical relevance, residues and pairs of residues that tend to increase the propensity for helical folding were introduced. Among these residues were alanine, the non-natural amino acids alpha-amino-isobutyric acid (aib) and gabapentine (gpn) as well as pairs of cationic and anionic amino acids (FIG. 13).

Next, the efficiency of the library of synthesized peptides in producing the same biological effects of recombinant VEGFD in neuronal cells was tested. p38 MAP kinase is a key player in the process that links VEGFD signaling to dendrite architecture. For this reason, the potency of the peptides to induce the activation of p38 MAP kinase was measured. To this aim, cell lysates from hippocampal neurons treated with rVEGFD or with one of the peptides (7.7 nM, 2 hours) were subjected to immunoblot analysis using antibodies that are specific for the phosphorylated (i.e., activated) form of p38 MAP kinase. In addition, samples were also tested for the activity of GSK-3 $\alpha/\beta$ and $\alpha$-tubulin was used as a gel loading control. The results of this activity screening are shown in FIG. 13. In each round of experiments, rVEGFD was used in parallel as positive control and represents the threshold. All peptides inducing p38 MAP kinase activity at identical or higher levels as rVEGFD passed the cut-off. The values of p38 MAP kinase activity expressed as percentage of control unstimulated can be seen in FIG. 13 under the column “P38”.

The peptides were also submitted to a negative selection. To this end, the values of GSK-3 $\alpha/\beta$ activity, which is not altered by treatment with rVEGFD (FIG. 13, column “GSK”) were measured. All peptides decreasing or increasing GSK-3 $\alpha/\beta$ activity of 25% as compared to control were excluded by further analysis.

Next, the peptides that passed the positive (induction of p38 MAP kinase activity) and negative (no effect on GSK-3 $\alpha/\beta$ activity) selections were scored for their potency to activate p38 MAP kinase. The ratio between the raw value of p38 MAP kinase induction and the value of p38 MAP kinase induction given by rVEGFD was calculated in order to identify peptides less/more potent than rVEGFD. According to these scores, peptides were then divided in classes (FIG. 13, columns “efficacy on rec” and “bin”).

Surprisingly, certain positions in the sequence to be particularly sensitive were found for amino acid substitutions and exchanges, such as positions 6 and 7. It was also found that the gpn residue is not generally associated with increased activity, but that the “helix-formers” Ala and aib have a pronounced positive effect when introduced in positions 6 and 7.

The six most potent peptides (#6, #21, #59, #60, #65, #69) were tested for their efficacy to modulate dendritic length and complexity.

It is known that blocking nuclear calcium signalling by over-expressing CaMBP4 (Calcium/Calmodulin Binding Peptide 4) results in a decrease of dendritic length and complexity which can be rescued to normal levels by treating neurons with rVEGFD (FIG. 14). The ability of six selected peptides to rescue the reduction of dendrite length and complexity caused by expression of CaMBP4 was tested (FIG. 15).

Further, primary hippocampal neurons were transfected with hrGFP (to visualize the entire dendritic arborization) and, when indicated, also with CaMBP4 to cause an impairment in the dendritic tree. Afterwards, neurons were treated with the indicated peptide and then morphometric analysis was performed. Total dendritic length and complexity was measured; the results of these analyses are shown in FIG. 16. The six peptides were capable to restore normal dendritic length and complexity.

The invention claimed is:

1. A method for increasing at least one of the length and the complexity of the dendrites of a human subject's mature neuronal cells for maintaining dendritic connections, comprising administering Vascular endothelial growth factor receptor 2 and/or 3 (VEGFR2/3) activating agent to a human subject's mature neuronal cells, said VEGFR2/3 activating agent selected from peptides consisting of at least one of the amino acid sequence of SEQ ID Nos: 9 to 14.

2. The method according to claim 1, wherein the subject is suffering from age- and/or disease-related cognitive dysfunction and wherein increasing at least one of the length and the complexity of the dendrites of a subject's neuronal cells is for the treatment of an age- and/or disease-related cognitive dysfunction in the subject.

3. The method according to claim 2, wherein the cognitive dysfunction is caused by a condition selected from the group consisting of cerebral ischemia, Down syndrome, Rett syndrome, neurodegenerative disease, Alzheimer's disease, ageing, metabolic dysfunction, and infection with human immunodeficiency virus (HIV).

* * * * *